US011208480B2

(12) United States Patent
Gauthier et al.

(10) Patent No.: US 11,208,480 B2
(45) Date of Patent: Dec. 28, 2021

(54) MULTISPECIFIC ANTIGEN BINDING PROTEINS

(71) Applicant: INNATE PHARMA, Marseilles (FR)

(72) Inventors: Laurent Gauthier, Marseilles (FR); Benjamin Rossi, Marseilles (FR)

(73) Assignee: INNATE PHARMA, Marseilles (FR)

( * ) Notice: Subject to any disclaimer, the term of this patent is extended or adjusted under 35 U.S.C. 154(b) by 226 days.

(21) Appl. No.: 15/321,674

(22) PCT Filed: Jun. 23, 2015

(86) PCT No.: PCT/EP2015/064070
§ 371 (c)(1),
(2) Date: Dec. 22, 2016

(87) PCT Pub. No.: WO2015/197598
PCT Pub. Date: Dec. 30, 2015

(65) Prior Publication Data
US 2017/0210802 A1    Jul. 27, 2017

Related U.S. Application Data

(60) Provisional application No. 62/017,913, filed on Jun. 27, 2014.

(51) Int. Cl.
*C07K 16/28* (2006.01)
*C07K 16/00* (2006.01)
*C07K 16/30* (2006.01)

(52) U.S. Cl.
CPC .......... *C07K 16/2803* (2013.01); *C07K 16/00* (2013.01); *C07K 16/2809* (2013.01); *C07K 16/30* (2013.01); *C07K 2317/31* (2013.01); *C07K 2317/52* (2013.01); *C07K 2317/522* (2013.01); *C07K 2317/526* (2013.01); *C07K 2317/55* (2013.01); *C07K 2317/56* (2013.01); *C07K 2317/622* (2013.01); *C07K 2317/71* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,229,275 A | 7/1993 | Goroff | |
| 5,565,332 A | 10/1996 | Hoogenboom et al. | |
| 5,567,610 A | 10/1996 | Borrebaeck et al. | |
| 5,573,905 A | 11/1996 | Lerner et al. | |
| 6,162,963 A | 12/2000 | Kucherlapati et al. | |
| 6,737,056 B1 | 5/2004 | Presta | |
| 6,821,505 B2 | 11/2004 | Ward | |
| 7,122,637 B2 | 10/2006 | Presta | |
| 7,183,387 B1 | 2/2007 | Presta | |
| 7,332,581 B2 | 2/2008 | Presta | |
| 7,355,742 B2 | 2/2008 | Presta | |
| 7,355,008 B2 | 4/2008 | Stavenhagen et al. | |
| 7,371,826 B2 | 5/2008 | Presta | |
| 7,416,727 B2 | 8/2008 | Presta | |
| 7,425,619 B2 | 9/2008 | Koenig et al. | |
| 7,521,542 B2 | 4/2009 | Johnson et al. | |
| 7,632,497 B2 | 12/2009 | Stavenhagen | |
| 2002/0161201 A1 | 10/2002 | Filpula et al. | |
| 2004/0242851 A1* | 12/2004 | Zhu | C07K 16/2863 530/388.22 |
| 2005/0238646 A1 | 10/2005 | Ledbetter et al. | |
| 2006/0074225 A1 | 4/2006 | Chamberlain et al. | |
| 2006/0275254 A1* | 12/2006 | Kim | C07K 19/00 424/85.1 |
| 2009/0155275 A1* | 6/2009 | Wu | C07K 16/468 424/136.1 |
| 2010/0316645 A1* | 12/2010 | Imhof-Jung | C07K 16/22 424/136.1 |
| 2012/0201746 A1* | 8/2012 | Liu | C07K 16/00 424/1.11 |

FOREIGN PATENT DOCUMENTS

| | | |
|---|---|---|
| EP | 1176195 | 1/2002 |
| WO | WO 9211018 | 7/1992 |
| WO | WO 9954342 | 10/1999 |
| WO | WO 0042072 | 7/2000 |
| WO | WO 03035835 | 5/2003 |
| WO | WO 04063351 | 7/2004 |
| WO | WO 04099249 | 11/2004 |
| WO | WO 2005/000086 | * 1/2005 |
| WO | WO 2005000086 | 1/2005 |
| WO | WO 05047327 | 5/2005 |
| WO | WO 2005040219 | 5/2005 |
| WO | 2005/061547 | 7/2005 |
| WO | WO 05110474 | 11/2005 |

(Continued)

OTHER PUBLICATIONS

Feige et al. (Molecular Cell, 34:569-579, 2009).*
Stancovski et al. (PNAS, 88: 8691-8695, 1991).*
Jiang et al. (J. Biol. Chem., 280: 4656-4662, 2005).*
Rozan C, et al., "Single domain antibody-based and linker-free bispecific antibodies targeting FcγRIII induce potent anti-tumor activity without recruiting regulatory T cells," Mol Cancer Ther. Aug. 2013;12;(8)1481-91.
Müller KM, et al., "The first constant domain (CH1 and CL) of an antibody used as heterodimerization domain for bispecific miniantibodies," FEBS Lett. Jan. 30, 1998;422(2):259-64.

(Continued)

*Primary Examiner* — Nelson B Moseley, II
(74) *Attorney, Agent, or Firm* — Robin L. Teskin; Baker, Donelson, Bearman, Caldwell & Berkowitz PC

(57) ABSTRACT

Multimeric multispecific proteins formed from dimerization between CH1 and CK domains and that bind two target antigens are provided. The proteins have advantages in production and in the treatment of disease, notably cancer or infectious disease.

8 Claims, 19 Drawing Sheets
Specification includes a Sequence Listing.

(56) References Cited

FOREIGN PATENT DOCUMENTS

| WO | WO 2005105858 |   | 11/2005 |
|----|---------------|---|---------|
| WO | WO 05115452   |   | 12/2005 |
| WO | WO 2006031994 |   | 3/2006  |
| WO | WO 2006/053301 | * | 5/2006 |
| WO | WO 2006064136 |   | 6/2006  |
| WO | WO 06088494   |   | 8/2006  |
| WO | WO 06133148   |   | 12/2006 |
| WO | WO 2007021841 |   | 2/2007  |
| WO | WO 07024249   |   | 3/2007  |
| WO | WO 2007073499 |   | 6/2007  |
| WO | WO 2007106707 |   | 9/2007  |
| WO | WO 2008002933 |   | 1/2008  |
| WO | WO 2008105886 |   | 9/2008  |
| WO | WO 2008119353 |   | 10/2008 |
| WO | WO 2009089004 |   | 7/2009  |
| WO | WO 2010032269 |   | 3/2010  |
| WO | WO 2011063348 |   | 5/2011  |
| WO | WO 2011066501 |   | 6/2011  |
| WO | WO 2011069104 |   | 6/2011  |
| WO | WO 2011109400 |   | 9/2011  |
| WO | WO 2011131746 |   | 10/2011 |
| WO | WO 2011133886 |   | 10/2011 |
| WO | WO 2012089814 |   | 7/2012  |
| WO | WO 2014044686 |   | 3/2014  |
| WO | 2015/197593   |   | 12/2015 |
| WO | 2015/197598   |   | 12/2015 |
| WO | 2016/207273   |   | 12/2016 |
| WO | 2016/207278   |   | 12/2016 |

OTHER PUBLICATIONS

Kufer P, et al., "A revival of bispecific antibodies," Trends Biotechnol. May 2004:22(5):238-44.

Low S, et al., "Inhibitors of the FcRn: IgG protein-protein interaction." AAPS J. Sep. 2009;11(3):432.

Hollander, N. "Bispecific antibodies for cancer therapy." Immunotherapy, Mar. 2009; 1(2):211-22.

Ying T. et al., "Soluble monomeric IgG1 Fc." J Biol Chem. Jun. 1, 2012;287(23):19399-408.

Idusogie EE, et al., "Mapping of the C1q binding site on rituxan, a chimeric antibody with a human IgG1 Fc," J Immunol. Apr. 15, 2000;164(8):4178-84.

Armour KL, et al., "Recombinant human IgG molecules lacking Fcγ receptor I binding and monocyte triggering activities," Eur J Immunol. Aug. 1999;29(8):2613-24.

Presta, L. G., et al., Engineering therapeutic antibodies for improved function. (2002): 487-490.

Shields RL, et al., "Lack of fucose on human IgG1 N-linked oligosaccharide improves binding to human FcγRIII and antibody-dependent cellular toxicity," J Biol Chem. Jul. 26, 2002;277(30):26733-40. Epub May 1, 2002.

Shields RL, et al., "High resolution mapping of the binding site on human IgG1 for Fc gamma RI, Fc gamma RII, Fc gamma RIII, and FcRn and design of IgG1 variants with improved binding to the Fc gamma R." J Biol Chem. Mar. 2, 2001;276(9):6591-60. Epub Nov. 28, 2000.

Devereux J, et al., A comprehensive set of sequence analysis programs for the VAX. Nucleic Acids Res. Jan. 11, 1984;12(1 Pt 1):387-95.

Altschul SF, et al., "Basic local alignment search tool," J Mol Biol. Oct. 5, 1990;215(3):403-10.

Winter, C. C., et al., "Natural Killer Cells Protocols (edited by Campbell KS and Colonna M)." (2000): 219-238.

Gebauer M, et al., "Engineered protein scaffolds as next-generation antibody therapeutics," Curr Opin Chem Biol, Jun. 2009;13(3):245-55. Epub Jun. 6, 2009.

Jakobovitz A, et al., "Germ-line transmission and expression of a human-derived yeast artificial chromosome," Nature. Mar. 18, 1993;362(6417):255-8.

Ward ES, et al., "Binding activities of a repertoire of single immunoglobulin variable domains secreted from *Escherichia coli*," Nature. Oct. 12, 1989;341(6242):544-6.

McCafferty J, et al., "Phage antibodies: filamentous phage displaying antibody variable domains," Nature. Dec. 1990;348(6301):552-53.

Griffiths AD, et al., "Human anti-self antibodies with high specificity from phage display libraries," EMBO J. Feb. 1993;12(2):725-34.

McDonagh CF, et al., "Antitumor activity of a novel bispecific antibody that targets the ErbB2/ErbB3 oncogenic unit and inhibits heregulin-induced activation of ErbB3," Mol. Cancer Ther. Mar. 2012;11(3):582-93.

Jones PT, et al., "Replacing the complementarity-determining regions in a human antibody with those from a mouse," Nature. May 39, 1986-Jun. 4;321(6069):522-525.

Verhoeyen et al.,. "Reshaping human antibodies: grafting an antilysozyme activity," Science. Mar. 25, 1988;239(4847):1534-6.

Kabat EA, et al. "Identical V region amino acid sequences and segments of sequences in antibodies of different specificities. Relative contributions of VH and VL genes, minigenes, and complementarity-determining regions to binding of antibody-combining sites," J Immunol. Sep. 1, 1991;147(5):1709-19.

Müller R., "Determination of affinity and specificity of anti-hapten antibodies by competitive radioimmunoassay," Methods Enzymol. 1983;92:589-601.

Jackman J. et al., "Development of a two-part strategy to identify a therapeutic human bispecific antibody that inhibits IgE receptor signaling," J. Biol Chem. Jul. 2, 2010;285(27):20850-9.

Baeuerle PA, et al., "Bispecific T-cell engaging antibodies for cancer therapy," Cancer Res. Jun. 15, 2009;69(12):4941-4. Epub Jun. 9, 2009.

Ill CR, et al., "Design and construction of hybrid immunoglobulin domain with properties of both heavy and light chain variable regions," Protein Eng. Aug. 1997;10(8):949-57.

Holliger et al., "Engineered antibody fragments and the rise of single domains," Nat Biotechnol. Sep. 2005;23(9);1126-36.

Chothia c, et al., "Canonical structures for the hypervariable regions of immunoglobulins." J. Mol Biol. Aug. 20, 1987,196(4):901-17.

Plückthun, A. "Antibodies from *Escherichia coli*." *The Pharmacology of Monoclonal Antibodies*. Springer, Berlin, Heidelberg, 1994. 269-315.

Bolzhauser M., *Immuntherapie der kindlichen ALL: Einfluss eines bispeziHschen CD19\* NKp46-Antikörpers auf die zytotoxische Aktivität von NK-Zellen gegenüber CD19_1hn+-ALL-Blasten pädiatrischer Patienten*. Diss. 2010.

Germain C, et al., "Redirecting NK cells mediated tumor cell lysis by a new recombinant bifunctional protein," Protein Eng Des Sel. Nov. 2008;21(11):665-72.

Chames P, et al., "Bispecific antibodies for cancer therapy: the light at the end of the tunnel?". MAbs Nov.-Dec. 2009:1(6):539-547.

Kellner C, et al., "Heterodimeric bispecific antibody-derivatives against CD19 and CD16 induce effective antibody-dependent cellular cytotoxicity against B-lymphoid tumor cells," Cancer Lett. Apr. 28, 2011;303(2):128-39.

Pessino A, et al., "Molecular cloning of NKp46: a novel member of the immunoglobulin superfamily involved in triggering of natural cytotoxicity," J Exp Med. Sep. 7, 1998;188(5):953-60.

Sivori S, et al., "NKp46 is the major triggering receptor involved in the natural cytotoxicity of fresh or cultured human NK cells. Correlation between surface density of NKp46 and natural cytotoxicity against autologous, allogeneic or xenogeneic target cells," Eur J Immunol. May 1999;29(5):1656-66.

Brando C, et al., "Receptors and lytic mediators regulating antitumor activity by the leukemic killer T cell line TALL-104," J Leukocyte Biol. Aug. 2005;78(2):359-71.

El-Sherbiny YM, et al., "The requirement for DNAM-1, NKG2D, and NKp46 in the natural killer cell-mediated killing of myeloma cells," Cancer Res. Sep. 15, 2007;67(18):8444-9.

Nolte EN, et al., "Increased surveillance of cells in mitosis by human NK cells suggests a novel strategy for limiting tumor growth and viral replication," Blood. Jan. 15, 2007;109(2):670-3.

Schleinitz N, et al., "Expression of the CD85j (leukocyte Ig-like receptor 1, Ig-like transcript 2) receptor for class I major histocompatibility complex molecules in idiopathic inflammatory myopathies,"

(56) References Cited

OTHER PUBLICATIONS

Arthritis & Rheum.: Official Journal of the American College of Rheumatology. Oct. 2008;58(10):3216-23.

Umaña P, et al., "Engineered glycoforms of an antineuroblastoma IgG1 with optimized antibody-dependent cellular cytotoxic activity," Nat Biotechnol. Feb. 1999;17(2):176.

Jaron-Mendelson M, et al., "Dimerization of NKp46 receptor is essential for NKp46-mediated lysis: characterization of the dimerization site by epitope mapping," J Immunol. Jun. 15, 2012;188(12):6165-74.

Communication from the International Searching Authority received in PCT/EP2016/064537 dated Sep. 7, 2016.

Holmes TD, et al. "A human NK cell activation/inhibition threshold allows small changes in the target cell surface phenotype to dramatically alter susceptibility to NK cells," The J Immunol. Feb. 1, 2011;186(3): 1538-45.

Kim HR, et al. "Anti-cancer activity and mechanistic features of a NK cell activating molecule," Cancer Immunology, Immunother. Oct. 2009;58(10):1691-700.

Torres and Casadevall. "The immunoglobulin constant region contributes to affinity and specificity," Trends Immunol. Feb. 2008;29(2):91-7.

Vyas M, et al. "Natural ligands and antibody-based fusion proteins: harnessing the immune system against cancer," Trends Mol Med. Feb. 2014;20(2):72-82.

Weidle UH, et al. "The intriguing options of multispecific antibody formats for treatment of cancer," Cancer Genomics-Proteomics. Jan. 1, 2013:10(1):1-18.

Weiner GJ. Rituximab: mechanism of action, Semin Hematol. Apr. 2010;47(2)115-23.

Chung S, et al. "Quantitative evaluation of fucose reducing effects in a humanized antibody on Fcγ receptor binding and antibody-dependent cell-mediated cytotoxicity activities," MAbs May-Jun. 2012;4(3):326-340.

Barb AW, et al. "NMR analysis demonstrates immunoglobulin G N-glycans are accessible and dynamic," Nat Chem Biol. Mar. 2011;7(3):147-153.

* cited by examiner

Figure 6B
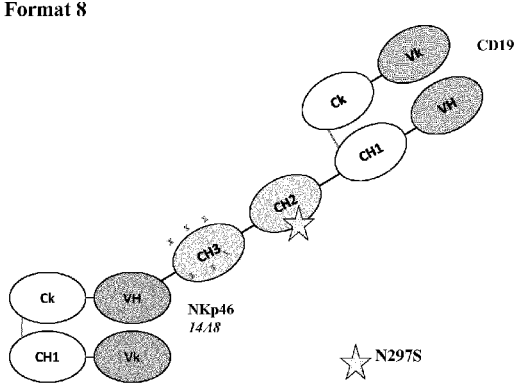
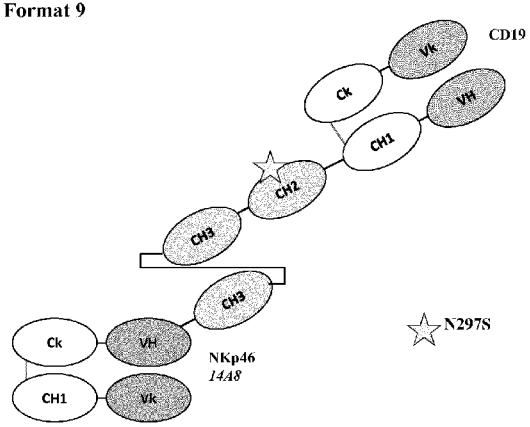
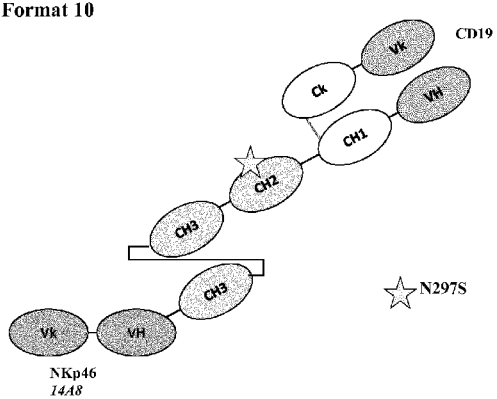

Figure 6C
Format 11
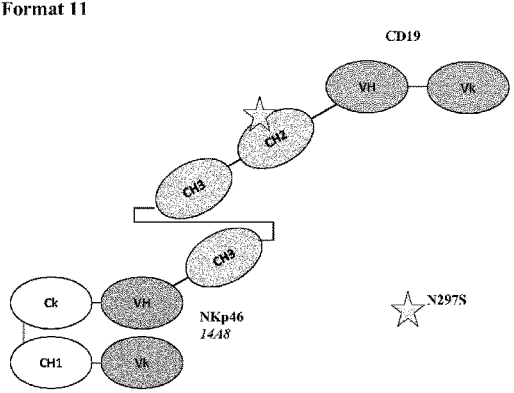
Format 12
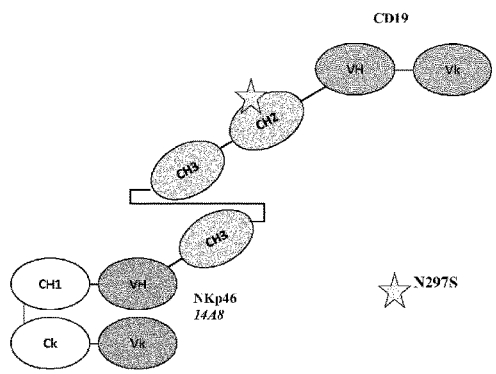
Format 17
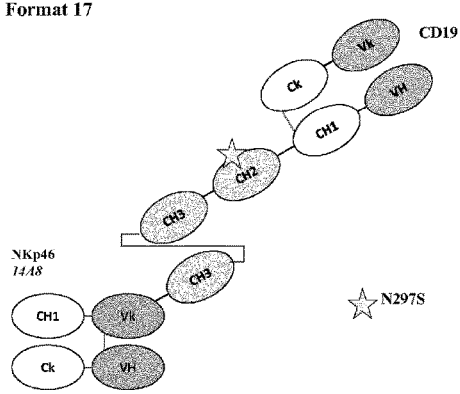

Figure 6D
Format 5
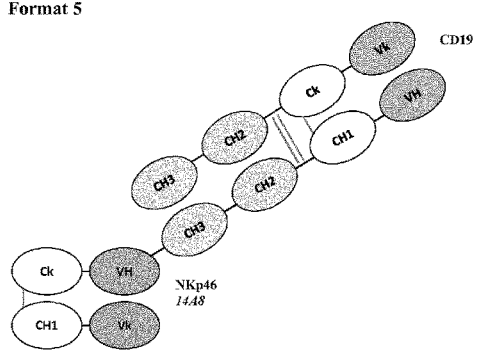
Format 6
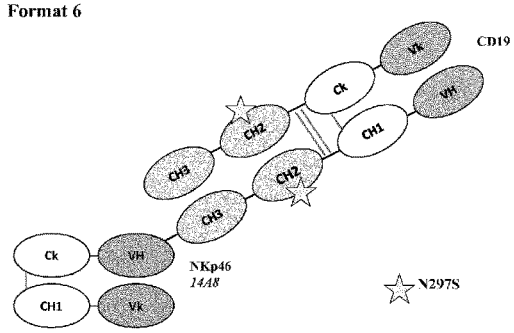
Format 7
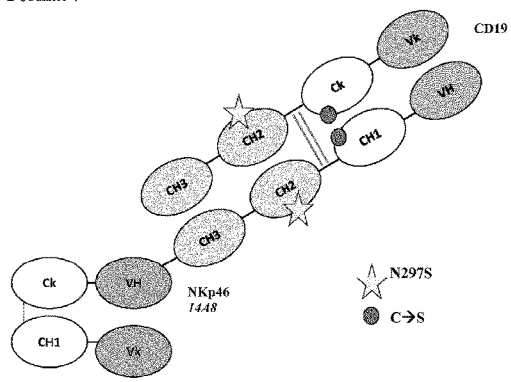
Format 13
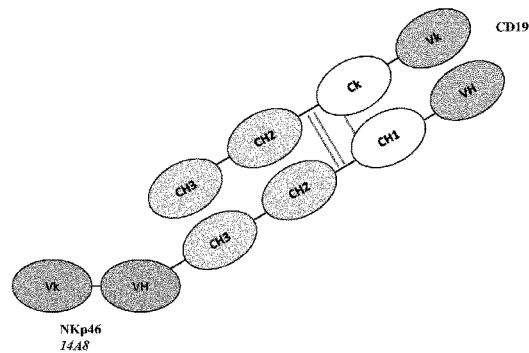

Figure 6E
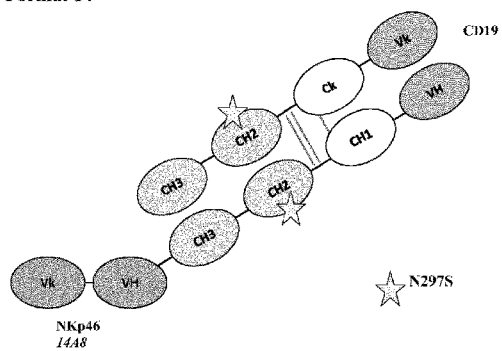
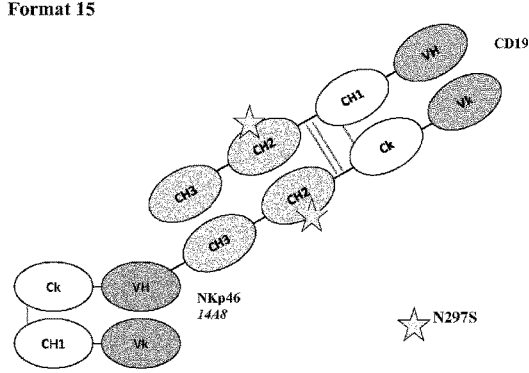
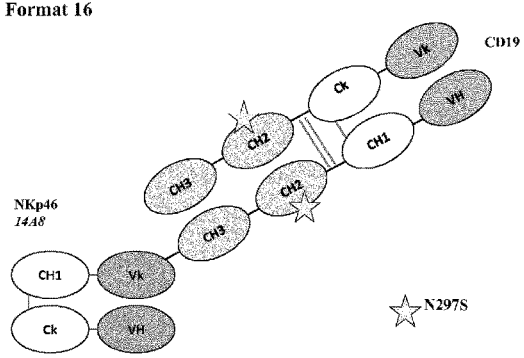

Figure 8A
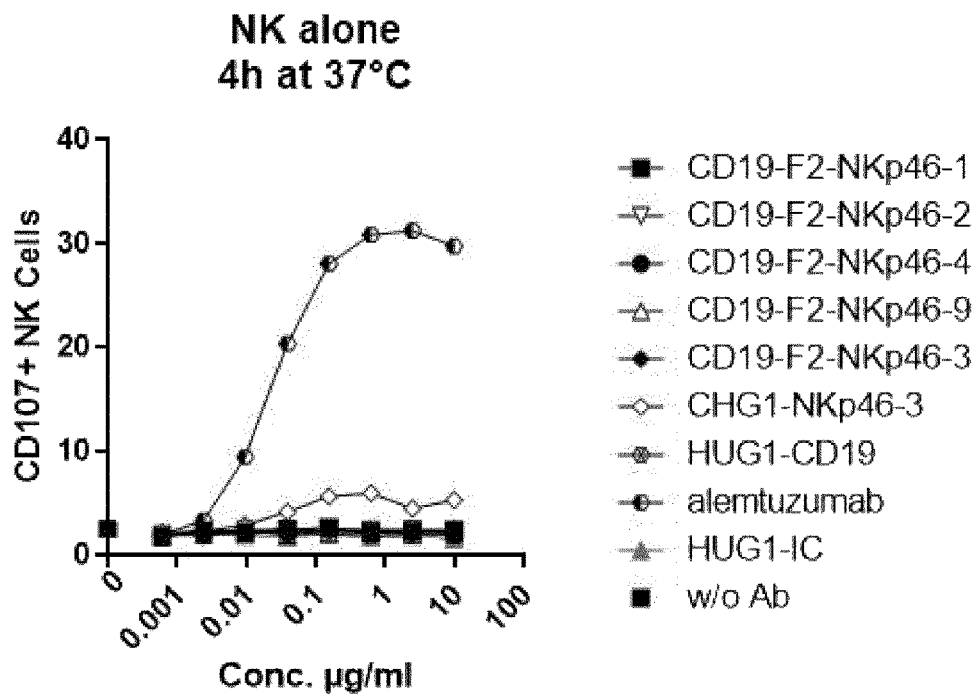
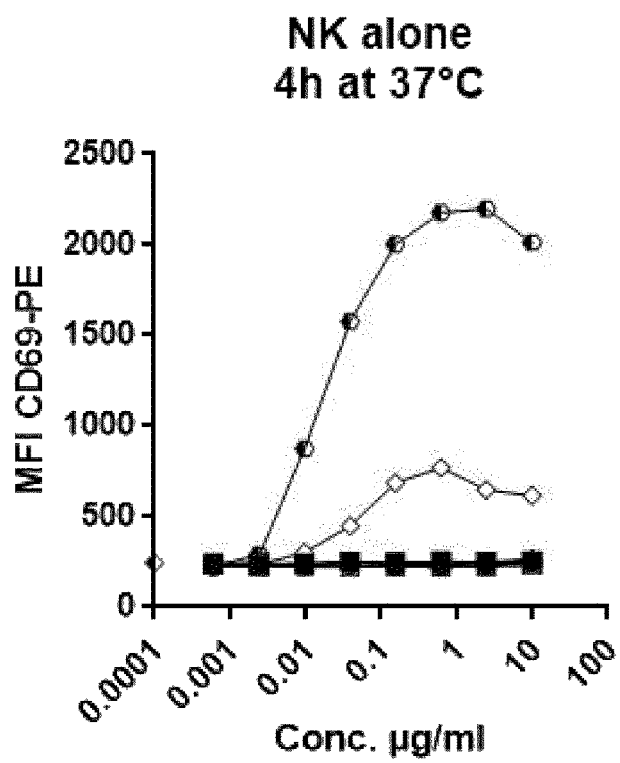

Figure 8B
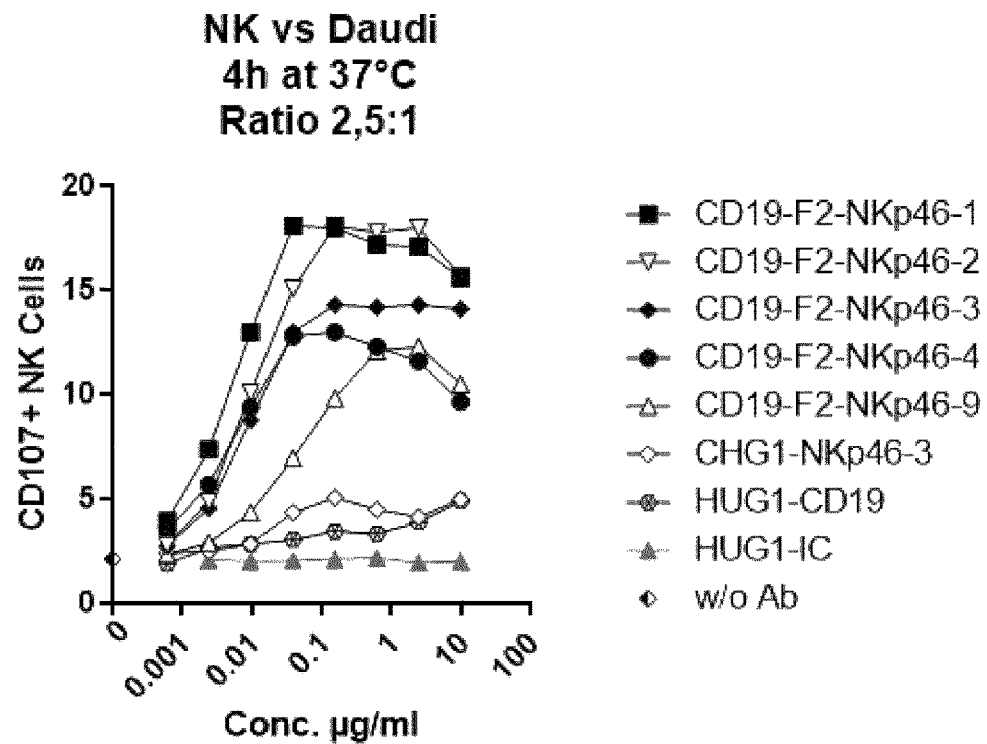
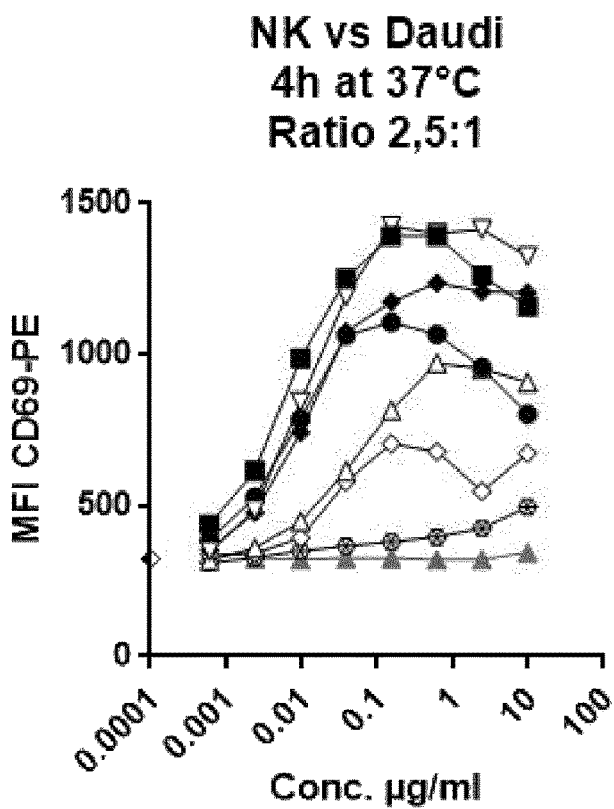

Figure 8C
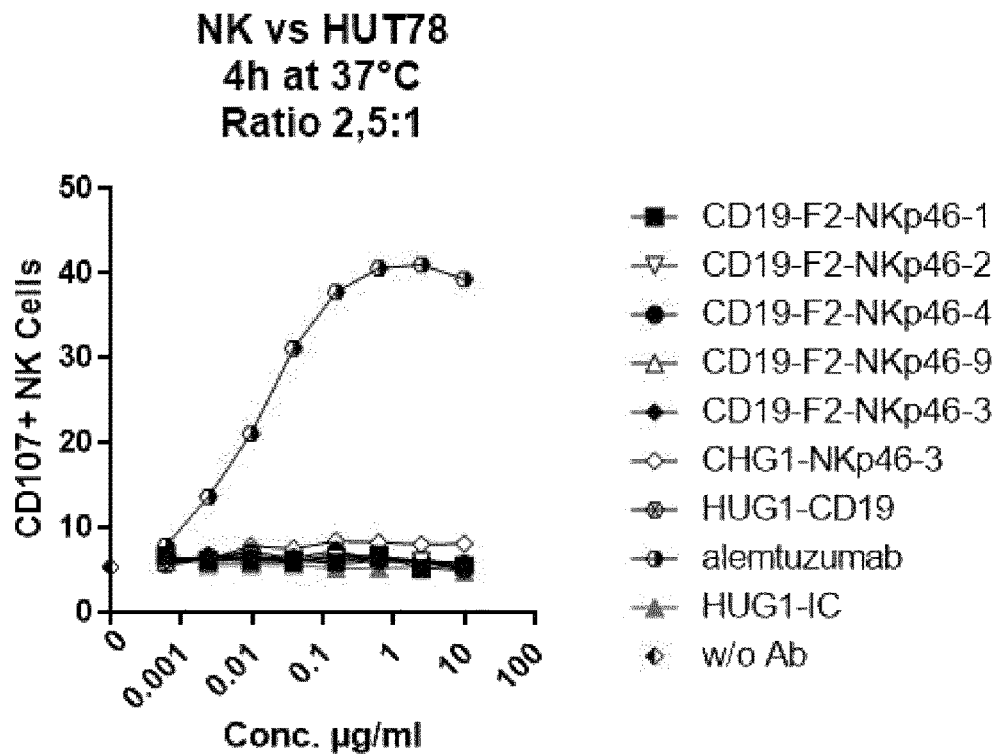
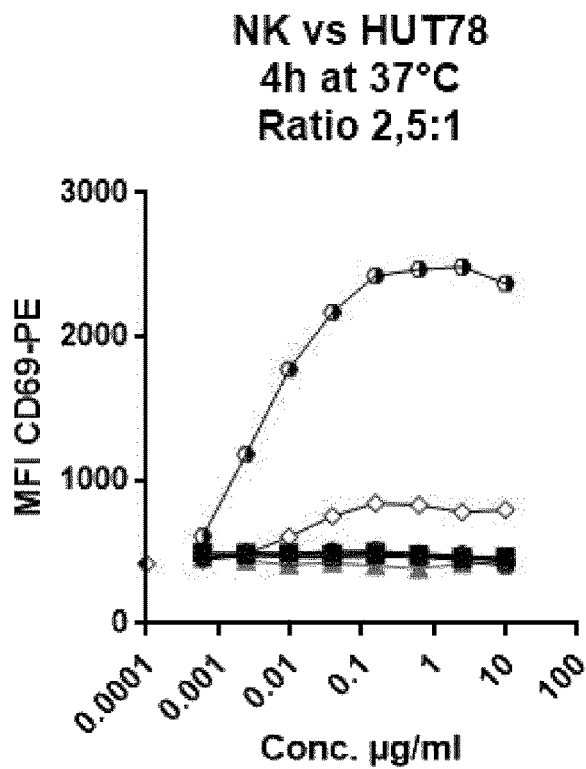

Figure 9
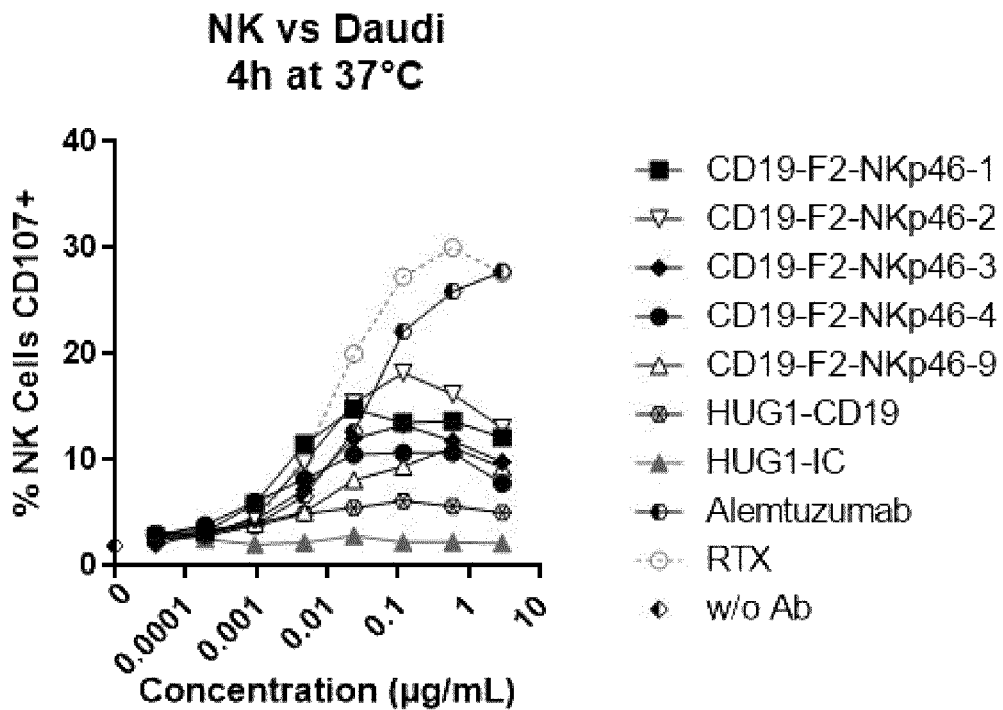
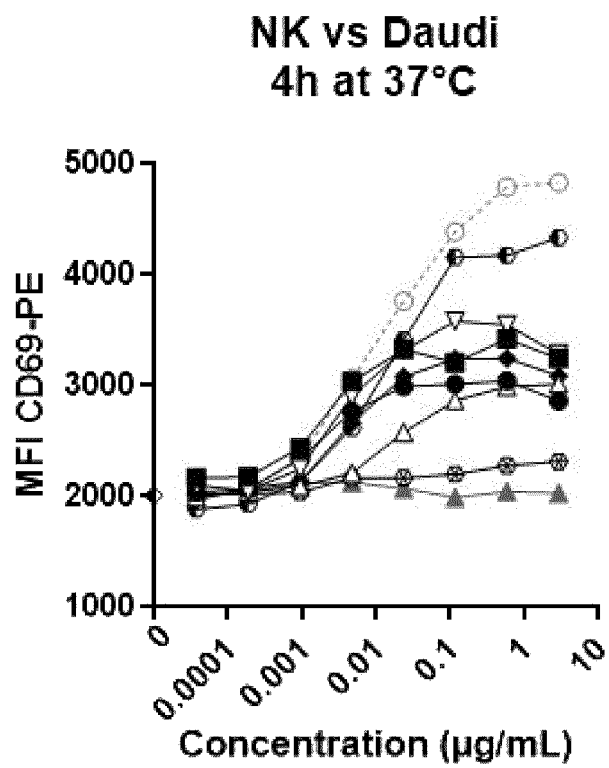

SEQUENCE LISTING

<160> NUMBER OF SEQ ID NOS: 56

<210> SEQ ID NO 1
<211> LENGTH: 216
<212> TYPE: PRT
<213> ORGANISM: Homo sapiens

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Thr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 2
<211> LENGTH: 227
<212> TYPE: PRT
<213> ORGANISM: Homo sapiens

<400> SEQUENCE: 2

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Gly Gly Gly Ser Gly
            100                 105                 110

Gly Gly Gly Ser Gly Gly Gly Ser Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225

<210> SEQ ID NO 3
<211> LENGTH: 333
<212> TYPE: DNA
<213> ORGANISM: mus musculus

<400> SEQUENCE: 3

```
gacattcagc tgacccaatc tccagcttct ttggctgtgt ctctagggca gagggccacc    60
atctcctgca aggccagcca agtgttgat tatgatggtg atagttattt gaactggtac   120
caacagatac caggacagcc acccaaactc ctcatctatg atgcatccaa tctagtatct   180
gggattccac ccaggtttag tggcagtggg tctgggacag acttcaccct caacatccat   240
cctgtggaga aggtggatgc tgcaacctat cactgtcagc aaagtactga ggacccttgg   300
acgttcggtg aggcaccaa gctggaaatc aaa                                 333
```

<210> SEQ ID NO 4
<211> LENGTH: 111
<212> TYPE: PRT
<213> ORGANISM: mus musculus

<400> SEQUENCE: 4

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 5
<211> LENGTH: 372
<212> TYPE: DNA
<213> ORGANISM: mus musculus

<400> SEQUENCE: 5

```
caggttcagc tgcagcagtc tggggctgag ctggtgcggc ctgggtcctc agtgaagatt    60
tcctgcaaag catctggcta cgcattcagt agctactgga tgaactgggt gaagcagagg   120
cctggacagg gtcttgagtg gattggacag atttggcctg agatggtga tactaactac   180 aacggaaagt tcaagggcaa ggccacactg actgcagacg aatcctccag cacagcctac   240
atgcagctca gcagcctggc ctctgaggac tctgcggtct atttctgtgc aagacgagaa   300
acgaccactg tcgggcgtta ttactatgct atggactact ggggtcaagg aaccacagtc   360
accgtctcct ca                                                       372
```

<210> SEQ ID NO 6
<211> LENGTH: 124
<212> TYPE: PRT
<213> ORGANISM: mus musculus

<400> SEQUENCE: 6

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile

```
                   35                  40                  45

Gly Gln Ile Trp Pro Gly Asp Gly Asp Thr Asn Tyr Asn Lys Phe
        50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
            115                 120

<210> SEQ ID NO 7
<211> LENGTH: 648
<212> TYPE: DNA
<213> ORGANISM: homo sapiens

<400> SEQUENCE: 7
gcacctgaac tcctgggggg accgtcagtc ttcctcttcc ccccaaaacc caaggacacc      60
ctcatgatct cccggacccc tgaggtcaca tgcgtggtgg tggacgtgag ccacgaagac     120
cctgaggtca agttcaactg gtacgtggac ggcgtggagg tgcataatgc caagacaaag     180
ccgcgggagg agcagtacaa cagcacgtac cgtgtggtca gcgtcctcac cgtcctgcac     240
caggactggc tgaatggcaa ggagtacaag tgcaaggtct ccaacaaagc cctcccagcc     300
cccatcgaga aaaccatctc caaagccaaa gggcagcccc gagaaccaca ggtgtacacc     360 aagccccat cccgggagga gatgaccaag aaccaggtca gcctgtcctg cctggtcaaa      420
ggcttctatc ccagcgacat cgccgtggag tgggagagca atgggcagcc ggagaacaac     480
tacaagacca cggttcccgt gctggactcc gacggctcct tccgcctcgc tagctacctc     540
accgtggaca agagcaggtg gcagcagggg aacgtcttct catgctccgt gatgcatgag     600
gctctgcaca accactacac gcagaagagc ctctcccctgt ccccgggg                 648

<210> SEQ ID NO 8
<211> LENGTH: 216
<212> TYPE: PRT
<213> ORGANISM: homo sapiens

<400> SEQUENCE: 8

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Lys Pro Pro Ser Arg Glu Glu Met
        115                 120                 125
```

```
Thr Lys Asn Gln Val Ser Leu Ser Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Val Pro Val Leu Asp Ser Asp Gly Ser Phe Arg Leu
                165                 170                 175

Ala Ser Tyr Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 9
<211> LENGTH: 718
<212> TYPE: PRT
<213> ORGANISM: Artificial
<220> FEATURE:
<223> OTHER INFORMATION: Chimeric homo sapiens-mus musculus

<400> SEQUENCE: 9

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Thr Ala Tyr Met Gln Leu
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270
```

-continued

Lys Asp Thr Leu Met Ile Ser Arg Thr Pro Glu Val Thr Cys Val Val
            275                 280                 285
Val Asp Val Ser His Glu Asp Pro Glu Val Lys Phe Asn Trp Tyr Val
    290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
        355                 360                 365
Arg Glu Pro Gln Val Tyr Thr Lys Pro Pro Ser Arg Glu Glu Met Thr
    370                 375                 380
Lys Asn Gln Val Ser Leu Ser Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Val Pro Val Leu Asp Ser Asp Gly Ser Phe Arg Leu Ala
            420                 425                 430
Ser Tyr Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
    450                 455                 460
Ser Leu Ser Leu Ser Pro Gly Ser Thr Gly Ser Asp Ile Lys Leu Gln
465                 470                 475                 480
Gln Ser Gly Ala Glu Leu Ala Arg Pro Gly Ala Ser Val Lys Met Ser
                485                 490                 495
Cys Lys Thr Ser Gly Tyr Thr Phe Thr Arg Tyr Thr Met His Trp Val
            500                 505                 510
Lys Gln Arg Pro Gly Gln Gly Leu Glu Trp Ile Gly Tyr Ile Asn Pro
        515                 520                 525
Ser Arg Gly Tyr Thr Asn Tyr Asn Gln Lys Phe Lys Asp Lys Ala Thr
    530                 535                 540
Leu Thr Thr Asp Lys Ser Ser Ser Thr Ala Tyr Met Gln Leu Ser Ser
545                 550                 555                 560
Leu Thr Ser Glu Asp Ser Ala Val Tyr Tyr Cys Ala Arg Tyr Tyr Asp
                565                 570                 575
Asp His Tyr Cys Leu Asp Tyr Trp Gly Gln Gly Thr Thr Leu Thr Val
            580                 585                 590
Ser Ser Val Glu Gly Gly Ser Gly Gly Ser Gly Gly Ser Gly Gly Ser
        595                 600                 605
Gly Gly Val Asp Asp Ile Gln Leu Thr Gln Ser Pro Ala Ile Met Ser
    610                 615                 620
Ala Ser Pro Gly Glu Lys Val Thr Met Thr Cys Arg Ala Ser Ser Ser
625                 630                 635                 640
Val Ser Tyr Met Asn Trp Tyr Gln Gln Lys Ser Gly Thr Ser Pro Lys
                645                 650                 655
Arg Trp Ile Tyr Asp Thr Ser Lys Val Ala Ser Gly Val Pro Tyr Arg
            660                 665                 670
Phe Ser Gly Ser Gly Ser Gly Thr Ser Tyr Ser Leu Thr Ile Ser Ser
        675                 680                 685
Met Glu Ala Glu Asp Ala Ala Thr Tyr Tyr Cys Gln Gln Trp Ser Ser

```
                    690                 695                 700
Asn Pro Leu Thr Phe Gly Ala Gly Thr Lys Leu Glu Leu Lys
705                 710                 715

<210> SEQ ID NO 10
<211> LENGTH: 245
<212> TYPE: PRT
<213> ORGANISM: Mus musculus

<400> SEQUENCE: 10

Ser Thr Gly Ser Glu Val Gln Leu Gln Gln Ser Gly Pro Glu Leu Val
1               5                   10                  15

Lys Pro Gly Ala Ser Val Lys Ile Ser Cys Lys Thr Ser Gly Tyr Thr
            20                  25                  30

Phe Thr Glu Tyr Thr Met His Trp Val Lys Gln Ser His Gly Lys Ser
        35                  40                  45

Leu Glu Trp Ile Gly Gly Ile Ser Pro Asn Ile Gly Gly Thr Ser Tyr
    50                  55                  60

Asn Gln Lys Phe Lys Gly Lys Ala Thr Leu Thr Val Asp Lys Ser Ser
65                  70                  75                  80

Ser Thr Ala Tyr Met Glu Leu Arg Ser Leu Thr Ser Glu Asp Ser Ala
                85                  90                  95

Val Tyr Tyr Cys Ala Arg Arg Gly Gly Ser Phe Asp Tyr Trp Gly Gln
            100                 105                 110

Gly Thr Thr Leu Thr Val Ser Ser Val Glu Gly Gly Ser Gly Gly Ser
        115                 120                 125

Gly Gly Ser Gly Gly Ser Gly Val Asp Asp Ile Val Met Thr Gln
    130                 135                 140

Ser Pro Ala Thr Leu Ser Val Thr Pro Gly Asp Arg Val Ser Leu Ser
145                 150                 155                 160

Cys Arg Ala Ser Gln Ser Ile Ser Asp Tyr Leu His Trp Tyr Gln Gln
                165                 170                 175

Lys Ser His Glu Ser Pro Arg Leu Leu Ile Lys Tyr Ala Ser Gln Ser
            180                 185                 190

Ile Ser Gly Ile Pro Ser Arg Phe Ser Gly Ser Gly Ser Gly Ser Asp
        195                 200                 205

Phe Thr Leu Ser Ile Asn Ser Val Glu Pro Glu Asp Val Gly Val Tyr
    210                 215                 220

Tyr Cys Gln Asn Gly His Ser Phe Pro Leu Thr Phe Gly Ala Gly Thr
225                 230                 235                 240

Lys Leu Glu Leu Lys
                245

<210> SEQ ID NO 11
<211> LENGTH: 698
<212> TYPE: PRT
<213> ORGANISM: Artificial
<220> FEATURE:
<223> OTHER INFORMATION: Chimeric homo sapiens - mus musculus

<400> SEQUENCE: 11

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45
```

```
Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Lys Pro Pro Ser Arg Glu Glu Met Thr
    370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460
```

```
Ser Leu Ser Leu Ser Pro Gly Ser Thr Gly Ser Glu Val Gln Leu Gln
465                 470                 475                 480

Gln Ser Gly Pro Glu Leu Val Lys Pro Gly Ala Ser Val Lys Ile Ser
            485                 490                 495

Cys Lys Thr Ser Gly Tyr Thr Phe Thr Glu Tyr Thr Met His Trp Val
            500                 505                 510

Lys Gln Ser His Gly Lys Ser Leu Glu Trp Ile Gly Ile Ser Pro
            515                 520                 525

Asn Ile Gly Gly Thr Ser Tyr Asn Gln Lys Phe Lys Gly Lys Ala Thr
            530                 535                 540

Leu Thr Val Asp Lys Ser Ser Thr Ala Tyr Met Glu Leu Arg Ser
545                 550                 555                 560

Leu Thr Ser Glu Asp Ser Ala Val Tyr Tyr Cys Ala Arg Arg Gly Gly
                565                 570                 575

Ser Phe Asp Tyr Trp Gly Gln Gly Thr Thr Leu Thr Val Ser Ser Ala
            580                 585                 590

Ser Thr Lys Gly Pro Ser Val Phe Pro Leu Ala Pro Ser Ser Lys Ser
            595                 600                 605

Thr Ser Gly Gly Thr Ala Ala Leu Gly Cys Leu Val Lys Asp Tyr Phe
            610                 615                 620

Pro Glu Pro Val Thr Val Ser Trp Asn Ser Gly Ala Leu Thr Ser Gly
625                 630                 635                 640

Val His Thr Phe Pro Ala Val Leu Gln Ser Ser Gly Leu Tyr Ser Leu
                645                 650                 655

Ser Ser Val Val Thr Val Pro Ser Ser Ser Leu Gly Thr Gln Thr Tyr
                660                 665                 670

Ile Cys Asn Val Asn His Lys Pro Ser Asn Thr Lys Val Asp Lys Arg
            675                 680                 685

Val Glu Pro Lys Ser Cys Asp Lys Thr His
            690                 695

<210> SEQ ID NO 12
<211> LENGTH: 214
<212> TYPE: PRT
<213> ORGANISM: Artificial
<220> FEATURE:
<223> OTHER INFORMATION: Chimeric - homo sapiens mus musculus

<400> SEQUENCE: 12

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
            50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125
```

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 13

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 14
<211> LENGTH: 675
<212> TYPE: PRT
<213> ORGANISM: Artificial
<220> FEATURE:
<223> OTHER INFORMATION: Chimeric homo sapiens mus musculus

<400> SEQUENCE: 14

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
            85                  90                  95

Ala Arg Arg Glu Thr Thr Thr Val Gly Arg Tyr Tyr Tyr Ala Met Asp
        100                 105                 110

Tyr Trp Gly Gln Gly Thr Thr Val Thr Val Ser Ser Ala Ser Thr Lys
    115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
    210                 215                 220

Lys Ser Cys Gly Gly Gly Ser Ser Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Ser Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Lys Pro Pro Ser Arg Glu Glu Met Thr Lys Asn Gln Val Ser Leu Ser
    355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Val Pro Val Leu
385                 390                 395                 400

Asp Ser Asp Gly Ser Phe Arg Leu Ala Ser Tyr Leu Thr Val Asp Lys
            405                 410                 415
```

```
Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Ser Thr Gly Ser Glu Val Gln Leu Gln Gln Ser Gly Pro Glu Leu Val
        450                 455                 460

Lys Pro Gly Ala Ser Val Lys Ile Ser Cys Lys Thr Ser Gly Tyr Thr
465                 470                 475                 480

Phe Thr Glu Tyr Thr Met His Trp Val Lys Gln Ser His Gly Lys Ser
                485                 490                 495

Leu Glu Trp Ile Gly Gly Ile Ser Pro Asn Ile Gly Gly Thr Ser Tyr
            500                 505                 510

Asn Gln Lys Phe Lys Gly Lys Ala Thr Leu Thr Val Asp Lys Ser Ser
        515                 520                 525

Ser Thr Ala Tyr Met Glu Leu Arg Ser Leu Thr Ser Glu Asp Ser Ala
530                 535                 540

Val Tyr Tyr Cys Ala Arg Arg Gly Gly Ser Phe Asp Tyr Trp Gly Gln
545                 550                 555                 560

Gly Thr Thr Leu Thr Val Ser Ser Arg Thr Val Ala Ala Pro Ser Val
                565                 570                 575

Phe Ile Phe Pro Pro Ser Asp Glu Gln Leu Lys Ser Gly Thr Ala Ser
            580                 585                 590

Val Val Cys Leu Leu Asn Asn Phe Tyr Pro Arg Glu Ala Lys Val Gln
        595                 600                 605

Trp Lys Val Asp Asn Ala Leu Gln Ser Gly Asn Ser Gln Glu Ser Val
610                 615                 620

Thr Glu Gln Asp Ser Lys Asp Ser Thr Tyr Ser Leu Ser Ser Thr Leu
625                 630                 635                 640

Thr Leu Ser Lys Ala Asp Tyr Glu Lys His Lys Val Tyr Ala Cys Glu
                645                 650                 655

Val Thr His Gln Gly Leu Ser Ser Pro Val Thr Lys Ser Phe Asn Arg
            660                 665                 670

Gly Glu Cys
        675

<210> SEQ ID NO 15
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 15

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95
```

```
Thr Phe Gly Ala Gly Thr Lys Leu Glu Leu Lys Ala Ser Thr Lys Gly
                100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210
```

<210> SEQ ID NO 16
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 16

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 17
<211> LENGTH: 801

```
<212> TYPE: PRT
<213> ORGANISM: Artificial
<220> FEATURE:
<223> OTHER INFORMATION: Chimeric homo sapiens mus musculus

<400> SEQUENCE: 17
```

| | | | | | | | | | | | | | | | |
|---|---|---|---|---|---|---|---|---|---|---|---|---|---|---|---|
| Gln | Val | Gln | Leu | Gln | Gln | Ser | Gly | Ala | Glu | Leu | Val | Arg | Pro | Gly | Ser |
| 1 | | | | 5 | | | | | 10 | | | | | 15 | |
| Ser | Val | Lys | Ile | Ser | Cys | Lys | Ala | Ser | Gly | Tyr | Ala | Phe | Ser | Ser | Tyr |
| | | | 20 | | | | | 25 | | | | | 30 | | |
| Trp | Met | Asn | Trp | Val | Lys | Gln | Arg | Pro | Gly | Gln | Gly | Leu | Glu | Trp | Ile |
| | | 35 | | | | | 40 | | | | | 45 | | | |
| Gly | Gln | Ile | Trp | Pro | Gly | Asp | Gly | Asp | Thr | Asn | Tyr | Asn | Gly | Lys | Phe |
| 50 | | | | | 55 | | | | | 60 | | | | | |
| Lys | Gly | Lys | Ala | Thr | Leu | Thr | Ala | Asp | Glu | Ser | Ser | Ser | Thr | Ala | Tyr |
| 65 | | | | | 70 | | | | | 75 | | | | | 80 |
| Met | Gln | Leu | Ser | Ser | Leu | Ala | Ser | Glu | Asp | Ser | Ala | Val | Tyr | Phe | Cys |
| | | | | 85 | | | | | 90 | | | | | 95 | |
| Ala | Arg | Arg | Glu | Thr | Thr | Thr | Val | Gly | Arg | Tyr | Tyr | Tyr | Ala | Met | Asp |
| | | | 100 | | | | | 105 | | | | | 110 | | |
| Tyr | Trp | Gly | Gln | Gly | Thr | Thr | Val | Thr | Val | Ser | Ser | Ala | Ser | Thr | Lys |
| | | 115 | | | | | 120 | | | | | 125 | | | |
| Gly | Pro | Ser | Val | Phe | Pro | Leu | Ala | Pro | Ser | Ser | Lys | Ser | Thr | Ser | Gly |
| 130 | | | | | 135 | | | | | 140 | | | | | |
| Gly | Thr | Ala | Ala | Leu | Gly | Cys | Leu | Val | Lys | Asp | Tyr | Phe | Pro | Glu | Pro |
| 145 | | | | | 150 | | | | | 155 | | | | | 160 |
| Val | Thr | Val | Ser | Trp | Asn | Ser | Gly | Ala | Leu | Thr | Ser | Gly | Val | His | Thr |
| | | | | 165 | | | | | 170 | | | | | 175 | |
| Phe | Pro | Ala | Val | Leu | Gln | Ser | Ser | Gly | Leu | Tyr | Ser | Leu | Ser | Ser | Val |
| | | | 180 | | | | | 185 | | | | | 190 | | |
| Val | Thr | Val | Pro | Ser | Ser | Ser | Leu | Gly | Thr | Gln | Thr | Tyr | Ile | Cys | Asn |
| | | 195 | | | | | 200 | | | | | 205 | | | |
| Val | Asn | His | Lys | Pro | Ser | Asn | Thr | Lys | Val | Asp | Lys | Arg | Val | Glu | Pro |
| 210 | | | | | 215 | | | | | 220 | | | | | |
| Lys | Ser | Cys | Asp | Lys | Thr | His | Thr | Cys | Pro | Pro | Cys | Pro | Ala | Pro | Glu |
| 225 | | | | | 230 | | | | | 235 | | | | | 240 |
| Leu | Leu | Gly | Gly | Pro | Ser | Val | Phe | Leu | Phe | Pro | Pro | Lys | Pro | Lys | Asp |
| | | | | 245 | | | | | 250 | | | | | 255 | |
| Thr | Leu | Met | Ile | Ser | Arg | Thr | Pro | Glu | Val | Thr | Cys | Val | Val | Val | Asp |
| | | | 260 | | | | | 265 | | | | | 270 | | |
| Val | Ser | His | Glu | Asp | Pro | Glu | Val | Lys | Phe | Asn | Trp | Tyr | Val | Asp | Gly |
| | | 275 | | | | | 280 | | | | | 285 | | | |
| Val | Glu | Val | His | Asn | Ala | Lys | Thr | Lys | Pro | Arg | Glu | Glu | Gln | Tyr | Ser |
| 290 | | | | | 295 | | | | | 300 | | | | | |
| Ser | Thr | Tyr | Arg | Val | Val | Ser | Val | Leu | Thr | Val | Leu | His | Gln | Asp | Trp |
| 305 | | | | | 310 | | | | | 315 | | | | | 320 |
| Leu | Asn | Gly | Lys | Glu | Tyr | Lys | Cys | Lys | Val | Ser | Asn | Lys | Ala | Leu | Pro |
| | | | | 325 | | | | | 330 | | | | | 335 | |
| Ala | Pro | Ile | Glu | Lys | Thr | Ile | Ser | Lys | Ala | Lys | Gly | Gln | Pro | Arg | Glu |
| | | | 340 | | | | | 345 | | | | | 350 | | |
| Pro | Gln | Val | Tyr | Thr | Leu | Pro | Pro | Ser | Arg | Glu | Glu | Met | Thr | Lys | Asn |
| | | 355 | | | | | 360 | | | | | 365 | | | |
| Gln | Val | Ser | Leu | Thr | Cys | Leu | Val | Lys | Gly | Phe | Tyr | Pro | Ser | Asp | Ile |
| 370 | | | | | 375 | | | | | 380 | | | | | |

```
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Gly Gly Gly Ser Gly Gly Gly Gly Ser Gly
        450                 455                 460

Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
            485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
            515                 520                 525

Asp Gly Ser Phe Phe Leu Tyr Ser Lys Leu Thr Val Asp Lys Ser Arg
530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
            565                 570                 575

Gly Ser Glu Val Gln Leu Gln Gln Ser Gly Pro Glu Leu Val Lys Pro
            580                 585                 590

Gly Ala Ser Val Lys Ile Ser Cys Lys Thr Ser Gly Tyr Thr Phe Thr
            595                 600                 605

Glu Tyr Thr Met His Trp Val Lys Gln Ser His Gly Lys Ser Leu Glu
            610                 615                 620

Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
            645                 650                 655

Ala Tyr Met Glu Leu Arg Ser Leu Thr Ser Glu Asp Ser Ala Val Tyr
            660                 665                 670

Tyr Cys Ala Arg Arg Gly Gly Ser Phe Asp Tyr Trp Gly Gln Gly Thr
            675                 680                 685

Thr Leu Thr Val Ser Ser Arg Thr Val Ala Ala Pro Ser Val Phe Ile
            690                 695                 700

Phe Pro Pro Ser Asp Glu Gln Leu Lys Ser Gly Thr Ala Ser Val Val
705                 710                 715                 720

Cys Leu Leu Asn Asn Phe Tyr Pro Arg Glu Ala Lys Val Gln Trp Lys
            725                 730                 735

Val Asp Asn Ala Leu Gln Ser Gly Asn Ser Gln Glu Ser Val Thr Glu
            740                 745                 750

Gln Asp Ser Lys Asp Ser Thr Tyr Ser Leu Ser Ser Thr Leu Thr Leu
            755                 760                 765

Ser Lys Ala Asp Tyr Glu Lys His Lys Val Tyr Ala Cys Glu Val Thr
            770                 775                 780

His Gln Gly Leu Ser Ser Pro Val Thr Lys Ser Phe Asn Arg Gly Glu
785                 790                 795                 800

Cys
```

<210> SEQ ID NO 18
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 18

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 19
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 19

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr

```
                         85                  90                  95
Glu Asp Pro Trp Thr Phe Gly Gly Thr Lys Leu Glu Ile Lys Arg
                100                 105                 110

Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 20
<211> LENGTH: 801
<212> TYPE: PRT
<213> ORGANISM: Artificial
<220> FEATURE:
<223> OTHER INFORMATION: Chimeric homo sapiens mus musculus

<400> SEQUENCE: 20

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Val Gly Arg Tyr Tyr Ala Met Asp
                100                 105                 110

Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Cys Asp Lys Thr His Thr Ser Pro Pro Ser Pro Ala Pro Glu
```

```
             225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Ser
                290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Gly Gly Gly Ser Gly Gly Gly Gly Ser Gly
                450                 455                 460

Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
                500                 505                 510

Gly Gln Pro Glu Asn Asn Tyr Lys Thr Thr Pro Pro Val Leu Asp Ser
                515                 520                 525

Asp Gly Ser Phe Phe Leu Tyr Ser Lys Leu Thr Val Asp Lys Ser Arg
                530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Glu Val Gln Leu Gln Gln Ser Gly Pro Glu Leu Val Lys Pro
                580                 585                 590

Gly Ala Ser Val Lys Ile Ser Cys Lys Thr Ser Gly Tyr Thr Phe Thr
                595                 600                 605

Glu Tyr Thr Met His Trp Val Lys Gln Ser His Gly Lys Ser Leu Glu
                610                 615                 620

Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
                645                 650                 655
```

Ala Tyr Met Glu Leu Arg Ser Leu Thr Ser Glu Asp Ser Ala Val Tyr
                660                 665                 670

Tyr Cys Ala Arg Arg Gly Gly Ser Phe Asp Tyr Trp Gly Gln Gly Thr
            675                 680                 685

Thr Leu Thr Val Ser Ser Arg Thr Val Ala Ala Pro Ser Val Phe Ile
    690                 695                 700

Phe Pro Pro Ser Asp Glu Gln Leu Lys Ser Gly Thr Ala Ser Val Val
705                 710                 715                 720

Cys Leu Leu Asn Asn Phe Tyr Pro Arg Glu Ala Lys Val Gln Trp Lys
                725                 730                 735

Val Asp Asn Ala Leu Gln Ser Gly Asn Ser Gln Glu Ser Val Thr Glu
            740                 745                 750

Gln Asp Ser Lys Asp Ser Thr Tyr Ser Leu Ser Ser Thr Leu Thr Leu
    755                 760                 765

Ser Lys Ala Asp Tyr Glu Lys His Lys Val Tyr Ala Cys Glu Val Thr
770                 775                 780

His Gln Gly Leu Ser Ser Pro Val Thr Lys Ser Phe Asn Arg Gly Glu
785                 790                 795                 800

Cys

<210> SEQ ID NO 21
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 21

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 22
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 22

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 23
<211> LENGTH: 796
<212> TYPE: PRT
<213> ORGANISM: Artificial
<220> FEATURE:
<223> OTHER INFORMATION: Chimeric homo sapiens mus musculus

<400> SEQUENCE: 23

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

```
Met Gln Leu Ser Ser Leu Ala Ser Glu Asp Ser Ala Val Tyr Phe Cys
                85                  90                  95
Ala Arg Arg Glu Thr Thr Thr Val Gly Arg Tyr Tyr Tyr Ala Met Asp
                100                 105                 110
Tyr Trp Gly Gln Gly Thr Thr Val Thr Val Ser Ser Ala Ser Thr Lys
        115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Ser Leu Gly Thr Gln Thr Tyr Ile Cys Asn
                195                 200                 205
Val Asn His Lys Pro Ser Asn Thr Lys Val Asp Lys Arg Val Glu Pro
210                 215                 220
Lys Ser Cys Gly Gly Ser Ser Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Ser Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Gly Gly Gly Gly Ser Gly Gly Gly Ser Gly Gly Gly Gly Ser Gly
    450                 455                 460
Gln Pro Arg Glu Pro Gln Val Tyr Thr Leu Pro Pro Ser Arg Glu Glu
465                 470                 475                 480
Met Thr Lys Asn Gln Val Ser Leu Thr Cys Leu Val Lys Gly Phe Tyr
                485                 490                 495
```

```
Pro Ser Asp Ile Ala Val Glu Trp Glu Ser Asn Gly Gln Pro Glu Asn
            500                 505                 510

Asn Tyr Lys Thr Thr Pro Val Leu Asp Ser Asp Gly Ser Phe Phe
        515                 520                 525

Leu Tyr Ser Lys Leu Thr Val Asp Lys Ser Arg Trp Gln Gln Gly Asn
    530                 535                 540

Val Phe Ser Cys Ser Val Met His Glu Ala Leu His Asn His Tyr Thr
545                 550                 555                 560

Gln Lys Ser Leu Ser Leu Ser Pro Gly Ser Thr Gly Ser Glu Val Gln
                565                 570                 575

Leu Gln Gln Ser Gly Pro Glu Leu Val Lys Pro Gly Ala Ser Val Lys
            580                 585                 590

Ile Ser Cys Lys Thr Ser Gly Tyr Thr Phe Thr Glu Tyr Thr Met His
        595                 600                 605

Trp Val Lys Gln Ser His Gly Lys Ser Leu Glu Trp Ile Gly Gly Ile
    610                 615                 620

Ser Pro Asn Ile Gly Gly Thr Ser Tyr Asn Gln Lys Phe Lys Gly Lys
625                 630                 635                 640

Ala Thr Leu Thr Val Asp Lys Ser Ser Ser Thr Ala Tyr Met Glu Leu
                645                 650                 655

Arg Ser Leu Thr Ser Glu Asp Ser Ala Val Tyr Tyr Cys Ala Arg Arg
            660                 665                 670

Gly Gly Ser Phe Asp Tyr Trp Gly Gln Gly Thr Thr Leu Thr Val Ser
        675                 680                 685

Ser Arg Thr Val Ala Ala Pro Ser Val Phe Ile Phe Pro Pro Ser Asp
    690                 695                 700

Glu Gln Leu Lys Ser Gly Thr Ala Ser Val Val Cys Leu Leu Asn Asn
705                 710                 715                 720

Phe Tyr Pro Arg Glu Ala Lys Val Gln Trp Lys Val Asp Asn Ala Leu
                725                 730                 735

Gln Ser Gly Asn Ser Gln Glu Ser Val Thr Glu Gln Asp Ser Lys Asp
            740                 745                 750

Ser Thr Tyr Ser Leu Ser Ser Thr Leu Thr Leu Ser Lys Ala Asp Tyr
        755                 760                 765

Glu Lys His Lys Val Tyr Ala Cys Glu Val Thr His Gln Gly Leu Ser
    770                 775                 780

Ser Pro Val Thr Lys Ser Phe Asn Arg Gly Glu Cys
785                 790                 795

<210> SEQ ID NO 24
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 24

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60
```

```
Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 25
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 25

Asp Ile Gln Leu Thr Gln Ser Pro Ala Ser Leu Ala Val Ser Leu Gly
  1               5                  10                  15

Gln Arg Ala Thr Ile Ser Cys Lys Ala Ser Gln Ser Val Asp Tyr Asp
                 20                  25                  30

Gly Asp Ser Tyr Leu Asn Trp Tyr Gln Gln Ile Pro Gly Gln Pro Pro
             35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

```
Val Thr Lys Ser Phe Asn Arg Gly Glu Cys
    210                 215
```

<210> SEQ ID NO 26
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 26

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350
```

Pro Gln Val Tyr Thr Leu Pro Pro Ser Arg Glu Glu Met Thr Lys Asn
             355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Gly Gly Gly Ser Gly Gly Gly Gly Ser Gly
    450                 455                 460

Gly Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Glu Val Gln Leu Gln Gln Ser Gly Pro Glu Leu Val Lys Pro
            580                 585                 590

Gly Ala Ser Val Lys Ile Ser Cys Lys Thr Ser Gly Tyr Thr Phe Thr
        595                 600                 605

Glu Tyr Thr Met His Trp Val Lys Gln Ser His Gly Lys Ser Leu Glu
    610                 615                 620

Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
                645                 650                 655

Ala Tyr Met Glu Leu Arg Ser Leu Thr Ser Glu Asp Ser Ala Val Tyr
            660                 665                 670

Tyr Cys Ala Arg Arg Gly Gly Ser Phe Asp Tyr Trp Gly Gln Gly Thr
        675                 680                 685

Thr Leu Thr Val Ser Ser Val Glu Gly Gly Ser Gly Gly Ser Gly Gly
    690                 695                 700

Ser Gly Gly Ser Gly Gly Val Asp Asp Ile Val Met Thr Gln Ser Pro
705                 710                 715                 720

Ala Thr Leu Ser Val Thr Pro Gly Asp Arg Val Ser Leu Ser Cys Arg
                725                 730                 735

Ala Ser Gln Ser Ile Ser Asp Tyr Leu His Trp Tyr Gln Gln Lys Ser
            740                 745                 750

His Glu Ser Pro Arg Leu Leu Ile Lys Tyr Ala Ser Gln Ser Ile Ser
        755                 760                 765

Gly Ile Pro Ser Arg Phe Ser Gly Ser Gly Ser Gly Ser Asp Phe Thr

```
                    770                 775                 780
Leu Ser Ile Asn Ser Val Glu Pro Glu Asp Val Gly Val Tyr Tyr Cys
785                 790                 795                 800

Gln Asn Gly His Ser Phe Pro Leu Thr Phe Gly Ala Gly Thr Lys Leu
                805                 810                 815

Glu Leu Lys

<210> SEQ ID NO 27
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 27

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 28
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 28

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
```

```
            35                  40                  45
Gly Gln Ile Trp Pro Gly Asp Gly Asp Thr Asn Tyr Asn Gly Lys Phe
 50                  55                  60

Lys Gly Lys Ala Thr Leu Thr Ala Asp Glu Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Ala Met Asp
                100                 105                 110

Tyr Trp Gly Gln Gly Thr Thr Val Thr Val Ser Ser Ala Ser Thr Lys
                115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
210                 215                 220

Lys Ser Cys Asp Lys Thr His Thr Ser Pro Pro Ser Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Ser
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Gly Gly Gly Ser Gly Gly Gly Gly Ser Gly
450                 455                 460
```

Gly Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
            485                 490                 495

Val Lys Gly Phe Tyr Pro Ser Asp Ile Ala Val Glu Trp Glu Ser Asn
        500                 505                 510

Gly Gln Pro Glu Asn Asn Tyr Lys Thr Thr Pro Val Leu Asp Ser
        515                 520                 525

Asp Gly Ser Phe Phe Leu Tyr Ser Lys Leu Thr Val Asp Lys Ser Arg
        530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Glu Val Gln Leu Gln Gln Ser Gly Pro Glu Leu Val Lys Pro
            580                 585                 590

Gly Ala Ser Val Lys Ile Ser Cys Lys Thr Ser Gly Tyr Thr Phe Thr
        595                 600                 605

Glu Tyr Thr Met His Trp Val Lys Gln Ser His Gly Lys Ser Leu Glu
    610                 615                 620

Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
                645                 650                 655

Ala Tyr Met Glu Leu Arg Ser Leu Thr Ser Glu Asp Ser Ala Val Tyr
            660                 665                 670

Tyr Cys Ala Arg Arg Gly Gly Ser Phe Asp Tyr Trp Gly Gln Gly Thr
        675                 680                 685

Thr Leu Thr Val Ser Ser Val Glu Gly Gly Ser Gly Gly Ser Gly Gly
    690                 695                 700

Ser Gly Gly Ser Gly Gly Val Asp Asp Ile Val Met Thr Gln Ser Pro
705                 710                 715                 720

Ala Thr Leu Ser Val Thr Pro Gly Asp Arg Val Ser Leu Ser Cys Arg
                725                 730                 735

Ala Ser Gln Ser Ile Ser Asp Tyr Leu His Trp Tyr Gln Gln Lys Ser
            740                 745                 750

His Glu Ser Pro Arg Leu Leu Ile Lys Tyr Ala Ser Gln Ser Ile Ser
        755                 760                 765

Gly Ile Pro Ser Arg Phe Ser Gly Ser Gly Ser Asp Phe Thr
    770                 775                 780

Leu Ser Ile Asn Ser Val Glu Pro Glu Asp Val Gly Val Tyr Tyr Cys
785                 790                 795                 800

Gln Asn Gly His Ser Phe Pro Leu Thr Phe Gly Ala Gly Thr Lys Leu
                805                 810                 815

Glu Leu Lys

<210> SEQ ID NO 29
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 29

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 30
<211> LENGTH: 815
<212> TYPE: PRT
<213> ORGANISM: Artificial
<220> FEATURE:
<223> OTHER INFORMATION: Chimeric homo sapiens mus musculus

<400> SEQUENCE: 30

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140
```

```
Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Ser Leu Gly Thr Gln Thr Tyr Ile Cys Asn
    195                 200                 205

Val Asn His Lys Pro Ser Asn Thr Lys Val Asp Lys Arg Val Glu Pro
    210                 215                 220

Lys Ser Cys Gly Gly Gly Ser Ser Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ser Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Gly Gly Gly Ser Gly Gly Gly Gly Ser Gly Gly Gly Gly Ser
    450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
            485                 490                 495

Tyr Pro Ser Asp Ile Ala Val Glu Trp Glu Ser Asn Gly Gln Pro Glu
        500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Ser Thr Gly Ser Glu Val
```

```
                     565                 570                 575

Gln Leu Gln Gln Ser Gly Pro Glu Leu Val Lys Pro Gly Ala Ser Val
            580                 585                 590

Lys Ile Ser Cys Lys Thr Ser Gly Tyr Thr Phe Thr Glu Tyr Thr Met
        595                 600                 605

His Trp Val Lys Gln Ser His Gly Lys Ser Leu Glu Trp Ile Gly Gly
    610                 615                 620

Ile Ser Pro Asn Ile Gly Gly Thr Ser Tyr Asn Gln Lys Phe Lys Gly
625                 630                 635                 640

Lys Ala Thr Leu Thr Val Asp Lys Ser Ser Thr Ala Tyr Met Glu
                645                 650                 655

Leu Arg Ser Leu Thr Ser Glu Asp Ser Ala Val Tyr Tyr Cys Ala Arg
            660                 665                 670

Arg Gly Gly Ser Phe Asp Tyr Trp Gly Gln Gly Thr Thr Leu Thr Val
        675                 680                 685

Ser Ser Val Glu Gly Gly Ser Gly Gly Ser Gly Gly Ser
    690                 695                 700

Gly Gly Val Asp Asp Ile Val Met Thr Gln Ser Pro Ala Thr Leu Ser
705                 710                 715                 720

Val Thr Pro Gly Asp Arg Val Ser Leu Ser Cys Arg Ala Ser Gln Ser
                725                 730                 735

Ile Ser Asp Tyr Leu His Trp Tyr Gln Gln Lys Ser His Glu Ser Pro
            740                 745                 750

Arg Leu Leu Ile Lys Tyr Ala Ser Gln Ser Ile Ser Gly Ile Pro Ser
        755                 760                 765

Arg Phe Ser Gly Ser Gly Ser Gly Ser Asp Phe Thr Leu Ser Ile Asn
    770                 775                 780

Ser Val Glu Pro Glu Asp Val Gly Val Tyr Tyr Cys Gln Asn Gly His
785                 790                 795                 800

Ser Phe Pro Leu Thr Phe Gly Ala Gly Thr Lys Leu Glu Leu Lys
                805                 810                 815

<210> SEQ ID NO 31
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 31

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
```

```
                115                 120                 125
Gln Leu Gln Gln Ser Gly Ala Glu Leu Val Arg Pro Gly Ser Ser Val
130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
                180                 185                 190

Lys Ala Thr Leu Thr Ala Asp Glu Ser Ser Ser Thr Ala Tyr Met Gln
                195                 200                 205

Leu Ser Ser Leu Ala Ser Glu Asp Ser Ala Val Tyr Phe Cys Ala Arg
210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Ser Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
450                 455                 460

Ser Leu Ser Leu Ser Pro Gly Gly Gly Gly Ser Gly Gly Gly Gly
465                 470                 475                 480

Ser Gly Gly Gly Gly Ser Gly Gln Pro Arg Glu Pro Gln Val Tyr Thr
                485                 490                 495

Leu Pro Pro Ser Arg Glu Glu Met Thr Lys Asn Gln Val Ser Leu Thr
                500                 505                 510

Cys Leu Val Lys Gly Phe Tyr Pro Ser Asp Ile Ala Val Glu Trp Glu
                515                 520                 525

Ser Asn Gly Gln Pro Glu Asn Asn Tyr Lys Thr Thr Pro Pro Val Leu
530                 535                 540
```

```
Asp Ser Asp Gly Ser Phe Phe Leu Tyr Ser Lys Leu Thr Val Asp Lys
545                 550                 555                 560

Ser Arg Trp Gln Gln Gly Asn Val Phe Ser Cys Ser Val Met His Glu
                565                 570                 575

Ala Leu His Asn His Tyr Thr Gln Lys Ser Leu Ser Leu Ser Pro Gly
            580                 585                 590

Ser Thr Gly Ser Glu Val Gln Leu Gln Gln Ser Gly Pro Glu Leu Val
        595                 600                 605

Lys Pro Gly Ala Ser Val Lys Ile Ser Cys Lys Thr Ser Gly Tyr Thr
    610                 615                 620

Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Gly Thr Ser Tyr
                645                 650                 655

Asn Gln Lys Phe Lys Gly Lys Ala Thr Leu Thr Val Asp Lys Ser Ser
                660                 665                 670

Ser Thr Ala Tyr Met Glu Leu Arg Ser Leu Thr Ser Glu Asp Ser Ala
        675                 680                 685

Val Tyr Tyr Cys Ala Arg Arg Gly Gly Ser Phe Asp Tyr Trp Gly Gln
    690                 695                 700

Gly Thr Thr Leu Thr Val Ser Ser Arg Thr Val Ala Ala Pro Ser Val
705                 710                 715                 720

Phe Ile Phe Pro Pro Ser Asp Glu Gln Leu Lys Ser Gly Thr Ala Ser
                725                 730                 735

Val Val Cys Leu Leu Asn Asn Phe Tyr Pro Arg Glu Ala Lys Val Gln
                740                 745                 750

Trp Lys Val Asp Asn Ala Leu Gln Ser Gly Asn Ser Gln Glu Ser Val
            755                 760                 765

Thr Glu Gln Asp Ser Lys Asp Ser Thr Tyr Ser Leu Ser Ser Thr Leu
        770                 775                 780

Thr Leu Ser Lys Ala Asp Tyr Glu Lys His Lys Val Tyr Ala Cys Glu
785                 790                 795                 800

Val Thr His Gln Gly Leu Ser Ser Pro Val Thr Lys Ser Phe Asn Arg
                805                 810                 815

Gly Glu Cys

<210> SEQ ID NO 32
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 32

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
65                  70                  75                  80
```

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
            115                 120                 125

Thr Ala Ala Leu Gly Cys Leu Val Lys Asp Tyr Phe Pro Glu Pro Val
130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
            195                 200                 205

Ser Cys Asp Lys Thr His
    210

<210> SEQ ID NO 33
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 33

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

-continued

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
            245                 250                 255

Pro Glu Leu Leu Gly Gly Pro Ser Val Phe Leu Phe Pro Pro Lys Pro
        260                 265                 270

Lys Asp Thr Leu Met Ile Ser Arg Thr Pro Glu Val Thr Cys Val Val
    275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Ser Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
        340                 345                 350

Leu Pro Ala Pro Ile Glu Lys Thr Ile Ser Lys Ala Lys Gly Gln Pro
    355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
        420                 425                 430

Ser Lys Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Gly Gly Gly Ser Gly Gly Gly Gly
465                 470                 475                 480

Ser Gly Gly Gly Gly Ser Gly Gln Pro Arg Glu Pro Gln Val Tyr Thr
            485                 490                 495

Leu Pro Pro Ser Arg Glu Glu Met Thr Lys Asn Gln Val Ser Leu Thr
        500                 505                 510

Cys Leu Val Lys Gly Phe Tyr Pro Ser Asp Ile Ala Val Glu Trp Glu
    515                 520                 525

Ser Asn Gly Gln Pro Glu Asn Asn Tyr Lys Thr Thr Pro Pro Val Leu
530                 535                 540

Asp Ser Asp Gly Ser Phe Phe Leu Tyr Ser Lys Leu Thr Val Asp Lys
545                 550                 555                 560

Ser Arg Trp Gln Gln Gly Asn Val Phe Ser Cys Ser Val Met His Glu
            565                 570                 575

Ala Leu His Asn His Tyr Thr Gln Lys Ser Leu Ser Leu Ser Pro Gly
        580                 585                 590

Ser Thr Gly Ser Glu Val Gln Leu Gln Gln Ser Gly Pro Glu Leu Val
    595                 600                 605

Lys Pro Gly Ala Ser Val Lys Ile Ser Cys Lys Thr Ser Gly Tyr Thr
610                 615                 620

Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Gly Thr Ser Tyr

```
                        645                 650                 655
Asn Gln Lys Phe Lys Gly Lys Ala Thr Leu Thr Val Asp Lys Ser Ser
                660                 665                 670

Ser Thr Ala Tyr Met Glu Leu Arg Ser Leu Thr Ser Glu Asp Ser Ala
            675                 680                 685

Val Tyr Tyr Cys Ala Arg Arg Gly Gly Ser Phe Asp Tyr Trp Gly Gln
690                 695                 700

Gly Thr Thr Leu Thr Val Ser Ser Ala Ser Thr Lys Gly Pro Ser Val
705                 710                 715                 720

Phe Pro Leu Ala Pro Ser Ser Lys Ser Thr Ser Gly Gly Thr Ala Ala
                725                 730                 735

Leu Gly Cys Leu Val Lys Asp Tyr Phe Pro Glu Pro Val Thr Val Ser
            740                 745                 750

Trp Asn Ser Gly Ala Leu Thr Ser Gly Val His Thr Phe Pro Ala Val
        755                 760                 765

Leu Gln Ser Ser Gly Leu Tyr Ser Leu Ser Ser Val Val Thr Val Pro
    770                 775                 780

Ser Ser Ser Leu Gly Thr Gln Thr Tyr Ile Cys Asn Val Asn His Lys
785                 790                 795                 800

Pro Ser Asn Thr Lys Val Asp Lys Arg Val Glu Pro Lys Ser Cys Asp
                805                 810                 815

Lys Thr His

<210> SEQ ID NO 34
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 34

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 35

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 36
<211> LENGTH: 792
<212> TYPE: PRT
<213> ORGANISM: Artificial
<220> FEATURE:
<223> OTHER INFORMATION: Chimeric homo sapiens mus musculus

<400> SEQUENCE: 36

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
```

```
            50                  55                  60
Lys Gly Lys Ala Thr Leu Thr Ala Asp Glu Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Tyr Ala Met Asp
                    100                 105                 110

Tyr Trp Gly Gln Gly Thr Thr Val Thr Val Ser Ser Ala Ser Thr Lys
                115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
210                 215                 220

Lys Ser Cys Asp Lys Thr His Thr Ser Pro Pro Ser Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Ser
                290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Gly Gly Gly Ser Gly Gly Gly Gly Ser Gly
            450                 455                 460

Gly Gly Gly Ser Gly Gln Pro Arg Glu Pro Gln Val Tyr Thr Leu Pro
465                 470                 475                 480
```

```
Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Asp Ile Val Met Thr Gln Ser Pro Ala Thr Leu Ser Val Thr
            580                 585                 590

Pro Gly Asp Arg Val Ser Leu Ser Cys Arg Ala Ser Gln Ser Ile Ser
        595                 600                 605

Asp Tyr Leu His Trp Tyr Gln Gln Lys Ser His Glu Ser Pro Arg Leu
    610                 615                 620

Leu Ile Lys Tyr Ala Ser Gln Ser Ile Ser Gly Ile Pro Ser Arg Phe
625                 630                 635                 640

Ser Gly Ser Gly Ser Gly Ser Asp Phe Thr Leu Ser Ile Asn Ser Val
                645                 650                 655

Glu Pro Glu Asp Val Gly Val Tyr Tyr Cys Gln Asn Gly His Ser Phe
            660                 665                 670

Pro Leu Thr Phe Gly Ala Gly Thr Lys Leu Glu Leu Lys Ala Ser Thr
        675                 680                 685

Lys Gly Pro Ser Val Phe Pro Leu Ala Pro Ser Ser Lys Ser Thr Ser
    690                 695                 700

Gly Gly Thr Ala Ala Leu Gly Cys Leu Val Lys Asp Tyr Phe Pro Glu
705                 710                 715                 720

Pro Val Thr Val Ser Trp Asn Ser Gly Ala Leu Thr Ser Gly Val His
                725                 730                 735

Thr Phe Pro Ala Val Leu Gln Ser Ser Gly Leu Tyr Ser Leu Ser Ser
            740                 745                 750

Val Val Thr Val Pro Ser Ser Ser Leu Gly Thr Gln Thr Tyr Ile Cys
        755                 760                 765

Asn Val Asn His Lys Pro Ser Asn Thr Lys Val Asp Lys Arg Val Glu
    770                 775                 780

Pro Lys Ser Cys Asp Lys Thr His
785                 790

<210> SEQ ID NO 37
<211> LENGTH: 223
<212> TYPE: PRT
<213> ORGANISM: Artificial
<220> FEATURE:
<223> OTHER INFORMATION: Chimeric homo sapiens mus musculus

<400> SEQUENCE: 37

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45
```

-continued

Gly Gly Ile Ser Pro Asn Ile Gly Gly Thr Ser Tyr Asn Gln Lys Phe
            50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                     85                  90                  95

Ala Arg Arg Gly Gly Ser Phe Asp Tyr Trp Gly Gln Gly Thr Thr Leu
                100                 105                 110

Thr Val Ser Ser Arg Thr Val Ala Ala Pro Ser Val Phe Ile Phe Pro
                115                 120                 125

Pro Ser Asp Glu Gln Leu Lys Ser Gly Thr Ala Ser Val Val Cys Leu
            130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
                180                 185                 190

Ala Asp Tyr Glu Lys His Lys Val Tyr Ala Cys Glu Val Thr His Gln
                195                 200                 205

Gly Leu Ser Ser Pro Val Thr Lys Ser Phe Asn Arg Gly Glu Cys
            210                 215                 220

<210> SEQ ID NO 38
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 38

Asp Ile Gln Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 39
<211> LENGTH: 680
<212> TYPE: PRT
<213> ORGANISM: Artificial
<220> FEATURE:
<223> OTHER INFORMATION: Chimeric homo sapiens mus musculus

<400> SEQUENCE: 39

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

```
Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ser Thr Gly Ser Glu Val Gln Leu Gln Gln Ser
    450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
        515                 520                 525
```

```
Val Asp Lys Ser Ser Ser Thr Ala Tyr Met Glu Leu Arg Ser Leu Thr
        530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Arg Thr Val
                565                 570                 575

Ala Ala Pro Ser Val Phe Ile Phe Pro Pro Ser Asp Glu Gln Leu Lys
            580                 585                 590

Ser Gly Thr Ala Ser Val Val Cys Leu Leu Asn Asn Phe Tyr Pro Arg
        595                 600                 605

Glu Ala Lys Val Gln Trp Lys Val Asp Asn Ala Leu Gln Ser Gly Asn
610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
            660                 665                 670

Lys Ser Phe Asn Arg Gly Glu Cys
        675                 680

<210> SEQ ID NO 40
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 40

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205
```

Ser Cys Asp Lys Thr His
            210

<210> SEQ ID NO 41
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 41

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ser Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

```
Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 42
<211> LENGTH: 680
<212> TYPE: PRT
<213> ORGANISM: Artificial
<220> FEATURE:
<223> OTHER INFORMATION: Chimeric homo sapiens mus musculus

<400> SEQUENCE: 42

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270
```

```
Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Ser
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ser Thr Gly Ser Glu Val Gln Leu Gln Gln Ser
    450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
        515                 520                 525

Val Asp Lys Ser Ser Ser Thr Ala Tyr Met Glu Leu Arg Ser Leu Thr
    530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Arg Thr Val
                565                 570                 575

Ala Ala Pro Ser Val Phe Ile Phe Pro Pro Ser Asp Glu Gln Leu Lys
            580                 585                 590

Ser Gly Thr Ala Ser Val Val Cys Leu Leu Asn Asn Phe Tyr Pro Arg
        595                 600                 605

Glu Ala Lys Val Gln Trp Lys Val Asp Asn Ala Leu Gln Ser Gly Asn
    610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
            660                 665                 670

Lys Ser Phe Asn Arg Gly Glu Cys
        675                 680
```

-continued

```
<210> SEQ ID NO 43
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 43

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 44
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 44

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95
```

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Ser Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ser Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 45
<211> LENGTH: 680
<212> TYPE: PRT
<213> ORGANISM: Artificial
<220> FEATURE:
<223> OTHER INFORMATION: Chimeric homo sapiens mus musculus

<400> SEQUENCE: 45

Gln Val Gln Leu Gln Gln Ser Gly Ala Glu Leu Val Arg Pro Gly Ser
1               5                   10                  15

```
Ser Val Lys Ile Ser Cys Lys Ala Ser Gly Tyr Ala Phe Ser Ser Tyr
            20                  25                  30
Trp Met Asn Trp Val Lys Gln Arg Pro Gly Gln Gly Leu Glu Trp Ile
        35                  40                  45
Gly Gln Ile Trp Pro Gly Asp Gly Asp Thr Asn Tyr Asn Gly Lys Phe
    50                  55                  60
Lys Gly Lys Ala Thr Leu Thr Ala Asp Glu Ser Ser Ser Thr Ala Tyr
65                  70                  75                  80
Met Gln Leu Ser Ser Leu Ala Ser Glu Asp Ser Ala Val Tyr Phe Cys
                85                  90                  95
Ala Arg Arg Glu Thr Thr Thr Val Gly Arg Tyr Tyr Tyr Ala Met Asp
            100                 105                 110
Tyr Trp Gly Gln Gly Thr Thr Val Thr Val Ser Ser Ala Ser Thr Lys
        115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
        195                 200                 205
Val Asn His Lys Pro Ser Asn Thr Lys Val Asp Lys Arg Val Glu Pro
    210                 215                 220
Lys Ser Ser Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Ser
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
```

```
                    435                 440                 445
Ser Leu Ser Pro Gly Ser Thr Gly Ser Glu Val Gln Leu Gln Gln Ser
    450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
        515                 520                 525

Val Asp Lys Ser Ser Ser Thr Ala Tyr Met Glu Leu Arg Ser Leu Thr
    530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Arg Thr Val
                565                 570                 575

Ala Ala Pro Ser Val Phe Ile Phe Pro Pro Ser Asp Glu Gln Leu Lys
            580                 585                 590

Ser Gly Thr Ala Ser Val Val Cys Leu Leu Asn Asn Phe Tyr Pro Arg
        595                 600                 605

Glu Ala Lys Val Gln Trp Lys Val Asp Asn Ala Leu Gln Ser Gly Asn
    610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
            660                 665                 670

Lys Ser Phe Asn Arg Gly Glu Cys
        675                 680

<210> SEQ ID NO 46
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 46

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
```

```
                115                 120                 125
Thr Ala Ala Leu Gly Cys Leu Val Lys Asp Tyr Phe Pro Glu Pro Val
            130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
                195                 200                 205

Ser Cys Asp Lys Thr His
            210

<210> SEQ ID NO 47
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 47

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
```

```
                 260                 265                 270
Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 48
<211> LENGTH: 698
<212> TYPE: PRT
<213> ORGANISM: Artificial
<220> FEATURE:
<223> OTHER INFORMATION: Chimeric homo sapiens mus musculus

<400> SEQUENCE: 48

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
```

```
            180                 185                 190
Val Thr Val Pro Ser Ser Leu Gly Thr Gln Thr Tyr Ile Cys Asn
            195                 200                 205
Val Asn His Lys Pro Ser Asn Thr Lys Val Asp Lys Arg Val Glu Pro
            210                 215             220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Ser Thr Gly Ser Glu Val Gln Leu Gln Gln Ser
    450                 455                 460
Gly Pro Glu Leu Val Lys Pro Gly Ala Ser Val Lys Ile Ser Cys Lys
465                 470                 475                 480
Thr Ser Gly Tyr Thr Phe Thr Glu Tyr Thr Met His Trp Val Lys Gln
                485                 490                 495
Ser His Gly Lys Ser Leu Glu Trp Ile Gly Gly Ile Ser Pro Asn Ile
            500                 505                 510
Gly Gly Thr Ser Tyr Asn Gln Lys Phe Lys Gly Lys Ala Thr Leu Thr
        515                 520                 525
Val Asp Lys Ser Ser Ser Thr Ala Tyr Met Glu Leu Arg Ser Leu Thr
    530                 535                 540
Ser Glu Asp Ser Ala Val Tyr Tyr Cys Ala Arg Arg Gly Gly Ser Phe
545                 550                 555                 560
Asp Tyr Trp Gly Gln Gly Thr Thr Leu Thr Val Ser Ser Val Glu Gly
                565                 570                 575
Gly Ser Gly Gly Ser Gly Gly Ser Gly Gly Ser Gly Gly Val Asp Asp
            580                 585                 590
Ile Val Met Thr Gln Ser Pro Ala Thr Leu Ser Val Thr Pro Gly Asp
        595                 600                 605
```

```
Arg Val Ser Leu Ser Cys Arg Ala Ser Gln Ser Ile Ser Asp Tyr Leu
    610                 615                 620
His Trp Tyr Gln Gln Lys Ser His Glu Ser Pro Arg Leu Leu Ile Lys
625                 630                 635                 640
Tyr Ala Ser Gln Ser Ile Ser Gly Ile Pro Ser Arg Phe Ser Gly Ser
                645                 650                 655
Gly Ser Gly Ser Asp Phe Thr Leu Ser Ile Asn Ser Val Glu Pro Glu
                660                 665                 670
Asp Val Gly Val Tyr Tyr Cys Gln Asn Gly His Ser Phe Pro Leu Thr
            675                 680                 685
Phe Gly Ala Gly Thr Lys Leu Glu Leu Lys
690                 695

<210> SEQ ID NO 49
<211> LENGTH: 444
<212> TYPE: PRT
<213> ORGANISM: Artificial
<220> FEATURE:
<223> OTHER INFORMATION: Chimeric homo sapiens mus musculus

<400> SEQUENCE: 49

Ile Gln Leu Thr Gln Ser Pro Ala Ser Leu Ala Val Ser Leu Gly Gln
1               5                   10                  15
Arg Ala Thr Ile Ser Cys Lys Ala Ser Gln Ser Val Asp Tyr Asp Gly
                20                  25                  30
Asp Ser Tyr Leu Asn Trp Tyr Gln Gln Ile Pro Gly Gln Pro Pro Lys
            35                  40                  45
Leu Leu Ile Tyr Asp Ala Ser Asn Leu Val Ser Gly Ile Pro Pro Arg
    50                  55                  60
Phe Ser Gly Ser Gly Ser Gly Thr Asp Phe Thr Leu Asn Ile His Pro
65                  70                  75                  80
Val Glu Lys Val Asp Ala Ala Thr Tyr His Cys Gln Gln Ser Thr Glu
                85                  90                  95
Asp Pro Trp Thr Phe Gly Gly Gly Thr Lys Leu Glu Ile Lys Arg Thr
            100                 105                 110
Val Ala Ala Pro Ser Val Phe Ile Phe Pro Pro Ser Asp Glu Gln Leu
        115                 120                 125
Lys Ser Gly Thr Ala Ser Val Val Cys Leu Leu Asn Asn Phe Tyr Pro
    130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
        195                 200                 205
Thr Lys Ser Phe Asn Arg Gly Glu Cys Asp Lys Thr His Thr Cys Pro
    210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
            260                 265                 270
```

```
Asn Trp Tyr Val Asp Gly Val Glu Val His Asn Ala Lys Thr Lys Pro
            275                 280                 285

Arg Glu Glu Gln Tyr Ser Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 50
<211> LENGTH: 698
<212> TYPE: PRT
<213> ORGANISM: Artificial
<220> FEATURE:
<223> OTHER INFORMATION: Chimeric homo sapiens mus musculus

<400> SEQUENCE: 50

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
                100                 105                 110

Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

-continued

```
Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ser Thr Gly Ser Glu Val Gln Leu Gln Gln Ser
    450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
        515                 520                 525

Val Asp Lys Ser Ser Ser Thr Ala Tyr Met Glu Leu Arg Ser Leu Thr
    530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Val Glu Gly
                565                 570                 575

Gly Ser Gly Gly Ser Gly Gly Ser Gly Gly Ser Gly Gly Val Asp Asp
            580                 585                 590

Ile Val Met Thr Gln Ser Pro Ala Thr Leu Ser Val Thr Pro Gly Asp
        595                 600                 605
```

Arg Val Ser Leu Ser Cys Arg Ala Ser Gln Ser Ile Ser Asp Tyr Leu
610                 615                 620

His Trp Tyr Gln Gln Lys Ser His Glu Ser Pro Arg Leu Leu Ile Lys
625                 630                 635                 640

Tyr Ala Ser Gln Ser Ile Ser Gly Ile Pro Ser Arg Phe Ser Gly Ser
                645                 650                 655

Gly Ser Gly Ser Asp Phe Thr Leu Ser Ile Asn Ser Val Glu Pro Glu
            660                 665                 670

Asp Val Gly Val Tyr Tyr Cys Gln Asn Gly His Ser Phe Pro Leu Thr
        675                 680                 685

Phe Gly Ala Gly Thr Lys Leu Glu Leu Lys
690                 695

<210> SEQ ID NO 51
<211> LENGTH: 454
<212> TYPE: PRT
<213> ORGANISM: Artificial
<220> FEATURE:
<223> OTHER INFORMATION: Chimeric homo sapiens mus musculus

<400> SEQUENCE: 51

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

```
Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Ser
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 52
<211> LENGTH: 670
<212> TYPE: PRT
<213> ORGANISM: Artificial
<220> FEATURE:
<223> OTHER INFORMATION: Chimeric homo sapiens mus musculus

<400> SEQUENCE: 52

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Ser Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Ser Thr Gly Ser Glu
        435                 440                 445

Val Gln Leu Gln Gln Ser Gly Pro Glu Leu Val Lys Pro Gly Ala Ser
    450                 455                 460

Val Lys Ile Ser Cys Lys Thr Ser Gly Tyr Thr Phe Thr Glu Tyr Thr
465                 470                 475                 480

Met His Trp Val Lys Gln Ser His Gly Lys Ser Leu Glu Trp Ile Gly
                485                 490                 495

Gly Ile Ser Pro Asn Ile Gly Gly Thr Ser Tyr Asn Gln Lys Phe Lys
            500                 505                 510

Gly Lys Ala Thr Leu Thr Val Asp Lys Ser Ser Ser Thr Ala Tyr Met
        515                 520                 525

Glu Leu Arg Ser Leu Thr Ser Glu Asp Ser Ala Val Tyr Tyr Cys Ala
    530                 535                 540

Arg Arg Gly Gly Ser Phe Asp Tyr Trp Gly Gln Gly Thr Thr Leu Thr
545                 550                 555                 560

Val Ser Ser Arg Thr Val Ala Ala Pro Ser Val Phe Ile Phe Pro Pro
                565                 570                 575

Ser Asp Glu Gln Leu Lys Ser Gly Thr Ala Ser Val Val Cys Leu Leu
            580                 585                 590

Asn Asn Phe Tyr Pro Arg Glu Ala Lys Val Gln Trp Lys Val Asp Asn
```

```
                595                 600                 605
Ala Leu Gln Ser Gly Asn Ser Gln Glu Ser Val Thr Glu Gln Asp Ser
        610                 615                 620

Lys Asp Ser Thr Tyr Ser Leu Ser Ser Thr Leu Thr Leu Ser Lys Ala
625                 630                 635                 640

Asp Tyr Glu Lys His Lys Val Tyr Ala Cys Glu Val Thr His Gln Gly
            645                 650                 655

Leu Ser Ser Pro Val Thr Lys Ser Phe Asn Arg Gly Glu Cys
        660                 665                 670

<210> SEQ ID NO 53
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 53

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 54
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 54

Asp Ile Gln Leu Thr Gln Ser Pro Ala Ser Leu Ala Val Ser Leu Gly
1               5                   10                  15
```

-continued

Gln Arg Ala Thr Ile Ser Cys Lys Ala Ser Gln Ser Val Asp Tyr Asp
                     20                  25                  30

Gly Asp Ser Tyr Leu Asn Trp Tyr Gln Gln Ile Pro Gly Gln Pro Pro
             35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                     85                  90                  95

Glu Asp Pro Trp Thr Phe Gly Gly Gly Thr Lys Leu Glu Ile Lys Arg
             100                 105                 110

Thr Val Ala Ala Pro Ser Val Phe Ile Phe Pro Pro Ser Asp Glu Gln
             115                 120                 125

Leu Lys Ser Gly Thr Ala Ser Val Val Cys Leu Leu Asn Asn Phe Tyr
 130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                 165                 170                 175

Tyr Ser Leu Ser Ser Thr Leu Thr Leu Ser Lys Ala Asp Tyr Glu Lys
             180                 185                 190

His Lys Val Tyr Ala Cys Glu Val Thr His Gln Gly Leu Ser Ser Pro
         195                 200                 205

Val Thr Lys Ser Phe Asn Arg Gly Glu Cys Asp Lys Thr His Thr Cys
 210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                 245                 250                 255

Val Thr Cys Val Val Val Asp Val Ser His Glu Asp Pro Glu Val Lys
             260                 265                 270

Phe Asn Trp Tyr Val Asp Gly Val Glu Val His Asn Ala Lys Thr Lys
         275                 280                 285

Pro Arg Glu Glu Gln Tyr Ser Ser Thr Tyr Arg Val Val Ser Val Leu
 290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                 325                 330                 335

Ala Lys Gly Gln Pro Arg Glu Pro Gln Val Tyr Thr Leu Pro Pro Ser
             340                 345                 350

Arg Glu Glu Met Thr Lys Asn Gln Val Ser Leu Thr Cys Leu Val Lys
         355                 360                 365

Gly Phe Tyr Pro Ser Asp Ile Ala Val Glu Trp Glu Ser Asn Gly Gln
 370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                 405                 410                 415

Gln Gly Asn Val Phe Ser Cys Ser Val Met His Glu Ala Leu His Asn
             420                 425                 430

His Tyr Thr Gln Lys Ser Leu Ser Leu Ser Pro Gly Lys

<210> SEQ ID NO 55
<211> LENGTH: 671
<212> TYPE: PRT
<213> ORGANISM: Artificial
<220> FEATURE:
<223> OTHER INFORMATION: Chimeric homo sapiens mus musculus

<400> SEQUENCE: 55

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn

```
                355                 360                 365
Gln Val Ser Leu Thr Cys Leu Val Lys Gly Phe Tyr Pro Ser Asp Ile
        370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Ser Thr Gly Ser Asp Ile Val Met Thr Gln Ser
    450                 455                 460
Pro Ala Thr Leu Ser Val Thr Pro Gly Asp Arg Val Ser Leu Ser Cys
465                 470                 475                 480
Arg Ala Ser Gln Ser Ile Ser Asp Tyr Leu His Trp Tyr Gln Gln Lys
                485                 490                 495
Ser His Glu Ser Pro Arg Leu Leu Ile Lys Tyr Ala Ser Gln Ser Ile
            500                 505                 510
Ser Gly Ile Pro Ser Arg Phe Ser Gly Ser Gly Ser Gly Ser Asp Phe
        515                 520                 525
Thr Leu Ser Ile Asn Ser Val Glu Pro Glu Asp Val Gly Val Tyr Tyr
    530                 535                 540
Cys Gln Asn Gly His Ser Phe Pro Leu Thr Phe Gly Ala Gly Thr Lys
545                 550                 555                 560
Leu Glu Leu Lys Ala Ser Thr Lys Gly Pro Ser Val Phe Pro Leu Ala
                565                 570                 575
Pro Ser Ser Lys Ser Thr Ser Gly Gly Thr Ala Ala Leu Gly Cys Leu
            580                 585                 590
Val Lys Asp Tyr Phe Pro Glu Pro Val Thr Val Ser Trp Asn Ser Gly
        595                 600                 605
Ala Leu Thr Ser Gly Val His Thr Phe Pro Ala Val Leu Gln Ser Ser
    610                 615                 620
Gly Leu Tyr Ser Leu Ser Ser Val Val Thr Val Pro Ser Ser Ser Leu
625                 630                 635                 640
Gly Thr Gln Thr Tyr Ile Cys Asn Val Asn His Lys Pro Ser Asn Thr
                645                 650                 655
Lys Val Asp Lys Arg Val Glu Pro Lys Ser Cys Asp Lys Thr His
            660                 665                 670

<210> SEQ ID NO 56
<211> LENGTH: 223
<212> TYPE: PRT
<213> ORGANISM: Artificial
<220> FEATURE:
<223> OTHER INFORMATION: Chimeric homo sapiens mus musculus

<400> SEQUENCE: 56

Glu Val Gln Leu Gln Gln Ser Gly Pro Glu Leu Val Lys Pro Gly Ala
1               5                   10                  15
Ser Val Lys Ile Ser Cys Lys Thr Ser Gly Tyr Thr Phe Thr Glu Tyr
                20                  25                  30
Thr Met His Trp Val Lys Gln Ser His Gly Lys Ser Leu Glu Trp Ile
            35                  40                  45
Gly Gly Ile Ser Pro Asn Ile Gly Gly Thr Ser Tyr Asn Gln Lys Phe
```

```
            50                  55                  60
Lys Gly Lys Ala Thr Leu Thr Val Asp Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Arg Gly Gly Ser Phe Asp Tyr Trp Gly Gln Gly Thr Thr Leu
                100                 105                 110

Thr Val Ser Ser Arg Thr Val Ala Ala Pro Ser Val Phe Ile Phe Pro
             115                 120                 125

Pro Ser Asp Glu Gln Leu Lys Ser Gly Thr Ala Ser Val Val Cys Leu
            130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
                180                 185                 190

Ala Asp Tyr Glu Lys His Lys Val Tyr Ala Cys Glu Val Thr His Gln
            195                 200                 205

Gly Leu Ser Ser Pro Val Thr Lys Ser Phe Asn Arg Gly Glu Cys
            210                 215                 220
```

MULTISPECIFIC ANTIGEN BINDING PROTEINS

CROSS-REFERENCE TO RELATED APPLICATIONS

This application is a U.S. National Phase application of International Application No. PCT/EP2015/064070, filed Jun. 23, 2015, which claims priority to U.S. Provisional Application No. 62/017,913, filed Jun. 27, 2014, each of which is incorporated herein by reference.

REFERENCE TO THE SEQUENCE LISTING

This application includes as part of its disclosure a biological sequence listing which is being concurrently submitted through EFS-Web. Said biological sequence listing is contained in a file named "56215o1401.txt" which was created on Dec. 22, 2016, and has a size of 203,866 bytes, and is hereby incorporated by reference in its entirety.

FIELD OF THE INVENTION

Multispecific proteins that bind and specifically redirect NK cells to lyse a target cell of interest are provided. The proteins formats have utility in the treatment of disease.

BACKGROUND

Bispecific antibodies binding two different epitopes and offer opportunities for increasing specificity, broadening potency, and utilizing novel mechanisms of action that cannot be achieved with a traditional monoclonal antibody. A variety of formats for bispecific antibodies that bind to two targets simultaneously have been reported. Cross-linking two different receptors using a bispecific antibody to inhibit a signaling pathway has shown utility in a number of applications (see, e.g., Jackman, et al., (2010) J. Biol. Chem. 285:20850-20859). Bispecific antibodies have also been used to neutralize two different receptors. In other approaches, bispecific antibodies have been used to recruit immune effector cells, where T-cell activation is achieved in proximity to tumor cells by the bispecific antibody which binds receptors simultaneously on the two different cell types (see Baeuerle, P. A., et al, (2009) Cancer Res 69(12): 4941-4). Most such approaches involve bispecific antibodies that link the CD3 complex on T cells to a tumor-associated antigen. The most well-studied bispecific antibody formats are "BiTe" antibodies and "DART" antibodies which do not comprise Fc domains. However these antibodies are known to be difficult to produce, require length cell development, have low productions yields and/or cannot be produced (based on published literature) as a homogenous protein composition. In another example, a bispecific antibody having one arm which bound FcγRIII and another which bound to the HER2 receptor was developed for therapy of ovarian and breast tumors that overexpress the HER2 antigen.

However, despite the existence of a variety of formats for bispecific antibodies, there is therefore a need in the art for proteins with new and well-defined mechanisms of action that can bind two or more biological targets, and that have attractive properties for industrial development.

SUMMARY OF THE INVENTION

The present invention arises from the discovery of a functional multispecific antibody that permits a wide range of antibody variable regions to be readily used, having advantages in manufacturing by being adapted to standard recombinant production techniques, and having improved in vivo pharmacology. The antibodies are particularly adapted to bind a first antigen on a target cell to be eliminated and a second antigen on an immune effector cell (e.g. an NK cell and/or a T cell), where the effector cells are directed to the target cell, e.g. a cancer cell. The antigen on the effector cell can advantageously be an activating receptor. When the multispecific antibody is designed to lack FcγR binding, it will not substantially activate effector cells via CD16, and the multispecific antibody will be selective for the particular effector cells of interest, as a function of the antigen bound by the multispecific antibody's hypervariable regions, thereby avoiding any unwanted FcγR/immune-mediated toxicity (e.g. cytokine-mediated toxicity) and/or inhibitory-FcγR mediated inhibition of the effector cells targeted. The multispecific polypeptide is capable, for example, of directing target antigen-expressing effector cells to lyse a target cell expressing a target antigen, e.g. cancer antigen, viral antigen, etc. The multispecific antibody is particularly effective when binding both effector cell surface protein and a second antigen (an antigen expressed by a target cell) in monovalent fashion.

In one embodiment, provided is a hetero-multimeric multispecific protein (e.g. a heterodimer, a heterotrimer) that binds a first and a second antigen in monovalent fashion and that binds FcRn, the protein comprising: a first antigen binding domain ($ABD_1$) that specifically binds to a first antigen of interest, a second antigen binding domain ($ABD_2$) that specifically binds a second antigen of interest, and at least a portion of a human Fc domain, e.g. an Fc domain that is bound by FcRn, optionally wherein the multispecific antibody is designed to have decreased or substantially lack FcγR binding. In one embodiment, the Fc domain is interposed between the two ABDs (one ABD is placed N-terminal and the other is C-terminal to the Fc domain).

In one embodiment, one of the antigens of interest is an activating receptor present on an effector cell, the other is a target cell antigen (e.g. a tumor antigen, a viral antigen, a microbial antigen), and the multispecific protein is bound by FcRn and has decreased or substantially lack FcγR binding, and the multi-specific protein can, in the presence of the effector cells targeted and target cells, induce signaling in and/or activation of the effector cells through the effector cell polypeptide (the protein acts as an agonist), thereby promoting activation of the effector cells and/or lysis of target cells in a directed manner. Notably, the multi-specific proteins can direct an immune effector response (cytotoxic response) toward a target cell that is substantially limited to the effector cells of interest (the effector cell receptor-expressing cells), and without activating FcγR-mediated toxicity or inhibitor FcγR-mediated inhibition. In one embodiment, provided is an isolated multimeric protein that binds monovalently to an activating receptor expressed by an effector (e.g. T or NK cell) and a to cancer, viral or bacterial antigen, optionally wherein the protein is a heterodimeric or heterotrimeric protein, optionally wherein the protein comprises at least two polypeptide chains formed by CH1-CK dimerization, the protein comprising: (a) a first antigen binding domain that binds to an activating receptor expressed by an effector (e.g. T or NK cell) cell; (b) a second antigen binding domain that binds a cancer, viral or bacterial antigen expressed on a target cell; and (c) a monomeric or dimeric human Fc domain, wherein the protein is capable of binding via its Fc domain human neonatal Fc receptor (FcRn) and having decreased binding to a human Fcγ receptor compared to a full length wild type human IgG1 antibody.

In one aspect of any embodiment herein, a multi-specific protein that binds an activating receptor on an effector cells can for example be characterized by:
(a) ability to activate effector cells that express the activating receptor, when incubated with such effector cells in the presence of target cells; and/or
(b) lack of ability to activate such effector cells when incubated with such effector cells, in the absence of target cells. Optionally, the effector cells are purified NK or T cells.

In one aspect of any embodiment herein, a multi-specific protein described herein can for example be characterized by:
(a) ability to induce effector cells that express the activating receptor to lyse target cells, when incubated such effector cells in the presence of target cells; and/or
(b) lack of ability to activate such effector cells when incubated with such effector cells, in the absence of target cells.

In one aspect of any embodiment herein, a multi-specific protein described herein can for example be characterized by:
(a) ability to induce effector cells that express the activating receptor to lyse target cells, when incubated such effector cells in the presence of target cells; and/or
(b) lack of ability to activate effector cells that express CD16 but do not express the activating receptor, when incubated with such effector cells in the presence of target cells.

The multimeric polypeptide is composed of 2 or 3 different polypeptide chains in which 1 or 2 chains dimerize with a central chain based on CH1-CK heterodimerization (disulfide bond are formed between CH1 and CK domains). The multimer may be composed of a central (first) polypeptide chain comprising two immunoglobulin variable domains that are part of separate antigen binding domains of different antigen specificities, with an Fc domain interposed between the two immunoglobulin variable domains on the polypeptide chain, and a CH1 or CK constant domain placed on the polypeptide chain adjacent to one of, or each of, the variable domain. Examples of the central polypeptide chain domain arrangements are as follows, where each $V_1$, $V_2$ or $V_3$ is a variable domain:

$V_1$-(CH1 or CK)-Fc domain-$V_2$;
$V_2$-Fc domain-$V_1$-(CH1 or CK);
$V_1$-(CH1 or CK)-Fc domain-$V_2$-$V_3$;
$V_2$-$V_3$-Fc domain-$V_1$-(CH1 or CK); and
$V_1$-(CH1 or CK)-Fc domain-$V_2$-(CH1 or CK)

The Fc domain may be a full Fc domain or a portion thereof sufficient to confer the desired functionality (e.g. FcRn binding). A second additional polypeptide chain will then be configured which will comprise an immunoglobulin variable domain and a CH1 or CK constant region selected so as to permit CH1-CK heterodimerization with the central polypeptide chain; the immunoglobulin variable domain will be selected so as to complement the variable domain of the central chain that is adjacent to the CH1 or CK domain, whereby the complementary variable domains form an antigen binding domain for a first antigen of interest.

The antigen binding domain for the second antigen of interest can then be formed according to several configurations. In a first configuration, the central polypeptide chain comprises three immunoglobulin variable domains, wherein the first variable domain is part of (together with the V domain in the second polypeptide) the antigen binding domain for a first antigen of interest and the second and third variable domains are configured as tandem variable domains forming the antigen binding domain for the second antigen of interest (e.g. a heavy chain variable domain (VH) and a light chain (kappa) variable domain (VK), for example forming an scFv unit).

In another configuration, a third polypeptide chain is provided so as to provide the second variable region of the second antibody binding domain. Similarly to the second chain, the third chain will comprise an immunoglobulin variable domain and a CH1 or CK constant region selected so as to permit CH1-CK heterodimerization with the central polypeptide chain. In this configuration the central chain will comprise two V-(CH1 or CK) units with an interposed Fc domain, a first V-(CH1 or CK) unit with form a CH1-CK heterodimer with a V-(CH1 or CK) unit of the second chain, and the second V-(CH1 or CK) unit will form a heterodimer with a V-(CH1 or CK) unit of the third chain. The immunoglobulin variable domain of the third chain will be selected so as to complement the unpaired variable domain of the central chain, whereby the complementary variable domains form an antigen binding domain for a second antigen of interest. Because CH1 and CK domains will form heterodimers so long as the V domains adjacent thereto are complementary (i.e. not both VH or both VK), one can select variable and constant domains that are not naturally associated with one another so as to configure the variable and constant domains on the second and third chains such that each V-(CH1 or CK) unit on the second and third chains finds a preferred binding partner on the central chain. E.g. a VH-CK unit will heterdimerize with a VK-CH1 but not with a VK-CK. This will permit the preferred pairing of the chains during production.

The multimeric polypeptide can be designed to have a monomeric Fc domain or a dimeric Fc domain. For monomeric Fc domains, the Fc domain may comprise a CH3 domain having one or more amino acid mutations (e.g. substitutions) in the CH3 dimer interface to prevent CH3-CH3 dimerization.

In one aspect, provided is a heterotrimeric bispecific antibody that binds a first and a second antigen of interest in monovalent fashion, wherein the antibody comprises a monomeric or dimeric Fc domain that binds human FcRn, optionally further wherein the Fc domain does not bind a human Fcγ receptor.

In one embodiment, provided is a heteromultimeric, e.g. heterodimeric, bispecific polypeptide comprising: (a) a first polypeptide chain comprising a first variable region (V), fused to a CH1 or CK domain, wherein the V-(CH1/CK) unit is in turn fused to a first terminus (N- or C-terminus) of a human Fc domain (a full Fc domain or a portion thereof); (b) a second polypeptide chain comprising a first variable region (V) fused to a CH1 or CK domain that is complementary with the CH1 or CK of the first chain to form a CH1-CK dimer, optionally wherein the V-(CH1/CK) unit is fused to at least a human Fc domain (a full Fc domain or a portion thereof), wherein the two first variable regions form an antigen binding domain that binds a first antigen of interest in monovalent fashion, and (c) an antigen binding domain that binds a second antigen (optionally together with a complementary antigen binding domain), fused to a second terminus (N- or C-terminus) of the Fc domain of the first polypeptide (or of the second Fc-derived polypeptide, if such polypeptide comprises an Fc domain) such that the Fc domain is interposed between the V-(CH1/CK) unit and the antigen binding domain that binds a second antigen. Optionally the first and second polypeptide chains are bound by interchain disulfide bonds, e.g. formed between respective CH1 and CK domains. Optionally a V-(CH1/CK) unit is fused to a human Fc domain directly, or via intervening sequences, e.g. hinge region, linker, other protein domain(s), etc.

In one embodiment of the above heteromultimeric polypeptide, the polypeptide is a heterodimer, wherein the antigen binding domain for a second antigen is an scFv, optionally an scFv that binds an activating receptor on an effector cell.

In one aspect provided is an isolated hetero-multimeric polypeptide that binds a first and second antigen of interest in monovalent fashion, comprising:
  (a) a first polypeptide chain comprising a first variable domain (V) fused to a CH1 of CK constant region, a second variable domain, and an Fc domain or portion thereof interposed between the first and second variable domains; and
  (b) a second polypeptide chain comprising a first variable domain (V) fused at its C-terminus to a CH1 or CK constant region selected to be complementary to the CH1 or CK constant region of the first polypeptide chain such that the first and second polypeptides form a CH1-CK heterodimer in which the first variable domain of the first polypeptide chain and the first variable domain of the second polypeptide form an antigen binding domain that binds the first antigen of interest.

Optionally, the first polypeptide chain comprises a first variable domain (V) fused at its C-terminus to a CH1 and the second polypeptide chain comprises a first variable domain fused at its C-terminus to a CK constant region, such that the first and second polypeptides form a CH1-CK heterodimer. Alternatively, the first polypeptide chain comprises a first variable domain (V) fused at its C-terminus to a CK and the second polypeptide chain comprises a first variable domain fused at its C-terminus to a CH1 constant region, such that the first and second polypeptides form a CK-CH1 heterodimer. Optionally, the first variable domain of the first polypeptide chain and the first variable domain of the second polypeptide chain are derived from the same first parental antibody that specifically binds the first antigen, and the second variable domain of the first polypeptide is from a second parental antibody that specifically binds the second antigen.

In one embodiment, the first polypeptide chain further comprises a third variable domain fused to the second variable domain,
  wherein the first and second polypeptide form a CH1-CK heterodimer, wherein the first variable domain of the first polypeptide chain and the first variable domain of the second polypeptide chain form an antigen binding domain specific for the first antigen of interest, and wherein the second and third variable domains of the first polypeptide chain form an scFv specific for the second antigen of interest. Optionally first polypeptide chain has the domain arrangement: $V_2$-$V_3$-Fc domain-$V_1$-(CH1 or CK), such that a hetero-multimeric polypeptide is formed having the domain arrangement:

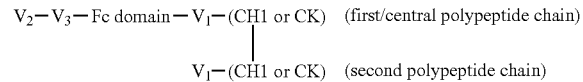

$V_2$—$V_3$—Fc domain—$V_1$—(CH1 or CK)    (first/central polypeptide chain)

$V_1$—(CH1 or CK)    (second polypeptide chain)

wherein one of $V_1$ of the first polypeptide chain and $V_1$ of the second polypeptide chain is a light chain variable domain and the other is a heavy chain variable domain.

Optionally first polypeptide chain has the domain arrangement: $V_1$-(CH1 or CK)-Fc domain-$V_2$-$V_3$, such that a hetero-multimeric polypeptide is formed having the domain arrangement:

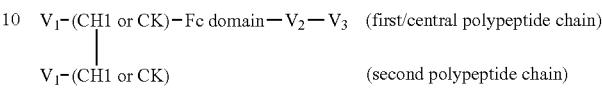

$V_1$-(CH1 or CK)-Fc domain—$V_2$—$V_3$    (first/central polypeptide chain)

$V_1$-(CH1 or CK)    (second polypeptide chain)

wherein one of $V_1$ of the first polypeptide chain and $V_1$ of the second polypeptide chain is a light chain variable domain and the other is a heavy chain variable domain.

In one aspect provided is an isolated heterodimeric polypeptide that binds a first and second antigen of interest in monovalent fashion, optionally wherein one of the antigens is expressed on an immune effector cell and the other is an antigen of interest, comprising:
  (a) a first polypeptide chain comprising, from N- to C-terminus, a first variable domain (V), a CH1 of CK constant region, a Fc domain or portion thereof, a second variable domain and third variable domain; and
  (b) a second polypeptide chain comprising, from N- to C-terminus, a first variable domain (V), a CH1 or CK constant region, and optionally a Fc domain or portion thereof, wherein the CH1 or CK constant region is selected to be complementary to the CH1 or CK constant region of the first polypeptide chain such that the first and second polypeptides form a CH1-CK heterodimer in which the first variable domain of the first polypeptide chain and the first variable domain of the second polypeptide form an antigen binding domain that binds the first antigen of interest; and wherein a second variable domain and third variable domain forms an antigen binding domain that binds the second antigen of interest. When the second polypeptide chain lacks an Fc domain, the first polypeptide chain will comprise an Fc domain modified to prevent CH3-CH3 dimerization (e.g., substitutions or tandem CH3 domain).

In one aspect provided is an isolated heterodimeric polypeptide that binds a first and second antigen of interest in monovalent fashion, optionally wherein one of the antigens is expressed on an immune effector cell and the other is an antigen of interest, comprising:
  (a) a first polypeptide chain comprising, from N- to C-terminus, a second variable domain and third variable domain, a Fc domain or portion thereof, a first variable domain (V), and a CH1 of CK constant region; and
  (b) a second polypeptide chain comprising, from N- to C-terminus, a first variable domain (V), a CH1 or CK constant region, wherein the CH1 or CK constant region is selected to be complementary to the CH1 or CK constant region of the first polypeptide chain such that the first and second polypeptides form a CH1-CK heterodimer in which the first variable domain of the first polypeptide chain and the first variable domain of the second polypeptide form an antigen binding domain that binds the first antigen of interest; and wherein a second variable domain and third variable domain forms an antigen binding domain that binds the second antigen of interest. The first polypeptide chain can comprise an Fc domain modified to prevent CH3-CH3 dimerization (e.g., substitutions or tandem CH3 domain).

In one embodiment, provided is a trimeric polypeptide, comprising:
(a) a first polypeptide chain comprising a first variable domain (V) fused to a first CH1 or CK constant region, a second variable domain (V) fused to a second CH1 or CK constant region, and an Fc domain or portion thereof interposed between the first and second variable domains (i.e. the Fc domain is interposed between the first and second V-(CH1/CK) units);
(b) a second polypeptide chain comprising a variable domain fused at its C-terminus to a CH1 or CK constant region selected to be complementary to the first CH1 or CK constant region of the first polypeptide chain such that the first and second polypeptides form a CH1-CK heterodimer; and
(c) a third polypeptide chain comprising a variable domain fused at its C-terminus to a CH1 or CK constant region, wherein the variable domain and CH1 or CK constant region are selected to be complementary to the second variable domain and CH1 or CK constant region of the first polypeptide chain such that the first and third polypeptides form a CH1-CK heterodimer bound by disulfide bond(s) formed between the CH1 or CK constant region of the third polypeptide and the second CH1 or CK constant region of the first polypeptide, but not between the CH1 or CK constant region of the third polypeptide and the first CH1 or CK constant region of the first polypeptide wherein the first, second and third polypeptides form a CH1-CK heterotrimer, and wherein the first variable domain of the first polypeptide chain and the variable domain of the second polypeptide chain form an antigen binding domain specific for a first antigen of interest, and the second variable domain of the first polypeptide chain and the variable domain on the third polypeptide chain form an antigen binding domain specific for a second antigen of interest. Optionally, the first variable domain of the first polypeptide chain and the variable domain of the second polypeptide chain are derived from the same first parental antibody that specifically binds the first antigen, and the second variable domain of the first polypeptide chain and the variable domain of the third polypeptide chain are derived from the same second parental antibody that specifically binds the second antigen.

In one embodiment, provided is a trimeric polypeptide that binds a first and second antigen of interest in monovalent fashion, optionally wherein one of the antigens is expressed on an immune effector cell and the other is an antigen of interest, comprising:
(a) a first polypeptide chain comprising, from N- to C-terminus, a first variable domain (V) fused to a first CH1 or CK constant region, an Fc domain or portion thereof, and a second variable domain (V) fused to a second CH1 or CK constant region;
(b) a second polypeptide chain comprising, from N- to C-terminus, a variable domain fused to a CH1 or CK constant region selected to be complementary to the first (but not the second) CH1 or CK constant region of the first polypeptide chain such that the first and second polypeptides form a CH1-CK heterodimer, and optionally an Fc domain or portion thereof; and
(c) a third polypeptide chain comprising, from N- to C-terminus, a variable domain fused to a CH1 or CK constant region, wherein the variable domain and CH1 or CK constant region are selected to be complementary to the second (but not the first) variable domain and CH1 or CK constant region of the first polypeptide chain. The first and third polypeptides will therefore form a CH1-CK heterodimer formed between the CH1 or CK constant region of the third polypeptide and the second CH1 or CK constant region of the first polypeptide, but not between the CH1 or CK constant region of the third polypeptide and the first CH1 or CK constant region of the first polypeptide. The first, second and third polypeptides form a CH1-CK heterotrimer, and wherein the first variable domain of the first polypeptide chain and the variable domain of the second polypeptide chain form an antigen binding domain specific for a first antigen of interest, and the second variable domain of the first polypeptide chain and the variable domain on the third polypeptide chain form an antigen binding domain specific for a second antigen of interest.

Provided also is a purified or homogenous composition, wherein at least 90%, 95% or 99% of the proteins in the composition are a multimeric polypeptide of the disclosure.

Optionally, in any embodiment where two Fc domains are present in the multimeric polypeptide, an Fc domain comprises a CH2 and a CH3 domain capable of CH3-CH3 dimerization.

Optionally in any embodiment, each of the variable domains is a single immunoglobulin heavy or light chain variable domain.

Optionally in any embodiment, a Fc domain is fused to an antigen binding domain, CH1 domain and/or CK domain via a hinge region or linker peptide.

Optionally in any embodiment, an Fc domain comprises a CH2 domain. Optionally, a CH2 domain is fused to an antigen binding domain, CH1 domain and/or CK domain via a hinge region or linker peptide. Optionally, a CH2 domain comprises an amino acid substitution to reduce binding to a human Fcγ receptor. In one embodiment, the multispecific polypeptide lacks N-linked glycosylation or has modified N-linked glycosylation. In one embodiment, the multispecific polypeptide comprises an N297X mutation, wherein X is any amino acid other than asparagine.

Optionally in any embodiment, two polypeptide chains within a multimeric polypeptide are bound to one another by interchain disulfide bond(s) formed between respective hinge regions and/or respective CH1/CK constant regions.

Optionally in any embodiment, the multispecific polypeptide (or the Fc portion thereof) is capable of binding to human neonatal Fc receptor (FcRn).

Optionally in any embodiment, the multispecific polypeptide (or the Fc portion thereof) has decreased binding to a human Fcγ receptor compared to a full length wild type human IgG1 antibody. Optionally, the multispecific polypeptide (or the Fc portion thereof) substantially lacks binding to a human Fcγ receptor.

In one aspect of any embodiment herein, the multimeric polypeptide (and/or its Fc domain) has decreased binding to a human Fcγ receptor (e.g. CD16, CD32A, CD32B and/or CD64). e.g., compared to a full length wild type human IgG1 antibody.

In one embodiment, the multimeric polypeptide has decreased (e.g. partial or complete loss of) antibody dependent cytotoxicity (ADCC), complement dependent cytotoxicity (CDC), antibody dependent cellular phagocytosis (ADCP), FcR-mediated cellular activation (e.g. cytokine release through FcR cross-linking), and/or FcR-mediated platelet activation/depletion, as mediated by immune cells that do not express an antigen of interest bound by the variable regions of the multimeric polypeptide (i.e. in the absence of cells that express an antigen of interest bound by the variable regions), compared, e.g., to the same polypeptide having a wild-type Fc domain of human IgG1 isotype.

In one aspect of any embodiment herein, the CH2 domain comprises an amino acid modification that decreases binding to a human Fcγ receptor, compared to a wild-type CH2 domain. In one embodiment the CH2-modified multispecific polypeptide has decreased (e.g. partial or complete loss of) antibody dependent cytotoxicity (ADCC), complement dependent cytotoxicity (CDC), antibody dependent cellular phagocytosis (ADCP), FcR-mediated cellular activation (e.g. cytokine release through FcR cross-linking), and/or FcR-mediated platelet activation/depletion, mediated by immune effector cells that do not express antigen of interest bound by the multimeric polypeptide's ABDs, compared, e.g., to the same polypeptide having a wild-type CH2 domain.

Optionally in any embodiment, each antigen binding domain comprises the hypervariable regions, optionally the heavy and light chain CDRs, of an antibody.

Optionally, in any embodiment where a single Fc domain is present in the multimeric polypeptide, an Fc domain(s) comprises a CH3 domain comprising an amino acid substitution at 1, 2, 3, 4, 5, 6 or 7 of the positions L351, T366, L368, P395, F405, T407 and/or K409 (EU numbering as in Kabat), or a tandem CH3 domain.

Optionally in any embodiment, the Fc domain(s) is a human IgG4 Fc domain or a portion thereof, optionally comprising one or more amino acid modifications.

Optionally in any embodiment, one of the first or second antigen of interest is a cancer antigen and the other is a polypeptide expressed on the surface of an immune effector cell.

Optionally in any embodiment, one of the first or second antigen of interest is a viral or bacterial antigen and the is a polypeptide expressed on the surface of an immune effector cell.

Optionally in any embodiment, a variable domain comprises framework residues from a human framework region, e.g., a variable domain comprises 1, 2 or 3 CDRs of human or non-human origin and framework residues of human origin.

In one aspect of any of the embodiments herein, the bispecific polypeptide has a great binding affinity (monovalent) for a cancer antigen (or a viral or bacterial antigen) than for an antigen expressed by an immune effector cell. Such antibodies will provide for advantageous pharmacological properties. In one aspect of any of the embodiments of the invention, the polypeptide has a Kd for binding (monovalent) to an antigen expressed by immune effector cell of less than $10^{-7}$ M, preferably less than $10^{-9}$ M, or preferably less than $10^{-9}$ M for binding to an polypeptide expressed by an immune effector cell; optionally the polypeptide has a Kd for binding (monovalent) to a cancer, viral or bacterial antigen that is less than (i.e. has better binding affinity than) the Kd for binding (monovalent) to the antigen expressed by immune effector cell.

In one embodiment of any of the polypeptides herein, the multispecific polypeptide is capable of directing effector cells (e.g. a T cell, an NK cell) expressing one of first or second antigen of interest to lyse a target cell expressing the other of said first of second antigen of interest (e.g. a cancer cell).

In one aspect of any of the embodiments herein, provided is a recombinant nucleic acid encoding a first polypeptide chain, and/or a second polypeptide chain and/or a third polypeptide chain of any of the proteins of the disclosure. In one aspect of any of the embodiments herein, provided is a recombinant host cell comprising a nucleic acid encoding a first polypeptide chain, and/or a second polypeptide chain and/or a third polypeptide chain of any of the proteins of the disclosure, optionally wherein the host cell produces a protein of the disclosure with a yield (final productivity, following purification) of at least 1, 2, 3 or 4 mg/L. Also provided is a kit or set of nucleic acids comprising a recombinant nucleic acid encoding a first polypeptide chain of the disclosure, a recombinant nucleic acid encoding a second polypeptide chain of the disclosure, and, optionally, a recombinant nucleic acid encoding a third polypeptide chain of the disclosure. Also provided are methods of making monomeric, heterodimeric and heterotrimeric proteins of the disclosure.

In one embodiment, the invention provides methods of making a heterodimeric protein (e.g. any heterodimeric protein described herein), comprising:
   a) providing a first nucleic acid encoding a first polypeptide chain described herein (e.g., a polypeptide chain comprising a first variable domain (V) fused to a CH1 of CK constant region, a second variable domain (and optionally third variable domain, wherein the second and third variable domain form an antigen binding domain), and an Fc domain or portion thereof interposed between the first and second variable domains);
   b) providing a second nucleic acid encoding a second polypeptide chain described herein (e.g., a polypeptide chain comprising a first variable domain (V) fused at its C-terminus to a CH1 or CK constant region selected to be complementary to the CH1 or CK constant region of the first polypeptide chain such that the first and second polypeptides form a CH1-CK heterodimer in which the first variable domain of the first polypeptide chain and the first variable domain of the second polypeptide form an antigen binding domain); wherein one of the first or second antigen binding domains binds a polypeptide on the surface of an immune effector cell and the other binds a tumor, viral or bacterial antigen; and
   c) expressing said first and second nucleic acids in a host cell to produce a protein comprising said first and second polypeptide chains, respectively; and recovering a heterodimeric protein. Optionally, the heterodimeric protein produced represents at least 20%, 25% or 30% of the total protein (e.g. bispecific proteins) obtained prior to purification. Optionally step (c) comprises loading the protein produced onto an affinity purification support, optionally an affinity exchange column, optionally a Protein-A support or column, and collecting the heterodimeric protein; and/or loading the protein produced (e.g., the protein collected following loading onto an affinity exchange or Protein A column) onto an ion exchange column; and collecting the heterodimeric fraction. In one embodiment, the second variable domain (optionally together with the third variable domain) of the first polypeptide chain binds a polypeptide on the surface of an immune effector cell.

By virtue of their ability to be produced in standard cell lines and standardized methods with high yields, unlike BITE, DART and other bispecific formats, the proteins of the disclosure also provide a convenient tool for screening for the most effective variable regions to incorporated into a multispecific protein. In one aspect, the present disclosure provides a method for identifying or evaluating candidate variable regions for use in a heterodimeric protein, comprising the steps of:
  a) providing a plurality of nucleic acid pairs, wherein each pair includes one nucleic acid encoding a heavy chain candidate variable region and one nucleic acid encoding a light chain candidate variable region, for each of a plurality of heavy and light chain variable region pairs (e.g., obtained from different antibodies binding the same or different antigen(s) of interest);
  b) for each of the plurality nucleic acid pairs, making a heterodimeric protein by:
    (i) producing a first nucleic acid encoding a first polypeptide chain comprising one of the heavy or light chain candidate variable domains (V) fused to a CH1 or CK constant region, a second variable domain (and optionally third variable domain, wherein the second and third variable domain form a first antigen binding domain), and an Fc domain or portion thereof interposed between the candidate and second variable domains);
    (ii) producing a second nucleic acid encoding a second polypeptide chain comprising the other of the heavy or light chain candidate variable domains (V) fused at its C-terminus to a CH1 or CK constant region selected to be complementary to the CH1 or CK constant region of the first polypeptide chain such that the first and second polypeptides form a CH1-CK heterodimer in which the heavy and light chain candidate variable domains form a second antigen binding domain; and
    (iii) expressing said nucleic acids encoding the first and second polypeptide chains in a host cell to produce a protein comprising said first and second polypeptide chains, respectively; and recovering a heterodimeric protein; and
  c) evaluating the plurality of heterodimeric proteins produced for a biological activity of interest, e.g., an activity disclosed herein. In one embodiment, the first antigen binding domain binds a polypeptide on the surface of an immune effector cell and the second antigen binding domain a tumor, viral or bacterial antigen; optionally the first antigen binding domain is an scFv. Optionally, the heterodimeric protein produced represents at least 20%, 25% or 30% of the total protein obtained prior to purification. Optionally the recovering step in (iii) comprises loading the protein produced onto an affinity purification support, optionally an affinity exchange column, optionally a Protein-A support or column, and collecting the heterodimeric protein; and/or loading the protein produced (e.g., the protein collected following loading onto an affinity exchange or Protein A column) onto an ion exchange column; and collecting the heterodimeric fraction.

In one embodiment, provided is a method of making a heterotrimeric protein (e.g. any heterotrimeric protein described herein), comprising:
  (a) providing a first nucleic acid encoding a first polypeptide chain described herein (e.g., a polypeptide chain comprising a first variable domain (V) fused to a first CH1 or CK constant region, a second variable domain fused to a second CH1 or CK constant region, and an Fc domain or portion thereof interposed between the first and second (V-CH1/CK) units);
  (b) providing a second nucleic acid encoding a second polypeptide chain described herein (e.g., a polypeptide chain comprising a variable domain (V) fused at its C-terminus to a CH1 or CK constant region selected to be complementary to the first CH1 or CK constant region of the first polypeptide chain such that the first and second polypeptides form a CH1-CK heterodimer in which the first variable domain of the first polypeptide chain and the variable domain of the second polypeptide form an antigen binding domain);
  (c) providing a third nucleic acid comprising a third polypeptide chain described herein (e.g., a polypeptide chain comprising a variable domain fused at its C-terminus to a CH1 or CK constant region, wherein the CH1 or CK constant region is selected to be complementary to the second variable domain and second CH1 or CK constant region of the first polypeptide chain such that the first and third polypeptides form a CH1-CK heterodimer in which the second variable domain of the first polypeptide and the variable domain of the third polypeptide form an antigen binding domain; and
  (d) expressing said first, second and third nucleic acids in a host cell to produce a protein comprising said first, second and third polypeptide chains, respectively; and recovering a heterotrimeric protein. Optionally, the heterotrimeric protein produced represents at least 20%, 25% or 30% of the total protein obtained prior to purification. Optionally step (d) comprises loading the protein produced onto an affinity purification support, optionally an affinity exchange column, optionally a Protein-A support or column, and collecting the heterotrimeric protein; and/or loading the protein produced (e.g., the protein collected following loading onto an affinity exchange or Protein A column) onto an ion exchange column; and collecting the heterotrimeric fraction. Optionally, one of the antigen binding domains binds a polypeptide on the surface of an immune effector cell, and the other binds an antigen of interest. In one embodiment, the second or the third polypeptide further comprises and Fc domain or fragment thereof fused to the C-terminus of the CH1 or CK domain (e.g. via a hinge domain or linker). In one embodiment, the second variable domain of the first polypeptide and the variable domain of the third polypeptide form an antigen binding domain that binds a polypeptide on the surface of an immune effector cell.

In one aspect, the present disclosure provides a method for identifying or evaluating candidate variable regions for use in a heterotrimeric protein, comprising the steps of:
  a) providing a plurality of nucleic acid pairs, wherein each pair includes one nucleic acid encoding a heavy chain candidate variable region and one nucleic acid encoding a light chain candidate variable region, for each of a plurality of heavy and light chain variable region pairs (e.g., obtained from different antibodies binding the same or different antigen(s) of interest);
  b) for each of the plurality nucleic acid pairs, making a heterotrimeric protein by:
    (i) producing a first nucleic acid encoding a first polypeptide chain comprising one of the heavy or light chain candidate variable domains (V) fused to a first CH1 or CK constant region, a second variable domain fused to a second CH1 or CK constant region, and an Fc domain or portion thereof interposed between the first and second (V-CH1/CK) units);
    (ii) producing a second nucleic acid encoding a second polypeptide chain comprising the other of the heavy or light chain candidate variable domains (V) fused at its C-terminus to a CH1 or CK constant region selected to be complementary to the first CH1 or CK constant region of the first polypeptide chain such that the first and second polypeptides form a CH1-CK heterodimer in which the heavy and light chain candidate variable domains form an antigen binding domain;

(ii) producing a third nucleic acid encoding a third polypeptide chain comprising a variable domain fused at its C-terminus to a CH1 or CK constant region, wherein the CH1 or CK constant region is selected to be complementary to the second variable domain and second CH1 or CK constant region of the first polypeptide chain such that the first and third polypeptides form a CH1-CK heterodimer in which the second variable domain of the first polypeptide and the variable domain of the third polypeptide form an antigen binding domain; and (iii) expressing said nucleic acids encoding the first and second polypeptide chains in a host cell to produce said first and second polypeptide chains, respectively; and recovering a heterodimeric protein; and c) evaluating the plurality of heterodimeric proteins produced for a biological activity of interest, e.g., an activity disclosed herein. In one embodiment, the second or the third polypeptide further comprises and Fc domain or fragment thereof fused to the C-terminus of the CH1 or CK domain (e.g. via a hinge domain or linker). Optionally, the heterotrimeric protein produced represents at least 20%, 25% or 30% of the total proteins obtained prior to purification. Optionally the recovering step in (iii) comprises loading the protein produced onto an affinity purification support, optionally an affinity exchange column, optionally a Protein-A support or column, and collecting the heterotrimeric protein; and/or loading the protein produced (e.g., the protein collected following loading onto an affinity exchange or Protein A column) onto an ion exchange column; and collecting the heterotrimeric fraction.

In the methods for identifying or evaluating candidate variable regions, candidate variable regions can for example be from antibodies that binds a polypeptide on the surface of an immune effector cell, or from antibodies that bind an antigen of interest, e.g. a tumor, bacterial or viral antigen. When the candidate variable regions are from antibodies against a tumor, bacterial or viral antigen, the other variable region can be from an antibody that binds a polypeptide on the surface of an immune effector cell, which will permit a panel of antibodies to the tumor, bacterial or viral antigen to be tested in the context of an anti-effector cell ABD which has been determined to be effective. It will also be appreciated that the position of the respective ABDs for the candidate variable region pair and the other variable region pair can be inverted. For example, in a trimeric protein the methods can be modified such that the heavy and light chain candidate variable domains are formed by the second V region of the first polypeptide and the V region of the second polypeptide, and the other variable region pair are formed by the first V region of the first polypeptide and the V region of the third polypeptide.

In one aspect, the present disclosure provides a method for identifying or evaluating candidate protein configurations for use in a hetero-multimeric protein, comprising the steps of:

producing, separately (e.g. in separate containers), a plurality of hetero-multimeric proteins of the disclosure, wherein the proteins differ in their domain arrangements, and evaluating the plurality of hetero-multimeric proteins produced for a biological activity of interest, e.g., an activity disclosed herein. In one embodiment, the proteins having different domain arrangements share antigen binding domains (e.g. the same CDRs or variable domains) for the first and/or second antigen of interest. In one embodiment 2, 3, 4, 5, 6, 7 or more different proteins are produced and evaluated. In one embodiment, one or more of (or all of) the proteins are selected from the group of proteins having a domain arrangement disclosed herein, e.g. that of formats F2, F5, F6, F7, F8, F9, F10, F11, F12, F13, F14, F15, F16 and F17. In one embodiment the proteins are produced according to the methods disclosed herein.

In one aspect, the present disclosure provides a library of at least 5, 10, 20, 30, 50 hetero-multimeric proteins of the disclosure, wherein the proteins share domain arrangements but differ in the amino acid sequence of the variable domain of one or both of their antigen binding domains.

In one aspect, the present disclosure provides a library of at least 2, 3, 4, 5 or 10 hetero-multimeric proteins of the disclosure, wherein the proteins share the amino acid sequence of the variable domain of one or both of their antigen binding domains, but differ in domain arrangements.

In one embodiment, the second variable domain of the first polypeptide and the variable domain of the third polypeptide form an antigen binding domain that binds an activating receptor on an effector cell. In one embodiment, evaluating heterodimeric or heterotrimeric proteins for a characteristic of interest comprises evaluating the proteins for one or more properties selected from the group consisting of: binding to an antigen of interest, binding to an FcRn receptor, binding to an Fcγ receptor, Fc-domain mediated effector function(s), agonistic or antagonistic activity at a polypeptide to which the multimeric proteins binds, ability to modulate the activity (e.g. cause the death of) a cell expressing the antigen of interest, ability to direct a lymphocyte to a cell expressing the antigen of interest, ability to activate a lymphocyte in the presence and/or absence of a cell expressing the antigen of interest, lymphocyte (e.g. T cell or NK cell) activation in presence but not in absence of target cells, lack of activation of antigen-of-interest-negative lymphocytes, stability or half-life in vitro or in vivo, production yield, purity within a composition, and susceptibility to aggregate in solution.

In one aspect, the present disclosure provides a method for identifying or evaluating a hetero-multimeric protein, comprising the steps of:
(a) providing nucleic acids encoding a hetero-multimeric protein described herein;
(b) expressing said nucleic acids in a host cell to produce said protein, respectively; and recovering said protein; and
(c) evaluating the protein produced for a biological activity of interest, e.g., an activity disclosed herein. In one embodiment, a plurality of different proteins are produced and evaluated.

In one embodiment, the protein binds an activating receptor on an effector cell and an antigen of interest, and the step (c) comprises:
(i) testing the ability of the protein to activate effector cells that express the activating receptor, when incubated with such effector cells in the presence of target cells (that express antigen of interest). Optionally, step (i) is followed by a step comprising: selecting a protein (e.g., for further development, for use as a medicament) that activates said effector cells.

In one embodiment, the protein binds an activating receptor on an effector cell and an antigen of interest, and the step (c) comprises:
(i) testing the ability of the protein to activate effector cells that express the activating receptor, when incubated with such effector cells in the absence of target cells (that express antigen of interest). Optionally, step (i) is followed by a step comprising: selecting a protein (e.g., for further development, for use as a medicament) that does not substantially activate said effector cells.

In one embodiment, the protein binds an activating receptor on an effector cell and an antigen of interest, and the step (c) comprises:
(i) testing the ability of the protein to activate effector cells that express the activating receptor, when incubated with such effector cells in the presence of target cells (that express antigen of interest); and
(ii) testing the ability of the protein to activate effector cells that express the activating receptor, when incubated with such effector cells in the absence of target cells (that express antigen of interest). Optionally, the method further comprises: selecting a protein (e.g., for further development, for use as a medicament) that does not substantially activate said effector cells when incubated in the absence of target cells, and that activates said effector cells when incubated in the presence of target cells.

In one embodiment, the protein binds an activating receptor on an effector cell and an antigen of interest, and the step (c) comprises:
(i) testing the ability of the polypeptide to induce effector cells that express the activating receptor to lyse target cells (that express antigen of interest), when incubated such effector cells in the presence of target cells. Optionally, step (i) is followed by a step comprising: selecting a protein (e.g., for further development, for use as a medicament) that induces effector cells that express the activating receptor to lyse the target cells, when incubated such effector cells in the presence of the target cells.

In one embodiment, the protein binds an activating receptor on an effector cell and an antigen of interest, and the step (c) comprises:
(i) testing the ability of the protein to activate effector cells that express CD16 but do not express the activating receptor, when incubated with such effector cells in the presence of target cells. Optionally, step (i) is followed by a step comprising: selecting a protein (e.g., for further development, for use as a medicament) that do not substantially activate said effector cells, when incubated with such effector cells in the presence of target cells.

In one aspect provided is a pharmaceutical composition comprising a compound or composition described herein, and a pharmaceutically acceptable carrier.

In one aspect provided is the use of a polypeptide or composition of any one of the above claims as a medicament for the treatment of disease.

In one aspect provided is a method of treating a disease in a subject comprising administering to the subject a compound or composition described herein.

In one embodiment, the disease is a cancer or an infectious disease.

Any of the methods can further be characterized as comprising any step described in the application, including notably in the "Detailed Description of the Invention"). The invention further relates to a protein obtainable by any of present methods. The disclosure further relates to pharmaceutical or diagnostic formulations of the antibodies of the present invention. The disclosure further relates to methods of using antibodies in methods of treatment or diagnosis.

These and additional advantageous aspects and features of the invention may be further described elsewhere herein.

BRIEF DESCRIPTION OF THE FIGURES

FIG. 6A to 6E shows different domain arrangements of bispecific proteins produced.

FIG. 8A (top panel CD107, bottom panel CD69) shows bispecific antibodies having NKp46 and CD19 binding regions in an F2 format protein do not activate resting NK cells in the absence of target cells, however full length anti-NKp46 antibodies as well as positive control alemtuzumab did activate NK cells. FIG. 8B shows that in presence of Daudi target cells, bispecific anti-NKp46×anti-CD19 antibodies (including each of the NKp46-1, NKp46-2, NKp46-3 or NKp46-4 binding domains) activated resting NK cells (top panel CD107, bottom panel CD69), while full-length anti-CD19 showed at best only very low activation of NK cells. Neither full-length anti-NKp46 antibodies or alemtuzmab showed substantial increase in activation beyond what was observed in presence of NK cells alone. FIG. 8C (top panel CD107, bottom panel CD69) shows that in the presence of CD19-negative HUT78 cells, none of the bispecific anti-NKp46×anti-CD19 antibody (including each of the NKp46-1, NKp46-2, NKp46-3 or NKp46-4 variable regions) activated NK cells. However, the full-length anti-NKp46 antibodies and alemtuzumab caused detectable activation of NK cells at a similar level observed in presence of NK cells alone. Isotype control antibody did not induce activation.

FIG. 9 shows that at low effector:target ratio of 1:1 each of the bispecific anti-NKp46×anti-CD19 antibody activated NK cells in the presence of Daudi cells, and that bispecific anti-NKp46×anti-CD19 were far more potent than the anti-CD19 antibody as a full-length human IgG1 as ADCC inducing antibody. Top panel is CD107 and bottom panel shows CD69.

DETAILED DESCRIPTION OF THE INVENTION

Definitions

Figure 1:
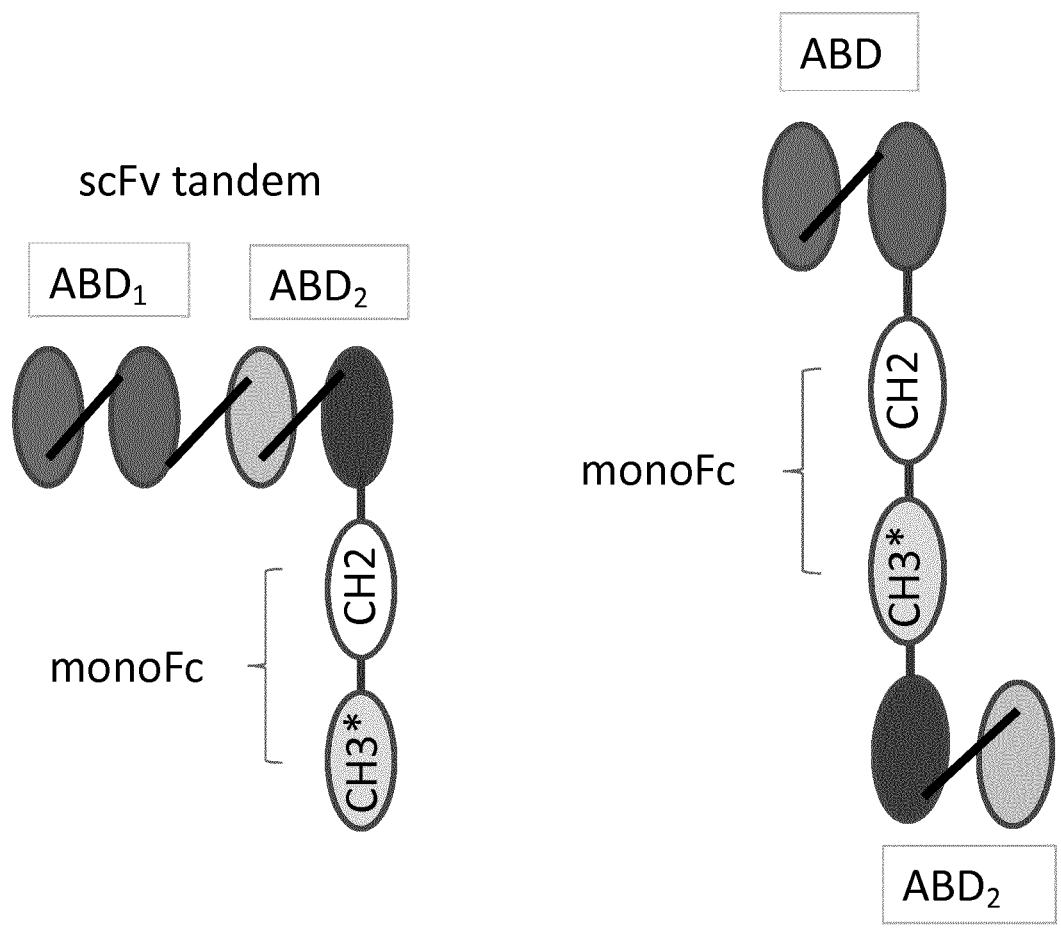
FIG. 1 shows two examples of multispecific polypeptides in which one of the antigen binding domains ($ABD_1$ or $ABD_2$) specifically binds to NKp46 and the other of the ABDs binds to an antigen of interest, wherein the drawing on the left has tandem scFv and the drawing on the right has two ABD with an Fc domain interposed.

As used in the specification, "a" or "an" may mean one or more. As used in the claim(s), when used in conjunction with the word "comprising", the words "a" or "an" may mean one or more than one.

Where "comprising" is used, this can optionally be replaced by "consisting essentially of", more optionally by "consisting of".

As used herein, the term "antigen binding domain" refers to a domain comprising a three-dimensional structure capable of immunospecifically binding to an epitope. Thus, in one embodiment, said domain can comprise a hypervariable region, optionally a VH and/or VL domain of an antibody chain, optionally at least a VH domain. In another embodiment, the binding domain may comprise at least one complementarity determining region (CDR) of an antibody chain. In another embodiment, the binding domain may comprise a polypeptide domain from a non-immunoglobulin scaffold.

The term "antibody" herein is used in the broadest sense and specifically includes full-length monoclonal antibodies, polyclonal antibodies, multispecific antibodies (e.g., bispecific antibodies), and antibody fragments and derivatives, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988). An "antibody fragment" comprises a portion of a full-length antibody, e.g. antigen-binding or variable regions thereof. Examples of antibody fragments include Fab, Fab', F(ab)$_2$, F(ab')$_2$, F(ab)$_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

The term "antibody derivative", as used herein, comprises a full-length antibody or a fragment of an antibody, e.g. comprising at least antigen-binding or variable regions thereof, wherein one or more of the amino acids are chemically modified, e.g., by alkylation, PEGylation, acylation, ester formation or amide formation or the like. This includes, but is not limited to, PEGylated antibodies, cysteine-PEGylated antibodies, and variants thereof.

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

By "constant region" as defined herein is meant an antibody-derived constant region that is encoded by one of the light or heavy chain immunoglobulin constant region genes. By "constant light chain" or "light chain constant region" as used herein is meant the region of an antibody encoded by the kappa (Ckappa) or lambda (Clambda) light chains. The constant light chain typically comprises a single domain, and as defined herein refers to positions 108-214 of Ckappa, or Clambda, wherein numbering is according to the EU index (Kabat et al., 1991, Sequences of Proteins of Immunological Interest, 5th Ed., United States Public Health Service, National Institutes of Health, Bethesda). By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "Fab" or "Fab region" as used herein is meant the polypeptide that comprises the VH, CH1, VL, and CL immunoglobulin domains. Fab may refer to this region in isolation, or this region in the context of a polypeptide, multispecific polypeptide or ABD, or any other embodiments as outlined herein.

By "single-chain Fv" or "scFv" as used herein are meant antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. Methods for producing scFvs are well known in the art. For a review of methods for producing scFvs see Pluckthun in The Pharmacology of Monoclonal Antibodies, vol. 113, Rosenburg and Moore eds. Springer-Verlag, New York, pp. 269-315 (1994).

By "Fv" or "Fv fragment" or "Fv region" as used herein is meant a polypeptide that comprises the VL and VH domains of a single antibody.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cγ2 (CH2) and Cγ3 (CH3) and the hinge between Cγ1 and Cγ2. Although the boundaries of the Fc region may vary, the human IgG heavy chain Fc region is usually defined to comprise residues C226, P230 or A231 to its carboxyl-terminus, wherein the numbering is according to the EU index. Fc may refer to this region in isolation, or this region in the context of an Fc polypeptide, as described below. By "Fc polypeptide" or "Fc-derived polypeptide" as used herein is meant a polypeptide that comprises all or part of an Fc region. Fc polypeptides include but are not limited to antibodies, Fc fusions and Fc fragments.

By "variable region" as used herein is meant the region of an antibody that comprises one or more Ig domains substantially encoded by any of the VL (including Vkappa and Vlambda) and/or VH genes that make up the light chain (including kappa and lambda) and heavy chain immunoglobulin genetic loci respectively. A light or heavy chain variable region (VL and VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

The term "specifically binds to" means that an antibody or polypeptide can bind preferably in a competitive binding assay to the binding partner, as assessed using either recombinant forms of the proteins, epitopes therein, or native proteins present on the surface of isolated target cells. Competitive binding assays and other methods for determining specific binding are further described below and are well known in the art.

The term "affinity", as used herein, means the strength of the binding of an antibody or polypeptide to an epitope. The affinity of an antibody is given by the dissociation constant $K_D$, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant $K_A$ is defined by $1/K_D$. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of surface plasmon resonance (SPR) screening (such as by analysis with a BIAcore™ SPR analytical device).

By "amino acid modification" herein is meant an amino acid substitution, insertion, and/or deletion in a polypeptide sequence. An example of amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of a polypeptide will exhibit 98%, 98%, or 99% homogeneity for polypeptides in the context of all present peptide species in the composition or at least with respect to substantially active peptide species in the context of proposed use.

In the context herein, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

As used herein, "NK cells" refers to a sub-population of lymphocytes that is involved in non-conventional immunity. NK cells can be identified by virtue of certain characteristics and biological properties, such as the expression of specific surface antigens including CD56 and/or NKp46 for human NK cells, the absence of the alpha/beta or gamma/delta TCR complex on the cell surface, the ability to bind to and kill cells that fail to express "self" MHC/HLA antigens by the activation of specific cytolytic machinery, the ability to kill tumor cells or other diseased cells that express a ligand for NK activating receptors, and the ability to release protein molecules called cytokines that stimulate or inhibit the immune response. Any of these characteristics and activities can be used to identify NK cells, using methods well known in the art. Any subpopulation of NK cells will also be encompassed by the term NK cells. Within the context herein "active" NK cells designate biologically active NK cells, including NK cells having the capacity of lysing target cells or enhancing the immune function of other cells. NK cells can be obtained by various techniques known in the art, such as isolation from blood samples, cytapheresis, tissue or cell collections, etc. Useful protocols for assays involving NK cells can be found in Natural Killer Cells Protocols (edited by Campbell K S and Colonna M). Human Press. pp. 219-238 (2000).

As used herein, "T cells" refers to a sub-population of lymphocytes that mature in the thymus, and which display, among other molecules T cell receptors on their surface. T cells can be identified by virtue of certain characteristics and biological properties, such as the expression of specific surface antigens including the TCR, CD4 or CD8, the ability of certain T cells to kill tumor or infected cells, the ability of certain T cells to activate other cells of the immune system, and the ability to release protein molecules called cytokines that stimulate or inhibit the immune response. Any of these characteristics and activities can be used to identify T cells, using methods well known in the art. Within the context herein, "active" or "activated" T cells designate biologically active T cells, more particularly T cells having the capacity of cytolysis or of stimulating an immune response by, e.g., secreting cytokines. Active cells can be detected in any of a number of well-known methods, including functional assays and expression-based assays such as the expression of cytokines such as TNF-alpha.

Producing Polypeptides

The antigen binding domains described herein can be readily derived a variety of immunoglobulin or non-immunoglobulin scaffolds, for example affibodies based on the Z-domain of staphylococcal protein A, engineered Kunitz domains, monobodies or adnectins based on the 10th extracellular domain of human fibronectin III, anticalins derived from lipocalins, DARPins (desiged ankyrin repeat domains, multimerized LDLR-A module, avimers or cysteine-rich knottin peptides. See, e.g., Gebauer and Skerra (2009) Current Opinion in Chemical Biology 13:245-255, the disclosure of which is incorporated herein by reference.

Variable domains are commonly derived from antibodies (immunoglobulin chains), for example in the form of associated VL and VH domains found on two polypeptide chains, or single chain antigen binding domains such as scFv, a $V_H$ domain, a $V_L$ domain, a dAb, a V-NAR domain or a $V_H H$ domain. A variable domain can also be readily derived from antibodies as a Fab.

Typically, antibodies are initially obtained by immunization of a non-human animal, e.g., a mouse, with an immunogen comprising a polypeptide, or a fragment or derivative thereof, typically an immunogenic fragment, for which it is desired to obtain antibodies (e.g. a human polypeptide). The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). Other protocols may also be used as long as they result in the production of B cells expressing an antibody directed to the antigen used in immunization. Lymphocytes from a non-immunized non-human mammal may also be isolated, grown in vitro, and then exposed to the immunogen in cell culture. The lymphocytes are then harvested and the fusion step described below is carried out. For exemplary monoclonal antibodies, the next step is the isolation of splenocytes from the immunized non-human mammal and the subsequent fusion of those splenocytes with an immortalized cell in order to form an antibody-producing hybridoma. The hybridoma colonies are then assayed for the production of antibodies that specifically bind to the polypeptide against which antibodies are desired. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference).

Human antibodies may also be produced by using, for immunization, transgenic animals that have been engineered to express a human antibody repertoire (Jakobovitz et Nature 362 (1993) 255), or by selection of antibody repertoires using phage display methods. For example, a Xeno-Mouse (Abgenix, Fremont, Calif.) can be used for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Antibodies may also be produced by selection of combinatorial libraries of immunoglobulins, as disclosed for instance in (Ward et al. Nature, 341 (1989) p. 544, the entire disclosure of which is herein incorporated by reference). Phage display technology (McCafferty et al (1990) Nature 348:552-553) can be used to produce antibodies from immunoglobulin variable (V) domain gene repertoires from unimmunized donors. See, e.g., Griffith et al (1993) EMBO J. 12:725-734; U.S. Pat. Nos. 5,565,332; 5,573,905; 5,567, 610; 5,229,275). When combinatorial libraries comprise variable (V) domain gene repertoires of human origin, selection from combinatorial libraries will yield human antibodies.

Additionally, a wide range of antibodies are available in the scientific and patent literature, including DNA and/or amino acid sequences, or from commercial suppliers. Antibodies will typically be directed to a pre-determined antigen. Examples of antibodies include antibodies that recognize an antigen expressed by a target cell that is to be eliminated, for example a proliferating cell or a cell contributing to a pathology. Examples include antibodies that recognize tumor antigens, microbial (e.g. bacterial) antigens or viral antigens.

Variable domains and/or antigen binding domains can be selected based on the desired cellular target, and may include for example cancer antigens, bacterial or viral antigens, etc. As used herein, the term "bacterial antigen" includes, but is not limited to, intact, attenuated or killed bacteria, any structural or functional bacterial protein or carbohydrate, or any peptide portion of a bacterial protein of sufficient length (typically about 8 amino acids or longer) to be antigenic. Examples include gram-positive bacterial antigens and gram-negative bacterial antigens. In some embodiments the bacterial antigen is derived from a bacterium selected from the group consisting of *Helicobacter* species, in particular *Helicobacter pyloris*; *Borelia* species, in particular *Borelia burgdorferi*; *Legionella* species, in particular *Legionella pneumophilia*; *Mycobacteria* s species, in particular *M. tuberculosis*, *M. avium*, *M. intracellulare*, *M. kansasii*, *M. gordonae*; *Staphylococcus* species, in particular *Staphylococcus aureus*; *Neisseria* species, in particular *N. gonorrhoeae*, *N. meningitidis*; *Listeria* species, in particular *Listeria monocytogenes*; *Streptococcus* species, in particular *S. pyogenes*, *S. agalactiae*; *S. faecalis*; *S. bovis*, *S. pneumonias*; anaerobic *Streptococcus* species; pathogenic *Campylobacter* species; *Enterococcus* species; *Haemophilus* species, in particular *Haemophilus influenzue*; *Bacillus* species, in particular *Bacillus anthracis*; *Corynebacterium* species, in particular *Corynebacterium diphtheriae*; *Erysipelothrix* species, in particular *Erysipelothrix rhusiopathiae*; *Clostridium* species, in particular *C. perfringens*, *C. tetani*; *Enterobacter* species, in particular *Enterobacter aerogenes*, *Klebsiella* species, in particular *Klebsiella* 1S *pneumoniae*, *Pasteurella* species, in particular *Pasteurella multocida*, *Bacteroides* species; *Fusobacterium* species, in particular *Fusobacterium nucleatum*; *Streptobacillus* species, in particular *Streptobacillus moniliformis*; *Treponema* species, in particular *Treponema pertenue*; *Leptospira*; pathogenic *Escherichia* species; and *Actinomyces* species, in particular *Actinomyces israelli*.

As used herein, the term "viral antigen" includes, but is not limited to, intact, attenuated or killed whole virus, any structural or functional viral protein, or any peptide portion of a viral protein of sufficient length (typically about 8 amino acids or longer) to be antigenic. Sources of a viral antigen include, but are not limited to viruses from the families: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses). Alternatively, a viral antigen may be produced recombinantly.

As used herein, the terms "cancer antigen" and "tumor antigen" are used interchangeably and refer to antigens that are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

The cancer antigens are usually normal cell surface antigens which are either overexpressed or expressed at abnormal times. Ideally the target antigen is expressed only on proliferative cells (e.g., tumour cells), however this is rarely observed in practice. As a result, target antigens are usually selected on the basis of differential expression between proliferative and healthy tissue. Antibodies have been raised to target specific tumour related antigens including: Receptor Tyrosine Kinase-like Orphan Receptor 1 (ROR1), Cripto, CD4, CD20, CD30, CD19, CD38, CD47, Glycoprotein NMB, CanAg, Her2 (ErbB2/Neu), CD22 (Siglec2), CD33 (Siglec3), CD79, CD138, CD171, PSCA, L1-CAM, PSMA (prostate specific membrane antigen), BCMA, CD52, CD56, CD80, CD70, E-selectin, EphB2, Melanotransferrin, Mud 6 and TMEFF2. Examples of cancer antigens also include B7-H3, B7-H4, B7-H6, PD-L1, MAGE, MART-1/Melan-A, gp100, adenosine deaminase-binding protein (ADAbp), cyclophilin b, colorectal associated antigen (CRC)-0017-1A/GA733, Killer-Ig Like Receptor 3DL2 (KIR3DL2), protein tyrosine kinase 7(PTK7), receptor protein tyrosine kinase 3 (TYRO-3), nectins (e.g. nectin-4), major histocompatibility complex class I-related chain A and B polypeptides (MICA and MICB), proteins of the UL16-binding protein (ULBP) family, proteins of the retinoic acid early transcript-1 (RAET1) family, carcinoembryonic antigen (CEA) and its immunogenic epitopes CAP-1 and CAP-2, etv6, aml1, prostate specific antigen (PSA), T-cell receptor/CD3-zeta chain, MAGE-family of tumor antigens, GAGE-family of tumor antigens, anti-Mullerian hormone Type II receptor, delta-like ligand 4 (DLL4), DR5, BAGE, RAGE, LAGE-1, NAG, GnT-V, MUM-1, CDK4, MUC family, VEGF, VEGF receptors, Angiopoietin-2, PDGF, TGF-alpha, EGF, EGF receptor, a member of the human EGF-like receptor family such as HER-2/neu, HER-3, HER-4 or a heterodimeric receptor comprised of at least one HER subunit, gastrin releasing peptide receptor antigen, Muc-1, CA125, αvß3 integrins, α5ß1 integrins, αIIbß3-integrins, PDGF beta receptor, SVE-cadherin, IL-8, hCG, IL-6, IL-6 receptor, IL-15, α-fetoprotein, E-cadherin, α-catenin, ß-catenin and γ-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2, although this is not intended to be exhaustive.

In one embodiment, an ABD, variable domain or pair of complementary variable domains binds to a cancer antigen, a viral antigen, a microbial antigen, or an antigen present on an infected cell (e.g. virally infected) or on a pro-inflammatory immune cell. In one embodiment, said antigen is a polypeptide selectively expressed or overexpressed on a tumor cell, and infected cell or a pro-inflammatory cell. In one embodiment, said antigen is a polypeptide that when inhibited, decreases the proliferation and/or survival of a tumor cell, an infected cell or a pro-inflammatory cell. For example, a first and/or second antibody or fragment can respectively bind anti-Her1 and anti-Her2. Anti-Her2 can be for example an antibody comprising the CDRs derived from Herceptin® (trastuzumab) or 2C4 (pertuzumab). Anti-Her2 and anti-Her1 (antibodies D1-5 and C3-101) amino acid sequences are shown in WO2011/069104.

In one embodiment, an ABD, variable domain or pair of complementary variable domains inhibits (neutralizes) the function of a polypeptide to which it specifically binds. In one embodiment, the first and/or second ABD each inhibits the function of a polypeptide to which they specifically binds. In one embodiment, the polypeptide is a polypeptide selectively expressed or overexpressed on a tumor cell. In one embodiment, the polypeptide is a polypeptide selectively expressed or overexpressed on an infected (e.g. virally or bacterially infected) cell or a pro-inflammatory cell. In one embodiment, the polypeptide is a polypeptide that when inhibited, decreases the proliferation and/or survival of a tumor cell, an infected cell or a pro-inflammatory cell. For example bispecific antibodies that bind ErbB2 and ErbB3 and blocks ligand-induced receptor activation have been reported to be effective in ErbB2-amplified tumors (MacDonagh et al. (2012) Mol. Cancer Ther. 11:582).

In exemplary embodiments, one an ABD, variable domain or pair of complementary variable domains will bind an antigen expressed by a target cell that is to be eliminated (e.g., a tumor antigen, microbial (e.g. bacterial) antigen, viral antigen, or antigen expressed on an immune cell that is contributing to inflammatory or autoimmune disease, and the other ABD, variable domain or pair of complementary variable domains will bind to an antigen expressed on an immune cell, for example an immune effector cell, e.g. a cell surface receptor of an effector cells such as a T or NK cell. Examples of antigens expressed on immune cells, optionally immune effector cells, include antigens expressed on a member of the human lymphoid cell lineage, e.g. a human T cell, a human B cell or a human natural killer (NK) cell, a human monocyte, a human neutrophilic granulocyte or a human dendritic cell. Advantageously, such cells will have either a cytotoxic or an apoptotic effect on a target cell that is to be eliminated (e.g., that expresses a tumor antigen, microbial antigen, viral antigen, or antigen expressed on an immune cell that is contributing to inflammatory or autoimmune disease). Especially advantageously, the human lymphoid cell is a cytotoxic T cell or NK cell which, when activated, exerts a cytotoxic effect on the target cell. According to this embodiment, then, the cytotoxic activity of the human effector cells is recruited. According to another embodiment, the human effector cell is a member of the human myeloid lineage.

Antigens expressed on an immune cell to which antibodies of fragments that make up multispecific antibodies can bind also include NK and/or T cell receptors, e.g. any molecule on the surface of NK cells or T cells, respectively, that can serve to direct the NK or T cell to the intended target cell to be eliminated. Examples include, e.g., members of the immunoglobulin superfamily, members of the killer-cell immunoglobulin-like receptor (KIR) family, the leukocyte immunoglobulin-like receptors (LILR) family, or the lectin family or the NK cell lectin-like receptor family. Activity can be measured for example by bringing target cells and effector cells into contact in presence of the multispecific polypeptide. Optionally the immune cell receptor is an activating receptor, e.g. an activating NK cell or T cell receptor. As used herein, the terms "activating NK cell receptor" and "activating T cell receptor" refers to any molecule on the surface of NK cells or T cells, respectively, that, when stimulated, causes a measurable increase in any property or activity known in the art as associated with NK cell or T cell activity, respectively, such as cytokine (for example IFN-γ or TNF-α) production, increases in intracellular free calcium levels, the ability to lyse target cells in a redirected killing assay as described, e.g. elsewhere in the present specification, or the ability to stimulate NK cell or T cell proliferation, respectively. The term "activating NK receptor" includes but is not limited to DNAX accessory molecule-1 (DNAM-1), 2B4, activating forms of KIR proteins (for example KIR2DS receptors, KIR2DS2, KIR2DS4), NKG2D, NKp30, CD69, NKp80, NKp44, NKp46, IL-2R, IL-12R, IL-15R, IL-18R and IL-21R. In one embodiment, the activating NK cell receptor is a receptor other than an Fcγ receptor. In one embodiment, the activating NK cell receptor is a receptor other than NKp46.

Activation of cytotoxic T cells may occur via binding of the CD3 antigen as effector antigen on the surface of the cytotoxic T cell by a multispecific (e.g. bispecific) polypeptide of this embodiment. The human CD3 antigen is present on both helper T cells and cytotoxic T cells. Human CD3 denotes an antigen which is expressed on T cells as part of the multimolecular T cell complex and which comprises three different chains: CD3-epsilon, CD3-delta and CD3-gamma.

Other effector cell antigens bound by a multispecific polypeptide are the human CD16 antigen, the human CD64, the human CD2 antigen, the human CD28 antigen or the human CD25 antigen. In one embodiment, the effector cell antigen is CD16; such a polypeptide, when having an Fc domain that does not substantially bind inhibitory FcγR, will have CD16 agonist activity without contribution of inhibition from inhibitory FcγR. In other embodiments, the effector cell activating receptor is a receptor other than CD16.

The ABDs or variable domains which are incorporated into the polypeptides can be tested for any desired activity prior to inclusion in a polypeptide. Once appropriate antigen binding domains having desired specificity and/or activity are identified, DNA encoding each variable domain can be placed, in suitable arrangements, in an appropriate expression vector(s), together with DNA encoding any elements such as an enzymatic recognition tag, or CH2 and CH3 domains and any other optional elements (e.g. DNA encoding a linker or hinge region) for transfection into an appropriate host(s). The host is then used for the recombinant production of the polypeptide chains that make up the multispecific polypeptide.

An ABD or variable region derived from an antibody will generally comprise at minimum a hypervariable region sufficient to confer binding activity when present in the multimeric polypeptide. It will be appreciated that an ABD or variable region may comprise other amino acids or functional domains as may be desired, including but not limited to linker elements (e.g. linker peptides, constant domain derived sequences, hinges, or fragments thereof, each of which can be placed between a variable domain and a CH1, CL, CH2 or CH3 domain, or between other domains as needed).

In any embodiment, ABDs or variable regions can be obtained from a humanized antibody in which residues from a complementary-determining region (CDR) of a human antibody are replaced by residues from a CDR of the original antibody (the parent or donor antibody, e.g. a murine or rat antibody) while maintaining the desired specificity, affinity, and capacity of the original antibody. The CDRs of the parent antibody, some or all of which are encoded by nucleic acids originating in a non-human organism, are grafted in whole or in part into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239:1534-1536. An antigen binding domain can thus have non-human hypervariable regions or CDRs and human frameworks region sequences (optionally with back mutations).

Polypeptide chains will be arranged in one or more expression vectors so as to produce the polypeptides having the desired domains operably linked to one another. A host cell chosen for expression of the multispecific polypeptide is an important contributor to the final composition, including, without limitation, the variation in composition of the oligosaccharide moieties decorating the protein in the immunoglobulin CH2 domain. Thus, one aspect of the invention involves the selection of appropriate host cells for use and/or development of a production cell expressing the desired therapeutic protein such that the multispecific polypeptide retains at least partial FcRn binding but with decreased binding to a Fcγ receptor compared, e.g., to a wild type full length human IgG1 antibody. The host cell may be of mammalian origin or may be selected from COS-1, COS-7, HEK293, BHK21, CHO, BSC-1, Hep G2, 653, SP2/0, 293, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as natural or engineered *E. coli* spp., *Klebsiella* spp., or *Pseudomonas* spp.

The polypeptide can then be produced in an appropriate host cell or by any suitable synthetic process and brought into contact under appropriate conditions for the multimeric (e.g. dimeri or trimer) polypeptide to form.

Polypeptide Configurations

An isolated hetero-multimeric polypeptide that binds a first and second antigen of interest in monovalent fashion can be prepared according to different configurations, in each case involving at least a central (first) polypeptide chain and a second polypeptide chain, and optionally a third polypeptide chain.

The first (central) polypeptide chain will provide one variable domain that will, together with a complementary variable domain on a second polypeptide chain, form an antigen binding domain specific for one (e.g. a first) antigen of interest. The first (central) polypeptide chain will also provide a second variable domain that will be paired with a complementary variable domain to form an antigen binding domain specific for another (e.g. a second) antigen of interest; the variable domain that is complementary to the second variable domain can be placed on the central polypeptide (e.g. adjacent to the second variable domain in a tandem variable domain construct such as an scFv), or can be placed on the second polypeptide chain, or can be placed on a third polypeptide chain. The second (and third, if present) polypeptide chains will associate with the central polypeptide chain by CH1-CK heterodimerization, forming interchain disulfide bonds between respective hinge domains and between complementary CH1 and CK domains, with a single multimeric polypeptide being formed so long as CH/CK and VH/VK domains are chosen to give rise to a sole dimerization configuration. In a trimer, or when polypeptides are constructed for preparation of a trimer, there will generally be one polypeptide chain that comprises a non-naturally occurring VH-CK or VL-CH1 domain arrangement.

The first (central) polypeptide chain comprises a first variable domain (V) fused to a CH1 of CL constant region (e.g. the V domain is fused at its C-terminus to the N-terminus of a CH1 or CK constant region), a second variable domain, and an Fc domain (e.g. a full Fc domain or a portion thereof) interposed between the first and second variable domains may have the Examples of domain arrangement for the first polypeptide include but are not limited to:

scFv-Fc domain-VH-CH1
scFv-Fc domain-VK-CK
scFv-Fc domain-VK-CH1
scFv-Fc domain-VH-CK
(VH or VK)-Fc domain-VH-CH1
(VH or VK)-Fc domain-VK-CK
(VH or VK)-Fc domain-VK-CH1
(VH or VK)-Fc domain-VH-CK
(VH or VK)-CH1-Fc domain-VH-CH1
(VH or VK)-CK-Fc domain-VK-CK
(VH or VK)-CK-Fc domain-VK-CH1
(VH or VK)-CH1-Fc domain-VH-CK
(VH or VK)-CH1-Fc domain-VK-CH1
(VH or VK)-CK-Fc domain-VH-CK
(VH or VK)-CK-Fc domain-VH-CH1
(VH or VK)-CH1-Fc domain-VK-CK
VH-CH1-Fc domain-scFv
VK-CK-Fc domain-scFv
VH-CK-Fc domain-scFv
VK-CH1-Fc domain-scFv
VH-CH1-Fc domain-(VH or VK)
VK-CK-Fc domain-(VH or VK)
VH-CK-Fc domain-(VH or VK)
VK-CH1-Fc domain-(VH or VK)
VH-CH1-Fc domain-CH1-(VH or VK)
VK-CK-Fc domain-CH1-(VH or VK)
VH-CK-Fc domain-CH1-(VH or VK)
VK-CH1-Fc domain-CH1-(VH or VK)
VH-CH1-Fc domain-CK-(VH or VK)
VK-CK-Fc domain-CK-(VH or VK)
VH-CK-Fc domain-CK-(VH or VK)
VK-CH1-Fc domain-CK-(VH or VK)

A second polypeptide chain comprises a first variable domain (V) fused (e.g. at its C-terminus) to a CH1 or CL (e.g. CK) constant region selected to be complementary to the CH1 or CL constant region of the first polypeptide chain such that the first and second polypeptides form a CH1-CL (e.g., CH1-CK) heterodimer. The second polypeptide chain may further comprises an Fc domain (e.g. a full Fc domain or a portion thereof), e.g., fused to the C-terminus of the of the CH1 or CL domain or fused to the N-terminus of the variable domain. Examples of domain arrangement for the second polypeptide include but are not limited to:

(VH or VK)-(CH1)
(VH or VK)-(CK)
Fc domain-(VH or VK)-(CH1)
Fc domain-(VH or VK)-(CK)
(VH or VK)-(CH1)-Fc domain
(VH or VK)-(CK)-Fc domain
(VH or VK)-Fc domain-(VH or VK)-(CH1)
(VH or VK)-Fc domain-(VH or VK)-(CK)

A third polypeptide chain, when present, can have the domain arrangement: (VH or VK)-(CH1 or (CK).

Heterodimers

Examples of the domain arrangements (N- to C-terminal) of central polypeptide chains for use in such heterodimeric proteins include:

$V_{a1}$-(CH1 or CK)$_a$—Fc domain-$V_{a2}$-$V_{b2}$;

$V_{a2}$-$V_{b2}$-Fc domain-$V_{a1}$-(CH1 or CK)$_a$ wherein $V_{a1}$ is a light chain or heavy chain variable domain, and wherein one of $V_{a2}$ and $V_{b2}$ is a light chain variable domain and the other is a heavy chain variable domain.

Further examples include:

$V_{a1}$-(CH1 or CK)$_a$—Fc domain-$V_b$;

$V_b$-Fc domain-$V_{a2}$-(CH1 or CK)$_a$ wherein $V_b$ binds antigen as a single variable domain (e.g. dAb, VhH).

The Fc domain of the central chain may be a full Fc domain (CH2-CH3) or a portion thereof sufficient to confer the desired functionality (e.g. FcRn binding). A second polypeptide chain will then be configured which will comprise an immunoglobulin variable domain and a CH1 or CK constant region, e.g., a (CH1 or CK)$_b$ unit, selected so as to permit CH1-CK heterodimerization with the central polypeptide chain; the immunoglobulin variable domain will be selected so as to complement the variable domain of the central chain that is adjacent to the CH1 or CK domain, whereby the complementary variable domains form an antigen binding domain for a first antigen of interest.

For example, a second polypeptide chain can comprise a domain arrangement:

$V_{b1}$-(CH1 or CK)$_b$, or $V_{b1}$-(CH1 or CK)$_b$—Fc domain such that the (CH1 or CK)$_b$ dimerizes with the (CH1 or CK)$_a$ on the central chain, and the $V_{b1}$ forms an antigen binding domain together with $V_{a1}$ of the central chain. If $V_{a1}$ of the central chain is a light chain variable domain, $V_{b1}$ will be a heavy chain variable domain; and if $V_{a1}$ of the central chain is a heavy chain variable domain, $V_b$, will be a light chain variable domain.

The antigen binding domain for the second antigen of interest can then be formed from $V_{a2}$ and $V_{b2}$ which are configured as tandem variable domains on the central chain forming the antigen binding domain for the second antigen of interest (e.g. a heavy chain variable domain (VH) and a light chain (kappa) variable domain (VK), for example forming an scFv unit). The antigen binding domain for the second antigen of interest can also alternatively be formed from a single variable domain $V_2$ present on the central chain.

The resulting heterodimer can for example have the configuration as follows (see also Examples of such proteins shown as formats 2, 11 and 12 shown in FIGS. 6A and 6C):

$V_{a2}$-$V_{b2}$-Fc domain-$V_{a1}$-(CH1 or CK)$_a$     (first/central polypeptide chain)
| 
$V_{b1}$-(CH1 or CK)$_b$     (second polypeptide chain)

wherein one of $V_{a1}$ of the first polypeptide chain and $V_{b1}$ of the second polypeptide chain is a light chain variable domain and the other is a heavy chain variable domain, and wherein one of $V_{a2}$ and $V_{b2}$ is a light chain variable domain and the other is a heavy chain variable domain.

The resulting heterodimer can in another example have the configuration as follows (see also Examples of such proteins shown as format 10 shown in FIG. 6B):

$V_{a1}$-(CH1 or CK)$_a$-Fc domain-$V_{a2}$-$V_{b2}$     (first/central polypeptide chain)
|
$V_{b1}$-(CH1 or CK)$_b$     (second polypeptide chain)

wherein one of $V_{a1}$ of the first polypeptide chain and $V_{b1}$ of the second polypeptide chain is a light chain variable domain and the other is a heavy chain variable domain, and wherein one of $V_{a2}$ and $V_{b2}$ is a light chain variable domain and the other is a heavy chain variable domain.

The resulting heterodimer can in another example have the configuration as follows (see also Examples of such proteins shown as formats 13 and 14 shown in FIGS. 6D and 6E):

$V_{a1}$-(CH1 or CK)$_a$-Fc domain-$V_{a2}$-$V_{b2}$     (first/central polypeptide chain)
|
$V_{b1}$-(CH1 or CK)$_b$-Fc domain     (second polypeptide chain)

wherein one of $V_{a1}$ of the first polypeptide chain and $V_{b1}$ of the second polypeptide chain is a light chain variable domain and the other is a heavy chain variable domain, and wherein one of $V_{a2}$ and $V_{b2}$ is a light chain variable domain and the other is a heavy chain variable domain.

In one embodiment, the heterodimeric bispecific Fc-derived polypeptide comprises a domain arrangement of one of the following, optionally wherein one or both hinge domains are replaced by a peptide linker, optionally wherein the Fc domain is fused via a peptide linker to an scFv that binds a polypeptide expressed by an immune effector cell (e.g. T cell, NK cell, etc.):

(VH-CH1-hinge)-Fc domain-(anti-effector cell scFv)    or
|
(VK-CK)
(VK-CK-hinge)-Fc domain-(anti- effector cell scFv)    or
|
(VH-CH1-hinge)
(VK-CK-hinge)-Fc domain-(anti-effector cell scFv)    or
|
(VH-CH1-hinge)-Fc domain
(VH-CH1-hinge)-Fc domain-(anti- effector cell scFv)    or
|
(VK-CK-hinge)-Fc domain
(VH-CH1-hinge)-Fc domain
|
(VK-CK-hinge)-Fc domain-(anti- effector cell scFv)

Examples of domain arrangement for the dimeric polypeptide formed include but are not limited to those in the table below:

VK-VH-Fc domain-VH-(CH1)
|
VK-(CK)

VH-VK-Fc domain-VH-(CH1)
|
VK-(CK)

VK-VH-Fc domain-VK-(CH1)
|
VH-(CK)

VH-VK-Fc domain-VK-(CH1)
|
VH-(CK)

VH-VK-Fc domain-VH-(CK)
|
VK-(CH1)

VH-VK-Fc domain-VK-(CK)
|
VH-(CH1)

VK-VH-Fc domain-VH-(CH1)
|
Fc domain-VK-(CK)

VH-VK-Fc domain-VH-(CH1)
|
Fc domain-VK-(CK)

VK-VH-Fc domain-VK-(CH1)
|
Fc domain-VH-(CK)

VH-VK-Fc domain-VK-(CH1)
|
Fc domain-VH-(CK)

VH-(CH1)-Fc domain-VH-VK
|
VK-(CK)-Fc domain

VH-(CH1)-Fc domain-VK-VH
|
VK-(CK)-Fc domain

VK-(CH1)-Fc domain-VH-VK
|
VH-(CK)-Fc domain

VK-(CH1)-Fc domain-VK-VH
|
VH-(CK)-Fc domain

Heterotrimers

Heterotrimeric proteins can for example be formed by using a central (first) polypeptide chain comprising a first variable domain (V) fused to a first CH1 or CK constant region, a second variable domain (V) fused to a second CH1 or CK constant region, and an Fc domain or portion thereof interposed between the first and second variable domains (i.e. the Fc domain is interposed between the first and second (V-(CH1/CK)) units. For example, a central polypeptide chain for use in a heterotrimeric protein can have the domain arrangements (N- to C-terminal) as follows:

$V_{a1}$-(CH1 or CK)$_a$-Fc domain-$V_{a2}$-(CH1 or CK)$_b$.

A second polypeptide chain can then comprise a domain arrangement (N- to C-terminal):

$V_{b1}$-(CH1 or CK)$_c$, or $V_{b1}$-(CH1 or CK)$_c$—Fc domain such that the (CH1 or CK)$_c$ dimerizes with the (CH1 or CK)$_a$ on the central chain, and the $V_{a1}$ and $V_{b1}$ form an antigen binding domain.

A third polypeptide chain can then comprise a domain arrangement (N- to C-terminal):

$V_{b2}$-(CH1 or CK)$_d$, such that the (CH1 or CK)$_d$ dimerizes with the (CH1 or CK)$_b$ unit on the central chain, and the $V_{a1}$ and $V_{b2}$ form an antigen binding domain.

An example of a configuration of a resulting heterotrimer with a dimeric Fc domain (also shown as formats 5, 6, 7 and 16 in FIGS. 6D and 6E) has a domain arrangement:

$V_{b1}$-(CH1 or CK)$_c$-Fc domain    (second polypeptide)
|
$V_{a1}$-(CH1 or CK)$_a$-Fc domain-$V_{a2}$-(CH1 or CK)$_b$    (first polypeptide)
|
$V_{b2}$-(CH1 or CK)$_d$    (third polypeptide)

An example of a configuration of a resulting heterotrimer with a monomeric Fc domain (also shown as formats 8, 9 and 17 in FIGS. 6B and 6C) has a domain arrangement:

$V_{b1}$-(CH1 or CK)$_c$    (second polypeptide)
|
$V_{a1}$-(CH1 or CK)$_a$-Fc domain-$V_{a2}$-(CH1 or CK)$_b$    (first polypeptide)
|
$V_{b2}$-(CH1 or CK)$_d$    (third polypeptide)

Thus, in a configuration of a trimer polypeptide, the first polypeptide can have two variable domains that each form an antigen binding domain with a variable domain on a separate polypeptide chain (i.e. the variable domain of the second and third chains), the second polypeptide chain has one variable domain, and the third polypeptide has one variable domain.

A trimeric polypeptide may comprise:
(a) a first polypeptide chain comprising a first variable domain (V) fused to a first CH1 of CK constant region, a second variable domain (V) fused to a second CH1 of CK constant region, and an Fc domain or portion thereof interposed between the first and second variable domains;
(b) a second polypeptide chain comprising a variable domain fused at its C-terminus to a CH1 or CK constant region selected to be complementary to the first CH1 or CK constant region of the first polypeptide chain such that the first and second polypeptides form a CH1-CK heterodimer, and optionally an Fc domain; and
(c) a third polypeptide chain comprising a variable domain fused (e.g. at its C-terminus) to a CH1 or CK constant region, wherein the variable domain and the constant region are selected to be complementary to the second variable domain and second CH1 or CK constant region of the first polypeptide chain such that the first and third polypeptides form a CH1-CK heterodimer bound by disulfide bond(s) formed between the CH1 or CK constant region of the third polypeptide and the second CH1 or CK constant region of the first polypeptide, but not between the CH1 or CK constant region of the third polypeptide and the first CH1 or CK constant region of the first polypeptide wherein the first, second and third polypeptides form a CH1-CK heterotrimer, and wherein the first variable domain of the first polypeptide chain and the variable domain of the second polypeptide chain form an antigen binding domain specific for a first antigen of interest, and the second variable domain of the first polypeptide chain and the variable domain on the third polypeptide chain form an antigen binding domain specific for a second antigen of interest.

Examples of domain arrangement for the trimeric bispecific polypeptide formed from include but are not limited to:

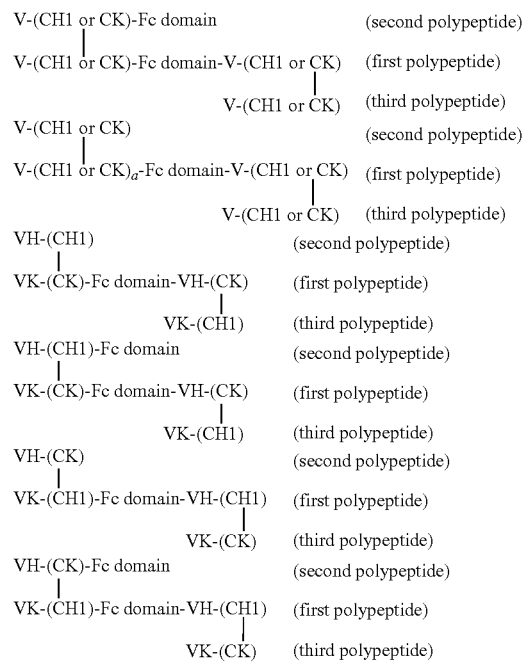

A hinge region will typically be present on a polypeptide chain between a CH1 domain and a CH2 domain, and/or can be present between a CK domain and a CH2 domain. A hinge region can optionally be replaced for example by a suitable linker peptide.

The proteins domains described in the present disclosure can optionally be specified as being from N- to C-terminal. Protein arrangements of the disclosure for purposes of illustration are shown from N-terminus (on the left) to C-terminus. Domains can be referred to as fused to one another (e.g. a domain can be said to be fused to the C-terminus of the domain on its left, and/or a domain can be said to be fused to the N-terminus of the domain on its right).

The proteins domains described in the present disclosure can be fused to one another directly or via intervening amino acid sequences. For example, a CH1 or CK domain will be fused to an Fc domain (or CH2 or CH3 domain thereof) via a linker peptide, optionally a hinge region or a fragment thereof. In another example, a VH or VK domain will be fused to a CH3 domain via a linker peptide. VH and VL domains linked to another in tandem will be fused via a linker peptide (e.g. as an scFv). VH and VL domains linked to an Fc domain will be fused via a linker peptide. Two polypeptide chains will be bound to one another (indicated by "|"), preferably by interchain disulfide bonds formed between cysteine residues within complementary CH1 and CK domains.

It will be appreciated that in any embodiment herein, a VK domain can be replaced by a Vλ variable domain.

In any of the domain arrangements, the Fc domain may comprise a CH2-CH3 unit (a full length CH2 and CH3 domain or a fragment thereof). In heterodimers or heterotrimers comprising two chains with Fc domains (a dimeric Fc domain), the CH3 domain will be capable of CH3-CH3 dimerization (e.g. a wild-type CH3 domain). In heterodimers or heterotrimers comprising only one chain with an Fc domain (monomeric Fc domain), the Fc domain will be incapable of CH3-CH3 dimerization; for example the CH3 domain(s) will have amino acid modification(s) in the CH3 dimer interface or the Fc domain will comprise a tandem CH3 domain incapable of CH3-CH3 dimerization. In one embodiment of any aspect herein, a first CH3 domain is connected to a second CH3 domain by a linker. The tandem CH3 domain may have the domain arrangement, from N-terminus to C-terminus, as follows:

CH3-linker-CH3-.

The linker in the tandem CH3 domain will be a flexible linker (e.g. peptide linker). In one embodiment the linker permits the CH3 domains to associate with one another by non-covalent interactions. In one embodiment, the linker is a peptide linker having 10-50 amino acid residues. In one embodiment, the linker has the formula $(G_4S)_x$. Optionally, x is 2, 3, 4, 5 or 6. In any of the embodiments, each CH3 domain is independently a full-length and/or native CH3 domain, or a fragment or modified CH3 domain which retains a functional CH3 dimerization interface.

An exemplary tandem CH3 with a flexible peptide linker (underlined) is shown below. An exemplary tandem CH3 domain can thus comprise an amino acid sequence of SEQ ID NO: 2, or a sequence at least 70%, 80%, 90%, 95% or 98% identical thereto:

```
                                          (SEQ ID NO: 2)
     G Q P R E P Q V Y T L P P S R E E M T K N Q V

S L T C L V K G F Y P S D I A V E W E S N G Q P E

N N Y K T T P T P P V L D S D G S F F L Y S K L T

V D K S R W Q Q G N V F S C S V M H E A L H N H Y

T Q K S L S L S P G G G G G S G G G G S G G G G S

G Q P R E P Q V Y T L P P S R E E M T K N Q V S L

T C L V K G F Y P S D I A V E W E S N G Q P E N N

Y K T T P T P P V L D S D G S F F L Y S K L T V D

K S R W Q Q G N V F S C S V M H E A L H N H Y T Q

K S L S L S P G
```

Tandem CH3 domains disclosed herein and CH3 domains with amino acid modification to prevent CH3-CH3 dimerization will retain partial FcRn binding (compared, e.g., to a wild type full length human IgG1 antibody). The examples of monomeric CH2-CH3 domains provided herein retain partial FcRn binding but have decreased human Fcγ receptor binding. Optionally the multimeric polypeptide is capable of binding to human FcRn with intermediate affinity, e.g. retains binding to FcRn but has decreased binding to a human FcRn receptor compared to a full-length wild type human IgG1 antibody. The Fc moiety may further comprise one or more amino acid modifications, e.g. in the CH2 domain, that decreases further (e.g. abolishes) binding to one or more Fcγ receptors.

The multimeric polypeptides with monomeric Fc domains can advantageously comprise a CH2 domain and a CH3 domain, wherein said CH3 domain comprises a modified CH3 dimer interface (e.g. a mutations in the CH3 dimer interface) to prevent dimerization with another Fc-derived polypeptide. In one embodiment a CH2-CH3 portion comprising a CH3 domain modified to prevent homodimer formation comprises an amino acid sequence of SEQ ID NO: 1, or a sequence at least 90, 95% or 98% identical thereto: APELLGGPSVFLFPPKPKDTLMISRTPE-VTCVVVDVSHEDPEVKFNWYVDGVEVHNAKTKP REEQYN-STYRVVSVLTVLHQDWLNGKEYKCKVSNKALPA-PIEKTISKAKGQPREPQVYTLP PSREEMTKNQVSLT-CLVKGFYPSDIAVEWESNGQPENNYKTTPPVLDSDG SFFLTSKLTVD KSRWQQGNVFSCSVMHEALHN-HYTQKSLSLSPG (SEQ ID NO: 1), optionally comprising a substitution at 1, 2, 3, 4, 5, 6 of residues 121, 136, 165, 175, 177 or 179 of SEQ ID NO: 1.

In one embodiment of any of the polypeptides or methods herein, the CH3 domain comprises an amino acid substitution at 1, 2, 3, 4, 5, 6 or 7 of the positions L351, T366, L368, P395, F405, T407 (or Y407) and/or K409 (EU numbering as in Kabat).

In one embodiment, a peptide linker used to link a variable domain to a CH2 or CH3 comprises a fragment of a CH1 domain and/or hinge region. For example, a N-terminal amino acid sequence of CH1 can be fused to a variable domain in order to mimic as closely as possible the natural structure of an antibody. In one embodiment, the linker comprises a N-terminal CH1 amino acid sequence of between 2-4 residues, between 2-4 residues, between 2-6 residues, between 2-8 residues, between 2-10 residues, between 2-12 residues, between 2-14 residues, between 2-16 residues, between 2-18 residues, between 2-20 residues, between 2-22 residues, between 2-24 residues, between 2-26 residues, between 2-28 residues, or between 2-30 residues. In one embodiment linker comprises or consists of the amino acid sequence RTVA.

When two variable regions form a scFv they are linked together by a linker of sufficient length to enable the ABD to fold in such a way as to permit binding to the antigen for which the ABD is intended to bind. Examples of linkers include, for example, linkers comprising glycine and serine residues, e.g., the amino acid sequence GEGTSTGS $(G_2S)_2$GGAD. In another specific embodiment, the VH domain and VL domains of an svFv are linked together by the amino acid sequence $(G_4S)_3$.

Any of the peptide linkers may comprise a length of at least 5 residues, at least 10 residues, at least 15 residues, at least 20 residues, at least 25 residues, at least 30 residues or more. In other embodiments, the linkers comprises a length of between 2-4 residues, between 2-4 residues, between 2-6 residues, between 2-8 residues, between 2-10 residues, between 2-12 residues, between 2-14 residues, between 2-16 residues, between 2-18 residues, between 2-20 residues, between 2-22 residues, between 2-24 residues, between 2-26 residues, between 2-28 residues, or between 2-30 residues.

Constant region domains can be derived from any suitable antibody. Of particular interest are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat. By "hinge" or "hinge region" or "antibody hinge region" is meant the flexible polypeptide comprising the amino acids between the first and second constant domains of an antibody. Structurally, the IgG CH1 domain ends at EU position 220, and the IgG CH2 domain begins at residue EU position 237. Thus for IgG the hinge is herein defined to include positions 221 (D221 in IgG1) to 236 (G236 in IgG1), wherein the numbering is according to the EU index as in Kabat. References to amino acid residue within constant region domains found within the polypeptides shall be, unless otherwise indicated or as otherwise dictated by context, with reference to Kabat, in the context of an IgG antibody. CH3 domains that can serve in the present antibodies can be derived from any suitable antibody. Such CH3 domains can serve as the basis for a modified CH3 domain. Optionally the CH3 domain is of human origin.

In certain embodiments herein where a multimeric polypeptide comprises a monomeric Fc domain, the CH3 domain will comprise one or more amino acid modifications (e.g. amino acid substitutions) to disrupt the CH3 dimerization interface. Optionally the CH3 domain modifications will prevent protein aggregation caused by the exposure of hydrophobic residues when the CH2-CH3 domains are in monomeric form. Optionally, the CH3 domain modifications will additionally not interfere with the ability of the Fc-derived polypeptide to bind to neonatal Fc receptor (FcRn), e.g. human FcRn.

CH3 domains that can be used to prevent CH3-CH3 dimerization have been described in various publications. See, e.g. US 2006/0074225, WO2006/031994, WO2011/063348 and Ying et al. (2012) J. Biol. Chem. 287(23): 19399-19407, the disclosures of each of which are incorporated herein by reference. In order to discourage the homodimer formation, one or more residues that make up the CH3-CH3 interface are replaced with a charged amino acid such that the interaction becomes electrostatically unfavorable. For example, WO2011/063348 provides that a positive-charged amino acid in the interface, such as lysine, arginine, or histidine, is replaced with a different (e.g. negative-charged amino acid, such as aspartic acid or glutamic acid), and/or a negative-charged amino acid in the interface is replaced with a different (e.g. positive charged) amino acid. Using human IgG as an example, charged residues within the interface that may be changed to the opposing charge include R355, D356, E357, K370, K392, D399, K409, and K439. In certain embodiments, two or more charged residues within the interface are changed to an opposite charge. Exemplary molecules include those comprising K392D and K409D mutations and those comprising D399K and D356K mutations. In order to maintain stability of the Fc domain in monomeric form, one or more large hydrophobic residues that make up the CH3-CH3 interface are replaced with a small polar amino acid. Using human IgG as an example, large hydrophobic residues of the CH3-CH3 interface include Y349, L351, L368, L398, V397, F405, and Y407. Small polar amino acid residues include asparagine, cysteine, glutamine, serine, and threonine. Thus in one embodiment, a CH3 domain will comprise an amino acid modification (e.g. substitution) at 1, 2, 3, 4, 5, 6, 7 or 8 of the positions R355, D356, E357, K370, K392, D399, K409, and K439. In WO2011/063348, two of the positively charged Lys residues that are closely located at the CH3 domain interface were mutated to Asp. Threonine scanning mutagenesis was then carried out on the structurally conserved large hydrophobic residues in the background of these two Lys to Asp mutations. Fc molecules comprising K392D and K409D mutations along with the various substitutions with threonine were analyzed for monomer formation. Exemplary monomeric Fc domains include those having K392D, K409D and Y349T substitutions and those having K392D, K409D and F405T substitutions.

In Ying et al. (2012) J. Biol. Chem. 287(23):19399-19407, amino acid substitutions were made within the CH3 domain at residues L351, T366, L368, P395, F405, T407 and K409. Combinations of different mutations resulted in the disruption of the CH3 dimerization interface, without causing protein aggregation. Thus in one embodiment, a CH3 domain will comprise an amino acid modification (e.g. substitution) at 1, 2, 3, 4, 5, 6 or 7 of the positions L351, T366, L368, P395, F405, T407 and/or K409. In one embodiment, a CH3 domain will comprise amino acid modifications L351Y, T366Y, L368A, P395R, F405R, T407M and K409A. In one embodiment, a CH3 domain will comprise amino acid modifications L351S, T366R, L368H, P395K, F405E, T407K and K409A. In one embodiment, a CH3 domain will comprise amino acid modifications L351K, T366S, P395V, F405R, T407A and K409Y.

CH2 domains can be readily obtained from any suitable antibody. Optionally the CH2 domain is of human origin. A CH2 may or may not be linked (e.g. at its N-terminus) to a hinge of linker amino acid sequence. In one embodiment, a CH2 domain is a naturally occurring human CH2 domain of IgG1, 2, 4 or 4 subtype. In one embodiment, a CH2 domain is a fragment of a CH2 domain (e.g. at least 10, 20, 30, 40 or 50 amino acids).

In one embodiment, a CH2 domain, when present in a polypeptide described herein, will retain binding to a neonatal Fc receptor (FcRn), particularly human FcRn.

In one embodiment, a CH2 domain, when present in a polypeptide described herein, and the polypeptides described herein, will confer decreased or lack of binding to a Fcγ receptor, notably FcγRIIIA (CD16). Polypeptides that comprise a CH2 domain that are not bound by CD16 will not be capable of activating or mediating ADCC by cells (e.g. NK cells, T cells) that do not express the effector cell antigen of interest (e.g. NKp46, CD3, etc.).

In one embodiment, the polypeptides described herein and their Fc domain(s) and/or a CH2 domain thereof, will have decreased or will substantially lack antibody dependent cytotoxicity (ADCC), complement dependent cytotoxicity (CDC), antibody dependent cellular phagocytosis (ADCP), FcR-mediated cellular activation (e.g. cytokine release through FcR cross-linking), and/or FcR-mediated platelet activation/depletion, as mediated by immune cells (e.g. effector cells) that do not express the antigen of interest.

In one embodiment, a CH2 domain in a polypeptide will have substantial loss of binding to activating Fcγ receptors, e.g., FcγRIIIA (CD16), FcγRIIA (CD32A) or CD64, or to an inhibitory Fc receptor, e.g., FcγRIIB (CD32B). In one embodiment, a CH2 domain in a polypeptide will furthermore have substantial loss of binding to the first component of complement (C1q).

For example, substitutions into human IgG1 of IgG2 residues at positions 233-236 and IgG4 residues at positions 327, 330 and 331 were shown to greatly reduce binding to Fcγ receptors and thus ADCC and CDC. Furthermore, Idusogie et al. (2000) J Immunol. 164(8):4178-84 demonstrated that alanine substitution at different positions, including K322, significantly reduced complement activation.

In one embodiment, a CH2 domain that retains binding to a Fcγ receptor but has reduction of binding to Fcγ receptors will lack or have modified N-linked glycosylation, e.g. at residue N297 (Kabat EU). For example the polypeptide is expressed in a cell line which naturally has a high enzyme activity for adding fucosyl to the N-acetylglucosamine that binds to the Fc region of the polypeptides, or which does not yield glycosylation at N297 (e.g. bacterial host cells). In another embodiment, a polypeptide may have one or more substitution that result in lack of the canonical Asn-X-Ser/Thr N-linked glycosylation motif at residues 297-299, which can also thus also result in reduction of binding to Fcγ receptors. Thus, a CH2 domain may have a substitution at N297 and/or at neighboring residues (e.g. 298, 299).

In one embodiment, an Fc domain or a CH2 domain therefrom is derived from an IgG2 Fc mutant exhibiting diminished FcγR binding capacity but having conserved FcRn binding. In one aspect, the IgG2 Fc mutant or the derived multispecific polypeptide, Fc domain or CH2 domain comprises the mutations V234A, G237A, P238S according to the EU numbering system. In another aspect, the IgG2 Fc mutant or the derived multispecific polypeptide or Fc domain comprises mutations V234A, G237A, H268Q or H268A, V309L, A330S, P331S according to the EU numbering system. In a particular aspect, the IgG2 Fc mutant or the derived multispecific polypeptide or Fc domain comprises mutations V234A, G237A, P238S, H268A, V309L, A330S, P331S, and, optionally, P233S according to the EU numbering system. Optionally, a CH2 domain with loss of binding to Fcγ receptors may comprises residues 233, 234, 235, 237, and 238 (EU numbering system) that comprise a sequence selected from PAAAP, PAAAS, and SAAAS, optionally an Fc domain having such mutations can further comprise mutations H268A or H268Q, V309L, A330S and P331S (see WO2011/066501, the disclosure of which is incorporated herein by reference).

In one embodiment, a CH2 domain that loses binding to a Fcγ receptor will comprise at least one amino acid modification (for example, possessing 1, 2, 3, 4, 5, 6, 7, 8, 9, or more amino acid modifications) in the CH2 domain of the Fc region, optionally further in combination with one or more amino acid modification in other domains (e.g. in a hinge domain or a CH3 domain). Any combination of Fc modifications can be made, for example any combination of different modifications disclosed in Armour K L. et al., (1999) Eur J Immunol. 29(8):2613-24; Presta, L. G. et al. (2002) Biochem. Soc. Trans. 30(4):487-490; Shields, R. L. et al. (2002) J. Biol. Chem. 26; 277(30):26733-26740 and Shields, R. L. et al. (2001) J. Biol. Chem. 276(9):6591-6604). In one embodiment, a polypeptide of the invention that has decreased binding to a human Fcγ receptor will comprise at least one amino acid modification (for example, possessing 1, 2, 3, 4, 5, 6, 7, 8, 9, or more amino acid modifications) relative to a wild-type CH2 domain within amino acid residues 237-340 (EU numbering), such that the polypeptide comprising such CH2 domain has decreased affinity for a human Fcγ receptor of interest relative to an equivalent polypeptide comprising a wild-type CH2 domain, optionally wherein the variant CH2 domain comprises a substitution at any one or more of positions 233, 234, 235, 236, 237, 238, 268, 297, 238, 299, 309, 327, 330, 331 (EU numbering).

In one aspect, provided is an isolated multispecific F2 to F17 heterodimeric protein comprising a first polypeptide chain comprising a first amino acid sequence which is at least 50%, 60%, 70%, 80%, 85%, 90%, 95% or 98% identical to the sequence of a first polypeptide chain of a F2 to F17 polypeptides disclosed herein; and a second amino acid sequence which is at least 50%, 60%, 70%, 80%, 85%, 90%, 95% or 98% identical to the sequence of a second polypeptide chain of the respective F2 to F17 polypeptide disclosed herein. Optionally any or all of the variable regions or CDRs of the first and second chains are substituted with different variable regions, optionally where variable regions are excluded from the sequences that are considered for computing identity.

In one aspect, provided is an isolated multispecific heterotrimeric protein comprising a first polypeptide chain comprising a first amino acid sequence which is at least 50%, 60%, 70%, 80%, 85%, 90%, 95% or 98% identical to the sequence of a first polypeptide chain of the F2 to F17 polypeptides disclosed herein; a second amino acid sequence which is at least 50%, 60%, 70%, 80%, 85%, 90%, 95% or 98% identical to the sequence of a second polypeptide chain of the respective F2 to F17 polypeptide disclosed herein; and a third amino acid sequence which is at least 50%, 60%, 70%, 80%, 85%, 90%, 95% or 98% identical to the sequence of a third polypeptide chain of the respective F2 to F17 polypeptide disclosed herein. Optionally any or all of the variable regions or CDRs of the first and second chains are substituted with different variable regions, optionally where variable regions are excluded from the sequences that are considered for computing identity.

Uses of Compounds

In one aspect, provided are the use of any of the compounds defined herein for the manufacture of a pharmaceutical preparation for the treatment or diagnosis of a mammal being in need thereof. Provided also are the use any of the compounds defined above as a medicament or an active component or active substance in a medicament. In a further aspect provided is a method for preparing a pharmaceutical composition containing a compound as defined above, to provide a solid or a liquid formulation for administration orally, topically, or by injection. Such a method or process at least comprises the step of mixing the compound with a pharmaceutically acceptable carrier.

In one aspect, provided is a method to treat, prevent or more generally affect a predefined condition by exerting a certain effect, or detect a certain condition using a compound herein, or a (pharmaceutical) composition comprising a compound disclosed herein.

The polypeptides described herein can be used to prevent or treat disorders that can be treated with antibodies, such as cancers, solid and non-solid tumors, hematological malignancies, infections such as viral infections, and inflammatory or autoimmune disorders.

In one embodiment, the an antigen of interest expressed on the surface of a malignant cell of a type cancer selected from the group consisting of: carcinoma, including that of the bladder, head and neck, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; and lymphoma/leukaemia (T-Lbly/T-ALL).

In one embodiment, polypeptides described herein can be used to prevent or treat a cancer selected from the group consisting of: carcinoma, including that of the bladder, head and neck, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma. Other exemplary disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; and lymphoma/leukaemia (T-Lbly/T-ALL).

In one aspect, the methods of treatment comprise administering to an individual a multispecific polypeptide in a therapeutically effective amount. A therapeutically effective amount may be any amount that has a therapeutic effect in a patient having a disease or disorder (or promotes, enhances, and/or induces such an effect in at least a substantial proportion of patients with the disease or disorder and substantially similar characteristics as the patient).

The multispecific polypeptides can be included in kits. The kits may optionally further contain any number of polypeptides and/or other compounds, e.g., 1, 2, 3, 4, or any other number of multispecific polypeptide and/or other compounds. It will be appreciated that this description of the contents of the kits is not limiting in any way. For example, the kit may contain other types of therapeutic compounds.

Optionally, the kits also include instructions for using the polypeptides, e.g., detailing the herein-described methods.

Also provided are pharmaceutical compositions comprising the compounds as defined above. A compound may be administered in purified form together with a pharmaceutical carrier as a pharmaceutical composition. The form depends on the intended mode of administration and therapeutic or diagnostic application. The pharmaceutical carrier can be any compatible, nontoxic substance suitable to deliver the compounds to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids A pharmaceutically acceptable carrier may further contain physiologically acceptable compounds that act for example to stabilize or to increase the absorption of the compounds Such physiologically acceptable compounds include, for example, carbohydrates, such as glucose, sucrose or dextrans, antioxidants, such as ascorbic acid or glutathione, chelating agents, low molecular weight proteins or other stabilizers or excipients One skilled in the art would know that the choice of a pharmaceutically acceptable carrier, including a physiologically acceptable compound, depends, for example, on the route of administration of the composition Pharmaceutically acceptable adjuvants, buffering agents, dispersing agents, and the like, may also be incorporated into the pharmaceutical compositions.

The compounds can be administered parenterally. Preparations of the compounds for parenteral administration must be sterile. Sterilization is readily accomplished by filtration through sterile filtration membranes, optionally prior to or following lyophilization and reconstitution. The parenteral route for administration of compounds is in accord with known methods, e.g. injection or infusion by intravenous, intraperitoneal, intramuscular, intraarterial, or intralesional routes. The compounds may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound, depending on the particular type of compound and its required dosing regimen. Methods for preparing parenterally administrable compositions are well known in the art.

EXAMPLES

Example 1

Generation of Anti-huNKp46 Antibodies

Balb/c mice were immunized with a recombinant human NKp46 extracellular domain recombinant-Fc protein. Mice received one primo-immunization with an emulsion of 50 µg NKp46 protein and Complete Freund Adjuvant, intraperitoneally, a 2nd immunization with an emulsion of 50 µg NKp46 protein and Incomplete Freund Adjuvant, intraperitoneally, and finally a boost with 10 µg NKp46 protein, intravenously. Immune spleen cells were fused 3 days after the boost with X63.Ag8.653 immortalized B cells, and cultured in the presence of irradiated spleen cells.

Primary screen: Supernatant (SN) of growing clones were tested in a primary screen by flow cytometry using a cell line expressing the human NKp46 construct at the cell surface. Briefly, for FACS screening, the presence of reacting antibodies in supernanants was revealed by Goat anti-mouse polyclonal antibody (pAb) labeled with PE.

A selection of antibodies that bound NKp46 were selected, produced and their variable regions further evaluated for their activity in the context of a bispecific molecule.

Example 2

Identification of a Bispecific Antibody Format that Binds FcRn but not FcγR for Targeting Effector Cell Receptors The aim of this experiment was to develop a new bispecific protein useful in targeting receptors on immune effector cells and a second antigen of interest, in which a monomeric Fc domain is placed on a polypeptide between two antigen binding domains. The proteins and binds to the two antigens monovalently, which retains at least partial binding to the human neonatal Fc receptor (FcRn) but does not substantially bind human CD16 and/or other human Fcγ receptors.

A first step was to produce a single chain protein with a monomeric Fc domain as a single chain protein to investigate whether a monomeric Fc domain would bind to the human neonatal Fc receptor (FcRn) and human Fcγ receptors.

Example 2-1 Construction and Binding Analysis of Anti-CD19-IgG1-Fcmono-Anti-CD3

Figure 2:
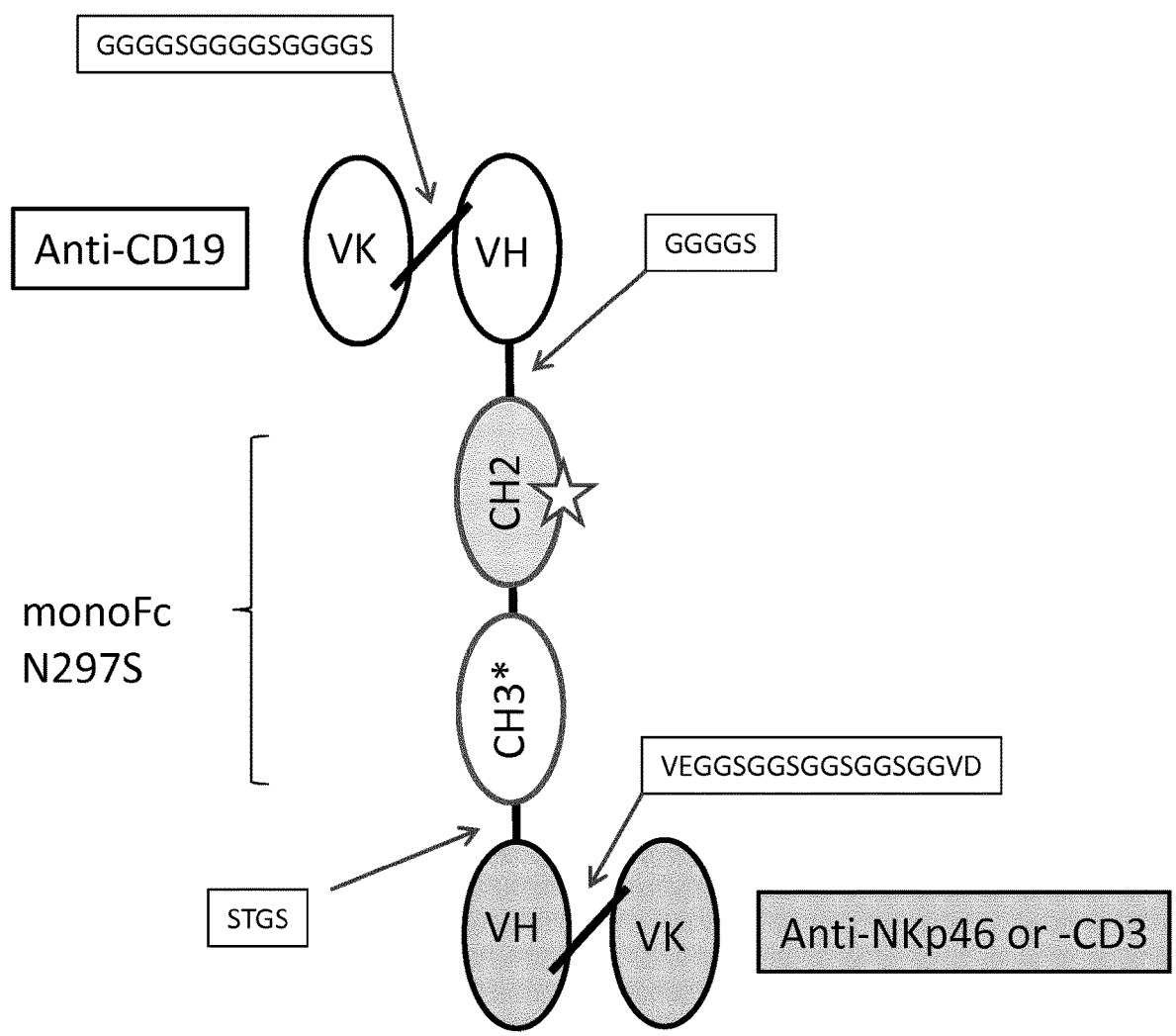
FIG. 2 shows a schematic of an anti-CD19-F1-Anti-NKp46 used in the Examples herein. The star in the CH2 domain indicates an option N297S mutation.
Figure 3:
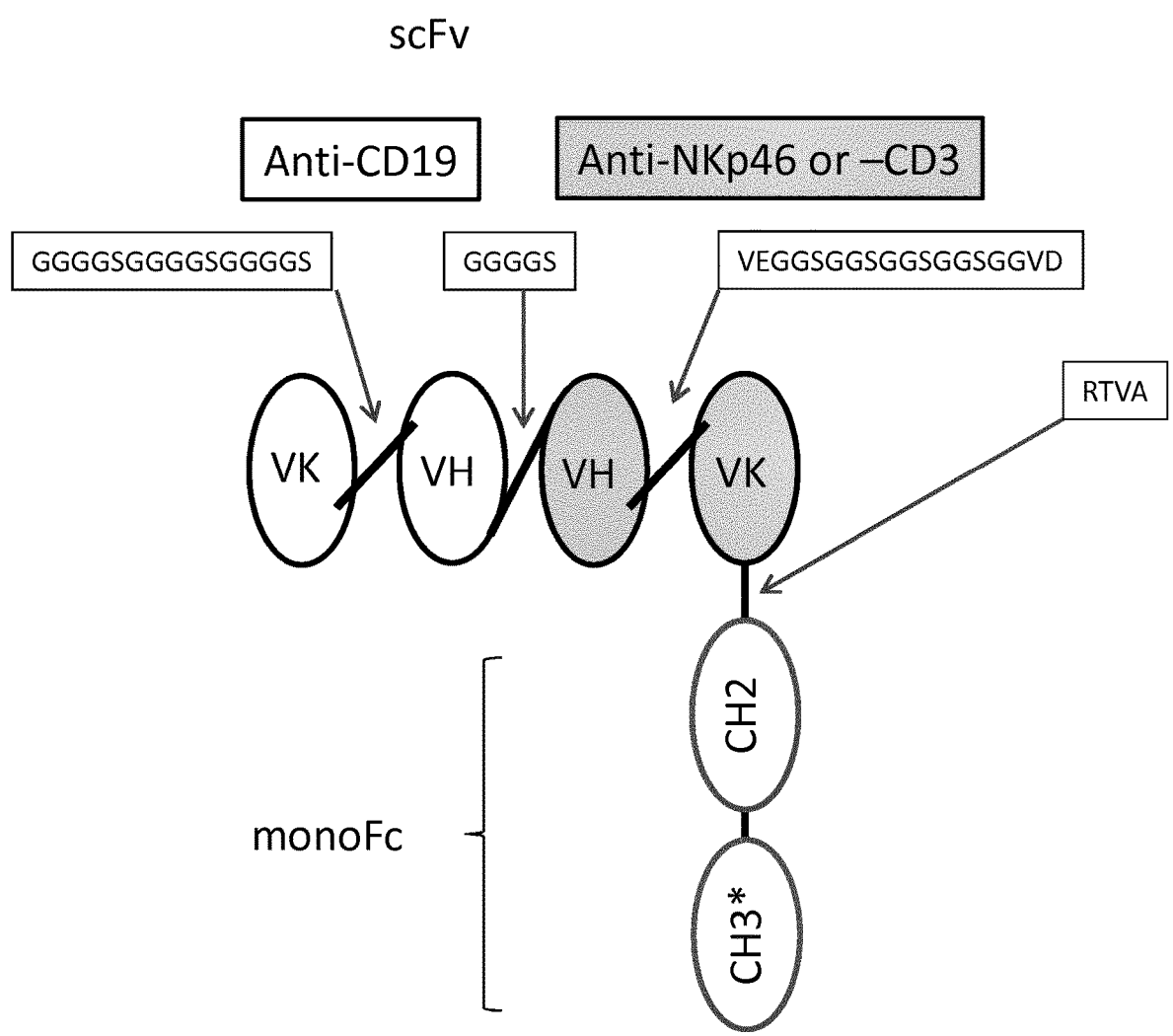
FIG. 3 shows a schematic of an anti-CD19-Anti-NKp46-IgG1-Fcmono. For the scFv tandem construct, the Anti-NKp46 VK domain (C-terminal) is linked to the CH2 domain (N-terminal) using a linker peptide (RTVA) that mimics the regular VK-CK elbow junction.

A bispecific Fc-based on a scFv specific for tumor antigen CD19 (anti-CD19 scFv) and a scFV specific for activating receptor CD3 on a T cell (anti-CD3 scFv) was used to assess FcRn binding and CD19-binding functions of a new monomeric bispecific polypeptide format. The domain arrangement of the final polypeptide is shown in FIG. 2 and is also referred to as the "F1" format in FIG. 6A (the star in the CH2 domain indicates an optional N297S mutation, not included in the polypeptide tested here).

A bispecific monomeric Fc-containing polypeptide was constructed based on an scFv specific for the tumor antigen CD19 (anti-CD19 scFv) and an scFV specific for an activating receptor CD3 on a T cell (anti-CD3 scFv). The CH3 domain incorporated the mutations (EU numbering) L351K, T366S, P395V, F405R, T407A and K409Y. The polypeptide has domains arranged as follows: anti-CD19-CH2-CH3-anti-CD3. DNA sequence coding for a CH3/VH linker peptide having the amino acid sequence STGS was designed in order to insert a specific SalI restriction site at the CH3-VH junction.

The CH3 domain incorporated the mutations (EU numbering) L351K, T366S, P395V, F405R, T407A and K409Y. The CH2 domain was a wild-type CH2. DNA and amino acid sequences for the monomeric CH2-CH3 Fc portion and the anti-CD19 are shown below.

The light chain and heavy chain DNA and amino acid sequences for the anti-CD19 scFv were as follows:

Anti-CD19-VK
(SEQ ID NO: 3)
GACATTCAGCTGACCCAATCTCCAGCTTCTTTGGCTGTGTCTCTAGGGC

AGAGGGCCACCATCTCCTGCAAGGCCAGCCAAAGTGTTGATTATGATGG

TGATAGTTATTTGAACTGGTACCAACAGATACCAGGACAGCCACCCAAA

CTCCTCATCTATGATGCATCCAATCTAGTATCTGGGATTCCACCCAGGT

TTAGTGGCAGTGGGTCTGGGACAGACTTCACCCTCAACATCCATCCTGT

GGAGAAGGTGGATGCTGCAACCTATCACTGTCAGCAAAGTACTGAGGAC

CCTTGGACGTTCGGTGGAGGCACCAAGCTGGAAATCAAA

Anti-CD19-VK
(SEQ ID NO: 4)
DIQLTQSPASLAVSLGQRATISCKASQSVDYDGDSYLNWYQQIPGQPPK
LLIYDASNLVSGIPPRFSGSGSGTDFTLNIHPVEKVDAATYHCQQSTED
PWTFGGGTKLEIK Anti-CD19-VH
(SEQ ID NO: 5)
CAGGTTCAGCTGCAGCAGTCTGGGGCTGAGCTGGTGCGGCCTGGGTCCT

CAGTGAAGATTTCCTGCAAAGCATCTGGCTACGCATTCAGTAGCTACTG

GATGAACTGGGTGAAGCAGAGGCCTGGACAGGGTCTTGAGTGGATTGGA

CAGATTTGGCCTGGAGATGGTGATACTAACTACAACGGAAAGTTCAAGG

GCAAGGCCACACTGACTGCAGACGAATCCTCCAGCACAGCCTACATGCA

GCTCAGCAGCCTGGCCTCTGAGGACTCTGCGGTCTATTTCTGTGCAAGA

CGAGAAACGACCACTGTCGGGCGTTATTACTATGCTATGGACTACTGGG

GTCAAGGAACCACAGTCACCGTCTCCTCA

Anti-CD19-VH
(SEQ ID NO: 6)
QVQLQQSGAELVRPGSSVKISCKASGYAFSSYWMNWVKQRPGQGLEWIG
QIWPGDGDTNYNGKFKGKATLTADESSSTAYMQLSSLASEDSAVYFCAR
RETTTVGRYYYAMDYWGQGTTVTVSS The DNA and amino acid sequences for the monomeric CH2-CH3 Fc portion and final bispecific polypeptide were as follows:

IgG1-Fcmono (the last K was removed in that construct)

(SEQ ID NO: 7)
GCACCTGAACTCCTGGGGGGACCGTCAGTCTTCCTCTTCCCCCCAAAAC

CCAAGGACACCCTCATGATCTCCCGGACCCCTGAGGTCACATGCGTGGT

GGTGGACGTGAGCCACGAAGACCCTGAGGTCAAGTTCAACTGGTACGTG

GACGGCGTGGAGGTGCATAATGCCAAGACAAAGCCGCGGGAGGAGCAGT

ACAACAGCACGTACCGTGTGGTCAGCGTCCTCACCGTCCTGCACCAGGA

CTGGCTGAATGGCAAGGAGTACAAGTGCAAGGTCTCCAACAAAGCCCTC

CCAGCCCCCATCGAGAAAACCATCTCCAAAGCCAAAGGGCAGCCCCGAG

AACCACAGGTGTACACCAAGCCCCCATCCCGGGAGGAGATGACCAAGAA

CCAGGTCAGCCTGTCCTGCCTGGTCAAAGGCTTCTATCCCAGCGACATC

GCCGTGGAGTGGGAGAGCAATGGGCAGCCGGAGAACAACTACAAGACCA

CGGTTCCCGTGCTGGACTCCGACGGCTCCTTCGCCTCGCTAGCTACCT

CACCGTGGACAAGAGCAGGTGGCAGCAGGGGAACGTCTTCTCATGCTCC

GTGATGCATGAGGCTCTGCACAACCACTACACGCAGAAGAGCCTCTCCC

TGTCCCCGGGG

IgG1-Fcmono* (*the last K residue was removed in that construct)
(SEQ ID NO: 8)
APELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKAL

PAPIEKTISKAKGQPREPQVYTKPPSREEMTKNQVSLSCLVKGFYPSDI

-continued

AVEWESNGQPENNYKTTVPVLDSDGSFRLASYLTVDKSRWQQGNVFSCS

VMHEALHNHYTQKSLSLSPG

Anti-CD19-F1-Anti-CD3 Complete sequence
(mature protein)
(SEQ ID NO: 9)
DIQLTQSPASLAVSLGQRATISCKASQSVDYDGDSYLNWYQQIPGQPPK

LLIYDASNLVSGIPPRFSGSGSGTDFTLNIHPVEKVDAATYHCQQSTED

PWTFGGGTKLEIKGGGSGGGGSGGGGSQVQLQQSGAELVRPGSSVKIS

CKASGYAFSSYWMNWVKQRPGQGLEWIGQIWPGDGDTNYNGKFKGKATL

TADESSSTAYMQLSSLASEDSAVYFCARRETTTVGRYYYAMDYWGQGTT

VTVSSGGGSSAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTKPPSREEMTKNQVSLSC

LVKGFYPSDIAVEWESNGQPENNYKTTVPVLDSDGSFRLASYLTVDKSR

WQQGNVFSCSVMHEALHNHYTQKSLSLSPGSTGSDIKLQQSGAELARPG

ASVKMSCKTSGYTFTRYTMHWVKQRPGQGLEWIGYINPSRGYTNYNQKF

KDKATLTTDKSSSTAYMQLSSLTSEDSAVYYCARYYDDHYCLDYWGQGT

TLTVSSVEGGSGGSGGSGGSGGVDDIQLTQSPAIMSASPGEKVTMTCRA

SSSVSYMNWYQQKSGTSPKRWIYDTSKVASGVPYRFSGSGSGTSYSLTI

SSMEAEDAATYYCQQWSSNPLTFGAGTKLELK

Cloning and Production of the Recombinant Proteins

Coding sequences were generated by direct synthesis and/or by PCR. PCR were performed using the PrimeSTAR MAX DNA polymerase (Takara, #R045A) and PCR products were purified from 1% agarose gel using the Nucleo-Spin gel and PCR clean-up kit (Macherey-Nagel, #740609.250). Once purified the PCR product were quantified prior to the In-Fusion ligation reaction performed as described in the manufacturer's protocol (ClonTech, #ST0345). The plasmids were obtained after a miniprep preparation run on an EVO200 (Tecan) using the Nucleospin 96 plasmid kit (Macherey-Nagel, #740625.4). Plasmids were then sequenced for sequences confirmation before to transfecting the CHO cell line.

CHO cells were grown in the CD-CHO medium (Invitrogen) complemented with phenol red and 6 mM GlutaMax. The day before the transfection, cells are counted and seeded at 175.000 cells/ml. For the transfection, cells (200.000 cells/transfection) are prepared as described in the AMAXA SF cell line kit (AMAXA, #V4XC-2032) and nucleofected using the DS137 protocol with the Nucleofector 4D device. All the tranfections were performed using 300 ng of verified plasmids. After transfection, cells are seeded into 24 well plates in pre-warmed culture medium. After 24H, hygromycine B was added in the culture medium (200 µg/ml). Protein expression is monitored after one week in culture. Cells expressing the proteins are then sub-cloned to obtain the best producers. Sub-cloning was performed using 96 flat-bottom well plates in which the cells are seeded at one cell per well into 200 µl of culture medium complemented with 200 µg/ml of hygromycine B. Cells were left for three weeks before to test the clone's productivity.

Recombinant proteins which contain a IgG1-Fc fragment are purified using Protein-A beads (—rProteinA Sepharose fast flow, GE Healthcare, ref.: 17-1279-03). Briefly, cell culture supernatants were concentrated, clarified by centrifugation and injected onto Protein-A columns to capture the recombinant Fc containing proteins. Proteins were eluted at acidic pH (citric acid 0.1M pH3), immediately neutralized using TRIS-HCL pH8.5 and dialyzed against 1×PBS. Recombinant scFv which contain a "six his" tag were purified by affinity chromatography using Cobalt resin. Other recombinant scFv were purified by size exclusion chromatography (SEC).

Example 2-2: Binding Analysis of Anti-CD19-IgG1-Fcmono-Anti-CD3 to B221, JURKAT, HUT78 and CHO Cell Lines Cells were harvested and stained with the cell supernatant of the anti-CD19-F1-anti-CD3 producing cells during 1 H at 4° C. After two washes in staining buffer (PBS1×/BSA 0.2%/EDTA 2 mM), cells were stained for 30 min at 4° C. with goat anti-human (Fc)-PE antibody (IM0550 Beckman Coulter—1/200). After two washes, stainings were acquired on a BD FACS Canto II and analyzed using the FlowJo software.

CD3 and CD19 expression were also controlled by flow cytometry: Cells were harvested and stained in PBS1×/BSA 0.2%/EDTA 2 mM buffer during 30 min at 4° C. using 5 µl of the anti-CD3-APC and 5 µl of the anti-CD19-FITC antibodies. After two washes, stainings were acquired on a BD FACS Canto II and analyzed using the FlowJo software.

The Anti-CD19-F1-Anti-CD3 protein binds to the CD3 cell lines (HUT78 and JURKAT cell lines) and the CD19 cell line (B221 cell line) but not to the CHO cell line used as a negative control.

Example 2-3

T- and B-Cell Aggregation by Purified Anti-CD19-F1-Anti-CD3

Purified Anti-CD19-F1-Anti-CD3 was tested in a T/B cell aggregation assay to evaluate whether the antibody is functional in bringing together CD19 and CD3 expressing cells.

Figure 4:
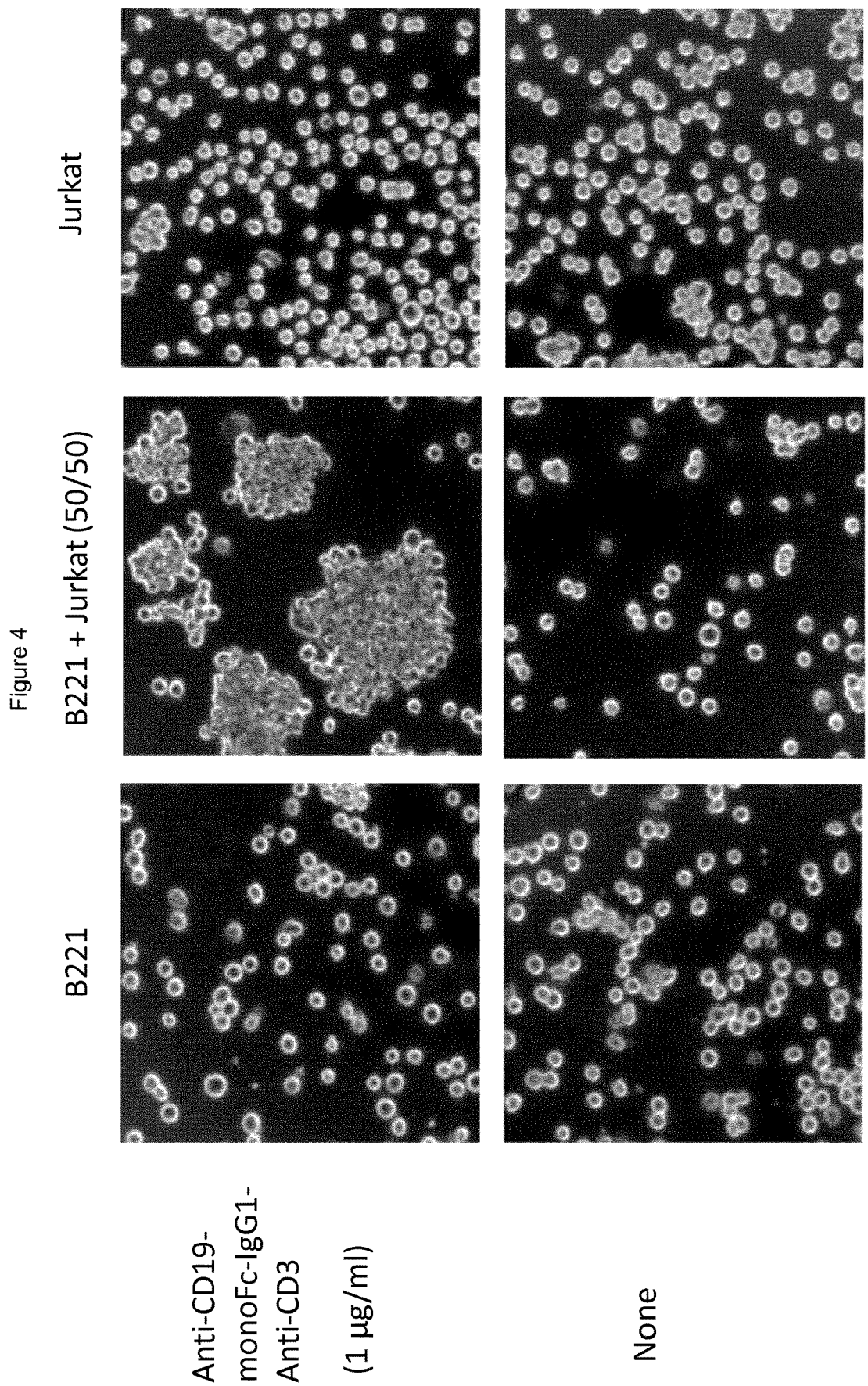
FIG. 4 shows that Anti-CD19-F1-Anti-CD3 does not cause T/B cell aggregation in the presence of B221 (CD19) or JURKAT (CD3) cell lines when separate, but it does cause aggregation of cells when both B221 and JURKAT cells are co-incubated.

Results are shown in FIG. 4. The top panel shows that Anti-CD19-F1-Anti-CD3 does not cause aggregation in the presence of B221 (CD19) or JURKAT (CD3) cell lines, but it does cause aggregation of cells when both B221 and JURKAT cells are co-incubated, illustrating that the bispecific antibody is functional. The lower panel shows control without antibody.

Example 2-4

Binding of Bispecific Monomeric Fc Polypeptide to FcRn Affinity Study by Surface Plasmon Resonance (SPR)

Biacore T100 General Procedure and Reagents

SPR measurements were performed on a Biacore T100 apparatus (Biacore GE Healthcare) at 25° C. In all Biacore experiments Acetate Buffer (50 mM Acetate pH5.6, 150 mM NaCl, 0.1% surfactant p20) and HBS-EP+ (Biacore GE Healthcare) served as running buffer and regeneration buffer respectively. Sensorgrams were analyzed with Biacore T100 Evaluation software. Recombinant mouse FcRn was purchase from R&D Systems.

Immobilization of FcRn

Recombinant FcRn proteins were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore GE Healthcare)). FcRn proteins were diluted to 10 µg/ml in coupling buffer (10 mM acetate, pH 5.6) and injected until the appropriate immobilization level was reached (i.e. 2500 RU). Deactivation of the remaining activated groups was performed using 100 mM ethanolamine pH 8 (Biacore GE Healthcare).

Affinity Study

Monovalent affinity study was done following the Single Cycle Kinetic (SCK) protocol. Five serial dilutions of soluble analytes (antibodies and bi-specific molecules) ranging from 41.5 to 660 nM were injected over the FcRn (without regeneration) and allowed to dissociate for 10 min before regeneration. For each analyte, the entire sensorgram was fitted using the 1:1 SCK binding model.

Results

Figure 5:
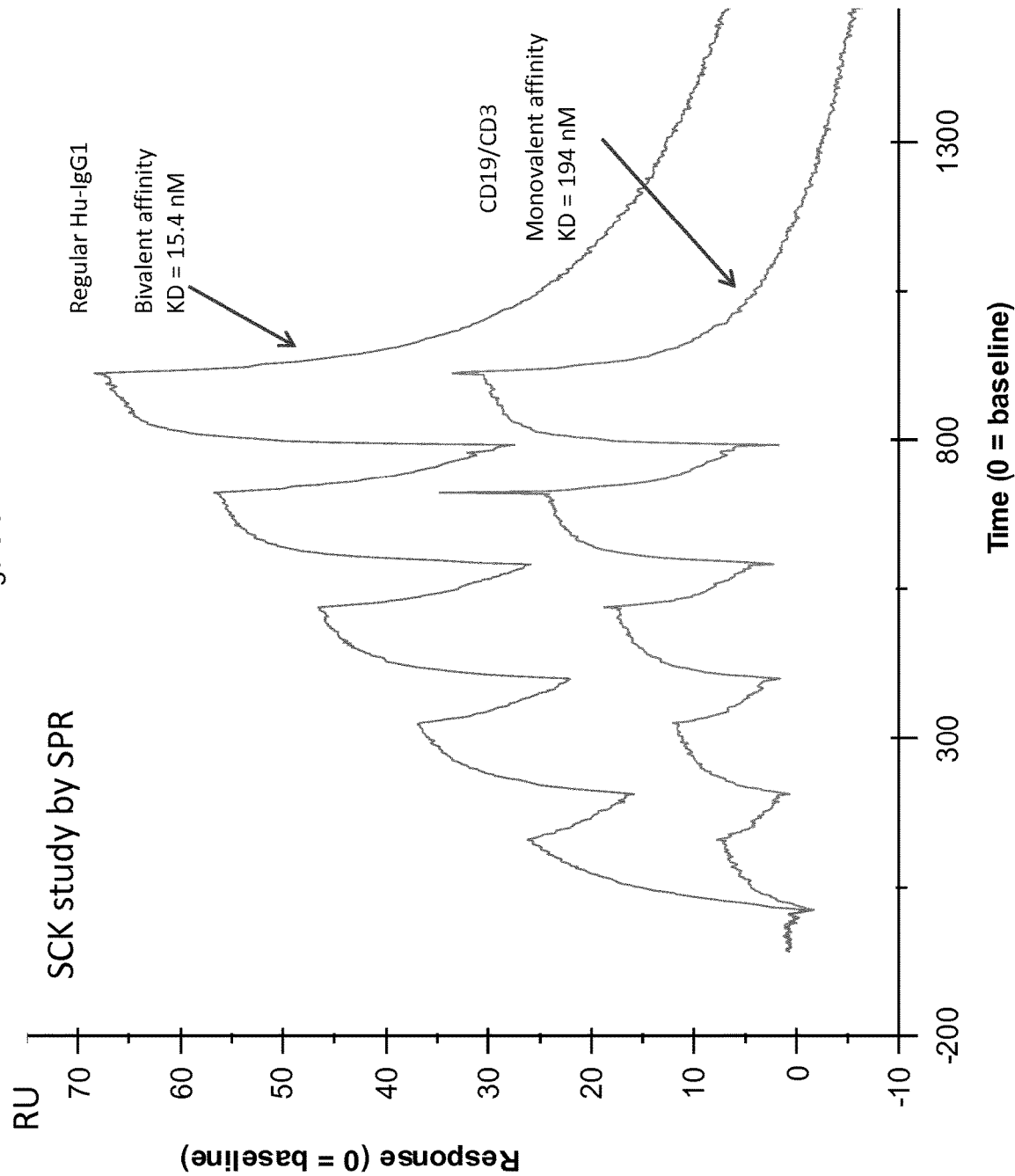
FIG. 5 shows Anti-CD19-F1-Anti-CD3 retains binding to FcRn, with a 1:1 ratio (1 FcRn for each monomeric Fc) (KD=194 nM), in comparison to a chimeric full length antibody having human IgG1 constant regions (KD=15.4 nM) which binds to FcRn with a 2:1 ration (2 FcRn for each antibody).

Anti-CD19-F1-Anti-CD3 having its CH2-CH3 domains placed between two antigen binding domains, here two scFv, was evaluated to assess whether such bispecific monomeric Fc protein could retain binding to FcRn and thereby have improved in vivo half-lives compared to convention bispecific antibodies. Results showed that FcRn binding was retained, the model suggesting 1:1 ratio (1 FcRn for each monomeric Fc) instead of 2:1 ration (2 FcRn for each antibody) for a regular IgG. Results are shown in FIG. 5.

Affinity was evaluated using SPR, in comparison to a chimeric full length antibody having human IgG1 constant regions. Results are shown in FIG. 5. The monomeric Fc retained significant monomeric binding to FcRn (monomeric Fc: affinity of KD=194 nM; full length antibody with bivalent binding: avidity of KD=15.4 nM).

Example 3

Construction of Multimeric Bispecific Monomeric Polypeptides

The aim of this experiment was to develop a new bispecific protein format that has advantages in production over currently available bispecific antibodies in development, e.g. DART and BITE antibodies.

The initial bispecific protein was designed to place an Fc domain on a polypeptide together with a binding domain that bind to a receptor present on the surface of immune effector cells, chosen to be anti-NKp46 which binds the activating receptor NKp46 on NK cells, and an anti-target antigen binding domain, chosen to be anti-CD19 which binds the lymphoma tumor antigen. The bispecific protein binds to NKp46 monovalently while the monomeric Fc domain retains at least partial binding to the human neonatal Fc receptor (FcRn), yet does not substantially bind human CD16 and/or other human Fcγ receptors. Consequently, the bispecific protein will not induce Fcγ-mediated (e.g. CD16-mediated) target cell lysis.

It was unknown what activating receptors on NK cells would contribute to lysis of target cells, and as anti-NKp46 antibodies may block NKp46, whether cytotoxicity could be mediated by NKp46 triggering. We investigated whether the bispecific protein format could induce NKp46 triggering, and moreover without inducing NKp46 agonism in the absence of target cells, which could lead to inappropriate NK activation distant from the target and/or decreased overall activity toward target cells.

Multimeric proteins that comprise two or three polypeptide chains, wherein the Fc domain remains monomeric, were developed that are compatible for use with antibody variable regions that do not maintain binding to their target when converted to scFv format. The formats can be used conveniently for antibody screening; by incorporating at least one binding region as a F(ab) structure, any anti-target (e.g. anti-tumor) antibody variable region can be directly expressed in a bispecific construct as the F(ab) format within the bispecific protein and tested, irrespective of whether the antibody would retain binding as an scFv, thereby simplifying screening and enhancing the number of antibodies available. These formats in which the Fc domain remains monomeric have the advantage of maintaining maximum conformational flexibility which may permit optimal binding to both target antigens, e.g., effector cell receptor and/or target antigens.

Different constructs were made for use in the preparation of bispecific antibodies using the variable domains DNA and amino acid sequences from the scFv specific for tumor antigen CD19 described in Example 2-1, and different variable regions from antibodies specific for the NKp46 receptor identified in Example 1.

For the Fc domain to remain monomeric in single chain polypeptides or multimers in which only one chain had an Fc domain, CH3-CH3 dimerization was prevented through two different strategies: (1) through the use of CH3 domain incorporating the mutations (EU numbering) L351K, T366S, P395V, F405R, T407A and K409Y; or (2) through the use of a tandem CH3 domain in which the tandem CH3 domains separated by a flexible linker associated with one another, in turn preventing interchain CH3-CH3 dimerization. The DNA and amino acid sequences for the monomeric CH2-CH3 Fc portion with point mutations were as in Example 2-1. The DNA and amino acid sequences for the monomeric CH2-CH3-linker-CH3 Fc portion with tandem CH3 domains is shown in FIGS. 6A-6D.

The light chain and heavy chain DNA and amino acid sequences for the anti-CD19 scFv were as in Example 2-1. Proteins were cloned, produced and purified as in Example 2-1. Shown below are an exemplary light chain and heavy chain DNA and amino acid sequences for an anti-NKp46 scFv NKp46-3.

| scFv anti-NKp46 | scFv sequence (VHVK)/-stop |
|---|---|
| NKp46-3 | STGSEVQLQQSGPELVKPGASVKISCKTSGYTFTEYTMH WVKQSHGKSLEWIGGISPNIGGTSYNQKFKGKATLTVDK SSSTAYMELRSLTSEDSAVYYCARRGGSFDYWGQTTLT VSSVEGGSGGSGGSGGSGGVDDIVMTQSPATLSVTPGDR VSLSCRASQSISDYLHWYQQKSHESPRLLIKYASQSISG IPSRFSGSGSGSDFTLSINSVEPEDVGVYYCQNGHSFPL TFGAGTKLELK- (SEQ ID NO: 10) |

Format 1 (F1) (Anti-CD19-IgG1-Fcmono-Anti-NKp46 (scFv))

Figure 6A:
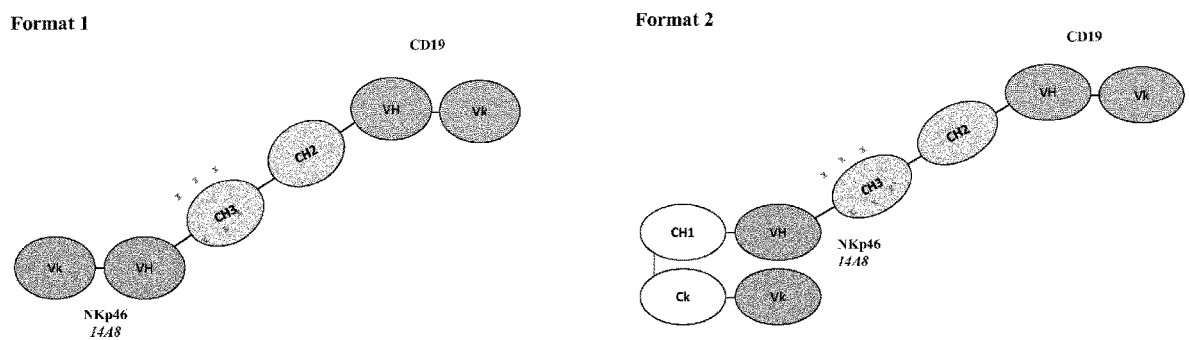

The domain structure of Format 1 (F1) is shown in FIG. 6A. A bispecific Fc-containing polypeptide was constructed based on an scFv specific for the tumor antigen CD19 (anti-CD19 scFv) and an scFV specific for the NKp46 receptor. The polypeptide is a single chain polypeptide having domains arranged (N- to C-terminal) as follows: (VK-VH)$^{anti-CD19}$-CH2-CH3 (VH-VK)$^{anti-NKp46}$ A DNA sequence coding for a CH3/VH linker peptide having the amino acid sequence STGS was designed in order to insert a specific SalI restriction site at the CH3-VH junction. The domain arrangement of the final polypeptide in shown in FIG. 2 (star in the CH2 domain indicates an optional N297S mutation). The (VK-VH) units include a linker between the VH and VK domains. Proteins were cloned, produced and purified as in Example 2-1.

Format 2 (F2): CD19-F2-NKp46-3

The domain structure of F2 polypeptides is shown in FIG. 6A. The DNA and amino acid sequences for the monomeric CH2-CH3 Fc portion were as in Example 2-1 containing CH3 domain mutations (the mutations (EU numbering) L351K, T366S, P395V, F405R, T407A and K409Y. The heterodimer is made up of:

(1) a first (central) polypeptide chain having domains arranged as follows (N- to C-terminal):
$(VK-VH)^{anti-CD19}$-CH2-CH3-$VH^{anti-NKp46}$-CH1
and (2) a second polypeptide chain having domains arranged as follows (N- to C-terminal): $VK^{anti-NKp46}$-CK.

The (VK-VH) unit was made up of a VH domain, a linker and a VK unit (i.e. an scFv). As with other formats of the bispecific polypeptides, the DNA sequence coded for a CH3/VH linker peptide having the amino acid sequence STGS designed in order to insert a specific SalI restriction site at the CH3-VH junction. Proteins were cloned, produced and purified as in Example 2-1. The amino acid sequences for the CD19-F2-NKp46-3 Polypeptide chain 1 is shown in SEQ ID NO: 11 and CD19-F2-NKp46-3 Polypeptide chain 2 in SEQ ID NO: 12.

Format 8 (F8)

The domain structure of F8 polypeptides is shown in FIG. 6B. The DNA and amino acid sequences for the monomeric CH2-CH3 Fc portion were as in Format F2 containing CH3 domain mutations (the mutations (EU numbering) L351K, T366S, P395V, F405R, T407A and K409Y, as well as a N297S mutation to prevent N-linked glycosylation and abolish FcγR binding. Three variants of F8 proteins were produced: (a) cysteine residues in the hinge region left intact (wild-type, referred to as F8A), (b) cysteine residues in the hinge region replaced by serine residues (F8B), and (c) a linker sequence GGGSS replacing residues DKTHTCPPCP in the hinge (F8C). Variants F8B and F8C provided advantages in production by avoiding formation of homodimers of the central chain. The heterotrimer is made up of;

(1) a first (central) polypeptide chain having domains arranged as follows (N- to C-terminal):
$VH^{anti-CD19}$-CH1-CH2-CH3-$VH^{anti-NKp46}$-CK
and (2) a second polypeptide chain having domains arranged as follows (N- to C-terminal): $VK^{anti-NKp46}$-CH1
and (3) a third polypeptide chain having domains arranged as follows (N- to C-terminal):
$VK^{anti-CD19}$-CK Proteins were cloned, produced and purified as in Example 2-1. Bispecific proteins was purified from cell culture supernatant by affinity chromatography using prot-A beads and analysed and purified by SEC. The protein showed a high production yield of 3.7 mg/L (F8C) and with a simple SEC profile. The amino acid sequences for the three F8 protein chains for the F8 "C" variant are shown in SEQ ID NOS 13, 14 and 15.

Format 9 (F9): CD19-F9-NKp46-3

The F9 polypeptide is a trimeric polypeptide having a central polypeptide chain and two polypeptide chains each of which associate with the central chain via CH1-CK dimerization. The domain structure of the trimeric F9 protein is shown in FIG. 6B, wherein the bonds between the CH1 and CK domains are interchain disulfide bonds. The two antigen binding domains have a F(ab) structure permitting the use of antibodies irrespective of whether they remain functional in scFv format. The DNA and amino acid sequences for the CH2-CH3 Fc portion comprised a tandem CH3 domain in which the two CH3 domains on the same polypeptide chain associated with one another, thereby preventing dimerization between different bispecific proteins. The CH2 domain included a N297S substitution. Three variants of F9 proteins were produced: (a) cysteine residues in the hinge region left intact (wild-type, referred to as F9A), (b) cysteine residues in the hinge region replaced by serine residues (F9B), and (c) a linker sequence GGGSS replacing residues DKTHTCPPCP in the hinge (F9C). Variants F9B and F9C provided advantages in production by avoiding formation of homodimers of the central chain. The heterotrimer is made up of:

(1) a first (central) polypeptide chain having domains arranged as follows (N- to C-terminal):
$VH^{anti-CD19}$-CH1-CH2-CH3-CH3-$VH^{anti-NKp46}$-CK and (2) a second polypeptide chain having domains arranged as follows (N- to C-terminal): $VK^{anti-NKp46}$-CH1
and (3) a third polypeptide chain having domains arranged as follows (N- to C-terminal):
$vK^{anti-CD19}$-CK Proteins were cloned, produced and purified as in Example 2-1. Bispecific proteins was purified from cell culture supernatant by affinity chromatography using prot-A beads and analysed and purified by SEC. The protein showed a high production yield of 8.7 mg/L (F9A) and 3.0 mg/L (F9B), and with a simple SEC profile. The amino acid sequences for the three F9 protein chains for each of variants F9A, F9B and F9C are shown in the SEQ ID NOS listed in the table below.

| Protein | SEQ ID NOS |
|---------|------------|
| F9A | 16, 17, 18 |
| F9B | 19, 20, 21 |
| F9C | 22, 23, 24 |

Format 10 (F10): CD19-F10-NKp46-3

The F10 polypeptide is a dimeric protein having a central polypeptide chain and a second polypeptide chain which associates with the central chain via CH1-CK dimerization. The domain structure of the dimeric F10 proteins is shown in FIG. 6B wherein the bonds between the CH1 and CK domains are interchain disulfide bonds. One of the two antigen binding domains has a Fab structure, and the other is a scFv. The DNA and amino acid sequences for the CH2-CH3 Fc portion comprised a tandem CH3 domain as in Format F9 and a CH2 domain with a N297S substitution. Additionally, three variants of F10 proteins were produced: (a) cysteine residues in the hinge region left intact (wild-type, referred to as F10A), (b) cysteine residues in the hinge region replaced by serine residues (F10B, and (c) a linker sequence GGGSS replacing residues DKTHTCPPCP in the hinge (F10O). Variants F10B an F10O provided advantages in production by avoiding formation of homodimers of the central chain. The (VK-VH) unit was made up of a VH domain, a linker and a VK unit (scFv). The heterodimer is made up of:

(1) a first (central) polypeptide chain having domains arranged as follows (N- to C-terminal):
$VH^{anti-CD19}$-CH1-CH2-CH3-CH3-$(VH-VK)^{anti-NKp}$46
and (2) a second polypeptide chain having domains arranged as follows (N- to C-terminal): $VK^{anti-CD19}$-CK.

Proteins were cloned, produced and purified as in Example 2-1. Bispecific proteins was purified from cell culture supernatant by affinity chromatography using prot-A beads and analysed and purified by SEC. The protein showed a good production yield of 2 mg/L (F10A) and with a simple SEC profile. The amino acid sequences for the three F9 protein chains for each of variants F10A, F10B and F10C are shown in the SEQ ID NOS listed in the table below.

| Protein | SEQ ID NOS |
|---------|------------|
| F10A    | 25, 26     |
| F10B    | 27, 28     |
| F10C    | 29, 30     |

Format 11 (F11): CD19-F11-NKp46-3

The domain structure of F11 polypeptides is shown in FIG. 6C. The heterodimeric protein is similar to F10 but the structures of the antigen binding domains are reversed. One of the two antigen binding domains has a Fab-like structure, and the other is a scFv. The heterodimer is made up of (1) a first (central) polypeptide chain having domains arranged as follows (N- to C-terminal):

(VK-VH)$^{anti-CD19}$ CH2-CH3-CH3-VH$^{anti-NKp46}$-CK and (2) a second polypeptide chain having domains arranged as follows (N- to C-terminal): VK$^{anti-NKp46}$-CH1.

Proteins were cloned, produced and purified as in Example 2-1. Bispecific proteins was purified from cell culture supernatant by affinity chromatography using prot-A beads and analysed and purified by SEC. The protein showed a good production yield of 2 mg/L and with a simple SEC profile. The amino acid sequences for the two chains of the F11 protein are shown in SEQ ID NOS 31 and 32.

Format 12 (F12): CD19-F12-NKp46-3

The domain structure of the dimeric F12 polypeptides is shown in FIG. 6C, wherein the bonds between the CH1 and CK domains are disulfide bonds. The heterodimeric protein is similar to F11 but the CH1 and CK domains within the F(ab) structure are inversed. The heterodimer is made up of:

(1) a first (central) polypeptide chain having domains arranged as follows (N- to C-terminal):

(VK md VH)$^{anti-CD19}$-CH2-CH3-CH3-VH$^{anti-NKp46}$-CH1 and (2) a second polypeptide chain having domains arranged as follows (N- to C-terminal): VK$^{anti-NKp46}$-CK.

Proteins were cloned, produced and purified as in Example 2-1. Bispecific proteins was purified from cell culture supernatant by affinity chromatography using prot-A beads and analysed and purified by SEC. The protein showed a good production yield of 2.8 mg/L and with a simple SEC profile. The amino acid sequences for the two chains of the F12 protein are shown in SEQ ID NOS: 33 and 34.

Format 17 (F17): CD19-F17-NKp46-3

The domain structure of the trimeric F17 polypeptides is shown in FIG. 6C, wherein the bonds between the CH1 and CK domains are disulfide bonds. The heterodimeric protein is similar to F9 but the VH and VK domains, and the CH1 and CK, domains within the C-terminal F(ab) structure are each respectively inversed with their partner. The heterotrimer is made up of:

(1) a first (central) polypeptide chain having domains arranged as follows (N- to C-terminal):

VH$^{anti-CD19}$-CH1-CH2-CH3-CH3-VK$^{anti-NKp46}$-CH1 and (2) a second polypeptide chain having domains arranged as follows (N- to C-terminal): VH$^{anti-NKp46}$-CK and (3) a third polypeptide chain having domains arranged as follows (N- to C-terminal): VK$^{anti-CD19}$-CK Additionally, three variants of F17 proteins were produced: (a) cysteine residues in the hinge region left intact (wild-type, referred to as F17A), (b) cysteine residues in the hinge region replaced by serine residues (F10B, and (c) a linker sequence GGGSS replacing residues DKTHTCPPCP in the hinge (F17C). Proteins were cloned, produced and purified as in Example 2-1. The amino acid sequences for the three chains of the F17B protein chains are shown in SEQ ID NOS: 35, 36 and 37.

Example 4

Bispecific NKp46 Antibody Formats with Dimeric Fc Domains

New protein constructions with dimeric Fc domains were developed that share advantages of the monomeric Fc domain proteins of Example 3 but bind to FcRn with greater affinity, but which also have low or substantially lack of binding to FcγR. The polypeptide formats were tested to investigate the functionality of heterodimeric proteins comprising a VH-(CH1 or CK)-CH2-CH3- comprising chain and a VK-(CH1 or CK)-CH2-CH3- comprising chain. One of both of the CH3 domains will then be fused, optionally via intervening amino acid sequences or domains, to a variable domain(s) (a single variable domain that associates with a variable domain on a separated polypeptide chain, a tandem variable domain (e.g., an scFv), or a single variable domain that is capable of binding antigen as a single variable domain. The two chains then associate by CH1-CK dimerization to form disulfide linked dimers, or if associated with a third chain, to form trimers.

Different constructs were made for use in the preparation of a bispecific antibody using the variable domains DNA and amino acid sequences derived from the scFv specific for tumor antigen CD19 described in Example 2-1 and different variable regions from antibodies specific for NKp46 identified in Example 1. Proteins were cloned, produced and purified as in Example 2-1. Domains structures are shown in FIGS. 6A-6D.

Format 5 (F5): CD19-F5-NKp46-3

The domain structure of the trimeric F5 polypeptide is shown in FIG. 6D, wherein the interchain bonds between hinge domains and interchain bonds between the CH1 and CK domains are interchain disulfide bonds. The heterotrimer is made up of:

(1) a first (central) polypeptide chain having domains arranged as follows (N- to C-terminal):

VH$^{anti-CD19}$-CH1-CH2-CH3-VH$^{anti-NKp46}$-CK and (2) a second polypeptide chain having domains arranged as follows (N- to C-terminal): VK$^{anti-CD19}$-CK-CH2-CH3 and (3) a third polypeptide chain having domains arranged as follows (N- to C-terminal):

VK$^{anti-NKp46}$-CH1

Proteins were cloned, produced and purified as in Example 2-1. Bispecific proteins was purified from cell culture supernatant by affinity chromatography using prot-A beads and analysed and purified by SEC. The protein showed a high production yield of 37 mg/L and with a simple SEC profile. The amino acid sequences of the three chains are shown in SEQ ID NOS: 38, 39 and 40.

Format 6 (F6): CD19-F6-NKp46-3

The domain structure of heterotrimeric F6 polypeptides is shown in FIG. 6D. The F6 protein is the same as F5, but with a N297S substitution to avoid N-linked glycosylation. Proteins were cloned, produced and purified as in Example 2-1. Bispecific proteins was purified from cell culture supernatant by affinity chromatography using prot-A beads and analysed and purified by SEC. The protein showed a high production yield of 12 mg/L and with a simple SEC profile. The amino acid sequences of the three chains of the F6 protein are shown in SEQ ID NOS: 41, 42 and 43.

Format 7 (F7): CD19-F7-NKp46-3

The domain structure of heterotrimeric F7 polypeptides is shown in FIG. 6D. The F7 protein is the same as F6, but with cysteine to serine substitutions in the CH1 and CK domains that are linked at their C-termini to the Fc domains, to prevent formation of a minor population of dimeric species of the central chain with the $VK^{anti-NKp46}$-CH1 chain. Proteins were cloned, produced and purified as in Example 2-1. Bispecific proteins was purified from cell culture supernatant by affinity chromatography using prot-A beads and analysed and purified by SEC. The protein showed a high production yield of 11 mg/L and with a simple SEC profile. The amino acid sequences of the three chains of the 76 protein are shown in SEQ ID NOS: 44, 45 and 46.

Format 13 (F13): CD19-F13-NKp46-3

The domain structure of the dimeric F13 polypeptide is shown in FIG. 6D, wherein the interchain bonds between hinge domains (indicated between CH1/CK and CH2 domains on a chain) and interchain bonds between the CH1 and CK domains are interchain disulfide bonds. The heterodimer is made up of:

(1) a first (central) polypeptide chain having domains arranged as follows (N- to C-terminal):
$VH^{anti-CD19}$-CH1-CH2-CH3-(VH-VK)$^{anti-NKp46}$
and (2) a second polypeptide chain having domains arranged as follows (N- to C-terminal): $VK^{anti-CD19}$-CK-CH2-CH3.

The (VH-VK) unit was made up of a VH domain, a linker and a VK unit (scFv).

Proteins were cloned, produced and purified as in Example 2-1. Bispecific proteins was purified from cell culture supernatant by affinity chromatography using prot-A beads and analysed and purified by SEC. The protein showed a high production yield of 6.4 mg/L and with a simple SEC profile. The amino acid sequences of the two chains of the F13 protein are shown in SEQ ID NOS: 47 and 48.

Format 14 (F14): CD19-F14-NKp46-3

The domain structure of the dimeric F14 polypeptide is shown in FIG. 6E. The F14 polypeptide is a dimeric polypeptide which shares the structure of the F13 format, but instead of a wild-type Fc domain (CH2-CH3), the F14 has CH2 domain mutations N297S to abolish N-linked glycosylation. Proteins were cloned, produced and purified as in Example 2-1. Bispecific proteins was purified from cell culture supernatant by affinity chromatography using prot-A beads and analysed and purified by SEC. The protein showed a high production yield of 2.4 mg/L and with a simple SEC profile. The amino acid sequences of the two chains of the F14 protein are shown in SEQ ID NOS: 49 and 50.

Format 15 (F15): CD19-F15-NKp46-3

The domain structure of the trimeric F15 polypeptides is shown in FIG. 6E. The F15 polypeptide is a dimeric polypeptide which shares the structure of the F6 format, but differs by inversion of the N-terminal VH-CH1 and VK-CK units between the central and second chains. Proteins were cloned, produced and purified as in Example 2-1. Bispecific proteins was purified from cell culture supernatant by affinity chromatography using prot-A beads and analysed and purified by SEC. The protein showed a good production yield of 0.9 mg/L and with a simple SEC profile. The amino acid sequences of the three chains of the F15 protein are shown in SEQ ID NOS: 51, 52 and 53.

Format 16 (F16): CD19-F16-NKp46-3

The domain structure of the trimeric F16 polypeptide is shown in FIG. 6E. The F16 polypeptide is a dimeric polypeptide which shares the structure of the F6 format, but differs by inversion of the C-terminal VH-CK and VK-CH1 units between the central and second chains. Proteins were cloned, produced and purified as in Example 2-1. The amino acid sequences of the three chains of the F16 protein are shown in SEQ ID NOS: 54, 55 and 56.

Example 5

NKp46 Binding Affinity by Bispecific Proteins by Surface Plasmon Resonance (SPR)

Biacore T100 General Procedure and Reagents

SPR measurements were performed on a Biacore T100 apparatus (Biacore GE Healthcare) at 25° C. In all Biacore experiments HBS-EP+(Biacore GE Healthcare) and NaOH 10 mM served as running buffer and regeneration buffer respectively. Sensorgrams were analyzed with Biacore T100 Evaluation software. Protein-A was purchase from (GE Healthcare). Human NKp46 recombinant proteins were cloned, produced and purified at Innate Pharma.

Immobilization of Protein-A

Protein-A proteins were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore GE Healthcare)). Protein-A was diluted to 10 µg/ml in coupling buffer (10 mM acetate, pH 5.6) and injected until the appropriate immobilization level was reached (i.e. 2000 RU). Deactivation of the remaining activated groups was performed using 100 mM ethanolamine pH 8 (Biacore GE Healthcare).

Binding Study

Antibodies were tested as different formats F5, F6, F9, F10, F11, F13, F14 and compared to the single chain format (F1), and an anti-NKp46 antibody as a full-length human IgG1.

Bispecific proteins at 1 µg/mL were captured onto Protein-A chip and recombinant human NKp46 proteins were injected at 5 µg/mL over captured bispecific antibodies. For blank subtraction, cycles were performed again replacing NKp46 proteins with running buffer.

Affinity Study

Monovalent affinity study was done following a regular Capture-Kinetic protocol recommended by the manufacturer (Biacore GE Healthcare kinetic wizard). Seven serial dilutions of human NKp46 recombinant proteins, ranging from 6.25 to 400 nM were sequentially injected over the captured Bi-Specific antibodies and allowed to dissociate for 10 min before regeneration. The entire sensorgram sets were fitted using the 1:1 kinetic binding model.

Results

SPR showed that the bispecific polypeptides of formats F1, F5, F6, F9, F10, F11, F13, F14 retained binding to NKp46.

Monovalent affinities and kinetic association and dissociation rate constants are shown below in the table 3 below.

TABLE 3

| Bispecific mAb | ka (1/Ms) | kd (1/s) | KD (M) |
| --- | --- | --- | --- |
| CD19-F1-NKp46-3 | 7.05E+04 | 6.44E−04 | 9.14E−09 |
| CD19-F5-NKp46-3 | 7.555E+4 | 0.00510 | 67E−09 |
| CD19-F6-NKp46-3 | 7.934E+4 | 0.00503 | 63E−09 |
| CD19-F9A-NKp46-3 | 2.070E+5 | 0.00669 | 32E−09 |
| CD19-F10A-NKp46-3 | 2.607E+5 | 0.00754 | 29E−09 |
| CD19-F11A-NKp46-3 | 3.388E+5 | 0.01044 | 30E−09 |
| CD19-F13-NKp46-3 | 8.300E+4 | 0.00565 | 68E−09 |
| CD19-F14-NKp46-3 | 8.826E+4 | 0.00546 | 62E−09 |
| NKp46-3 IgG1 | 2.224E+5 | 0.00433 | 20E−09 |

Example 6

Engagement of NK Cells Against Daudi Tumor Target with Fc-Containing NKp46×CD19 Bispecific Protein Bispecific antibodies having a monomeric Fc domain and a domain arrangement according to the single chain F1 or dimeric F2 formats described in Example 3, and a NKp46 binding region based on different anti-NKp46 variable domains (NKp46-1, NKp46-2, NKp46-3 or NKp46-4) were tested for functional ability to direct NK cells to lyse CD19-positive tumor target cells (Daudi, a well characterized B lymphoblast cell line). The F2 proteins additionally included NKp46-9 variable regions which lost binding to NKp46 in the scFv format but which retained binding in the F(ab)-like format of F2.

Briefly, the cytolytic activity of each of (a) resting human NK cells, and (b) human NK cell line KHYG-1 transfected with human NKp46, was assessed in a classical 4-h $^{51}$Cr-release assay in U-bottom 96 well plates. Daudi cells were labelled with $^{51}$Cr (50 μCi (1.85 MBq)/1×10$^6$ cells), then mixed with KHYG-1 transfected with hNKp46 at an effector/target ratio equal to 50 for KHYG-1, and 10 (for F1 proteins) or 8.8 (for F2 proteins) for resting NK cells, in the presence of monomeric bi-specific antibodies at different concentrations. After brief centrifugation and 4 hours of incubation at 37° C., samples of supernatant were removed and transferred into a LumaPlate (Perkin Elmer Life Sciences, Boston, Mass.), and $^{51}$Cr release was measured with a TopCount NXT beta detector (PerkinElmer Life Sciences, Boston, Mass.). All experimental conditions were analyzed in triplicate, and the percentage of specific lysis was determined as follows: 100×(mean cpm experimental release−mean cpm spontaneous release)/(mean cpm total release−mean cpm spontaneous release). Percentage of total release is obtained by lysis of target cells with 2% Triton X100 (Sigma) and spontaneous release corresponds to target cells in medium (without effectors or Abs).

Results

In the KHYG-1 hNKp46 NK experimental model, each bi-specific antibody NKp46-1, NKp46-2, NKp46-3, NKp46-4 or NKp46-9 induced specific lysis of Daudi cells by human KHYG-1 hNKp46 NK cell line compared to negative controls (Human IgG1 isotype control (IC) and CD19/CD3 bi-specific antibodies), thereby showing that these antibodies induce Daudi target cell lysis by KHYG-1 hNKp46 through CD19/NKp46 cross-linking.

Figure 7A:
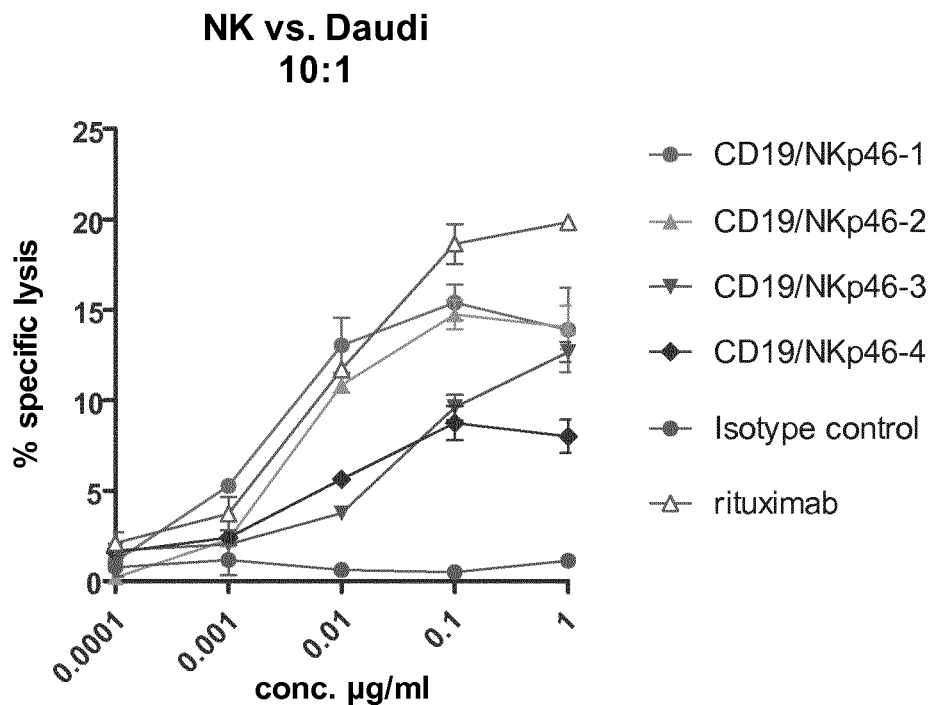
FIGS. 7A and 7B show respectively bispecific F1 and F2 antibodies having NKp46 binding region based on NKp46-1, NKp46-2, NKp46-3 or NKp46-4 are able to direct resting NK cells to their CD19-positive Daudi tumor target cells, while isotype control antibody did not lead to elimination of the Daudi cells. Rituximab (RTX) served as positive control of ADCC, where the maximal response obtained with RTX (at 10 μg/ml in this assay) was 21.6% specific lysis.
Figure 7B:
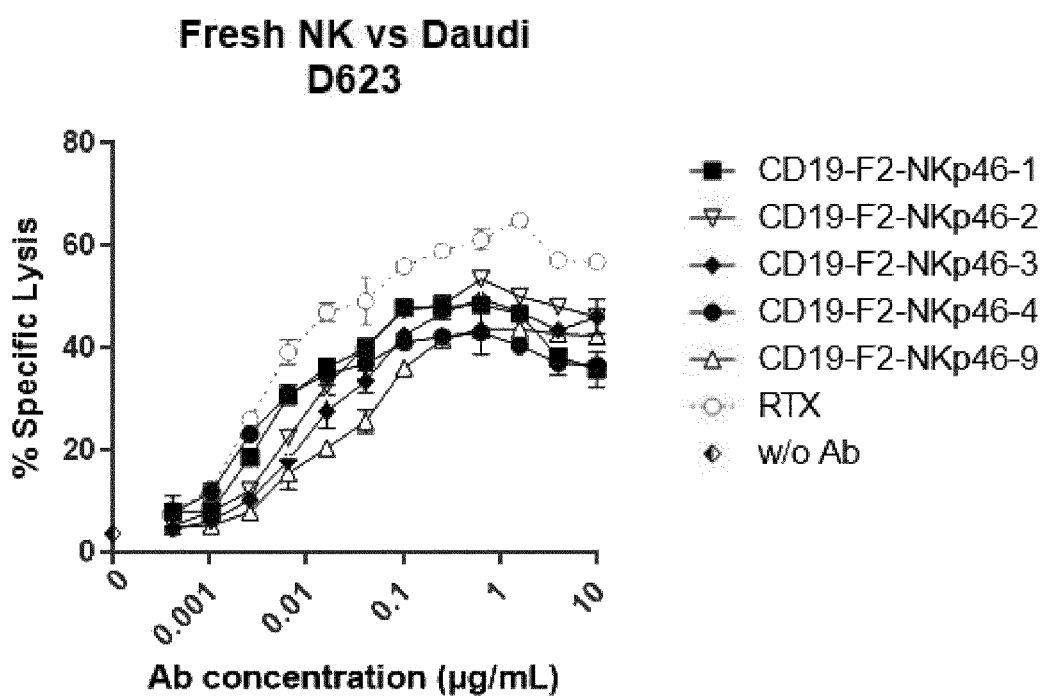

When resting NK cells were used as effectors, each bi-specific antibody NKp46-1, NKp46-2, NKp46-3, NKp46-4 or NKp46-9 again induced specific lysis of Daudi cells by human NK cells compared to negative control (Human IgG1 isotype control (IC) antibody), thereby showing that these antibodies induce Daudi target cell lysis by human NK cells through CD19/NKp46 cross-linking. Rituximab (RTX, chimeric IgG1) was used as a positive control of ADCC (Antibody-Dependent Cell Cytotoxicity) by resting human NK cells. The maximal response obtained with RTX (at 10 μg/ml in this assay) was 21.6% specific lysis illustrating that the bispecific antibodies have high target cell lysis activity. Results for experiments with resting NK cells are shown in FIG. 7A for the single chain F1 proteins and 7B for the dimeric F2 proteins.

Example 7

Comparison with Full Length Anti-NKp46 mAbs and Depleting Anti-Tumor mAbs: Only NKp46×CD19 Bispecific Proteins Prevent Non-Specific NK Activation These studies aimed to investigate whether bispecific antibodies can mediate NKp46-mediated NK activation toward cancer target cells without triggering non-specific NK cell activation.

NKp46×CD19 bispecific proteins having an arrangement according to the F2 format described in Example 3 with anti-NKp46 variable domains from NKp46-1, NKp46-2, NKp46-3, NKp46-4 or NKp46-9 were compared to:
 (a) full-length monospecific anti-NKp46 antibodies (NKp46-3 as human IgG1), and
 (b) the anti-CD19 antibody as a full-length human IgG1 as ADCC inducing antibody control comparator.

The experiments further included as controls: rituximab, an anti-CD20 ADCC inducing antibody control for a target antigen with high expression levels; anti-CD52 antibody alemtuzumab, a human IgG1, binds CD52 target present on both targets and NK cells; and negative control isotype control therapeutic antibody (a human IgG1 that does not bind a target present on the target cells (HUG1-IC).

The different proteins were tested for functional effect on NK cell activation in the presence of CD19-positive tumor target cells (Daudi cells), in the presence of CD19-negative, CD16-positive target cells (HUT78 T-lymphoma cells), and in the absence of target cells.

Briefly, NK activation was tested by assessing CD69 and CD107 expression on NK cells by flow cytometry. The assay was carried out in 96 U well plates in completed RPMI, 150 μL final/well. Effector cells were fresh NK cells purified from donors. Target cells were Daudi (CD19-positive), HUT78 (CD19-negative) or K562 (NK activation control cell line). In addition to K562 positive control, three conditions were tested, as follows:
 NK cell alone
 NK cells vs Daudi (CD19+)
 NK cells vs HUT78 (CD19−)
 Effector:Target (E:T) ratio was 2.5:1 (50 000 E: 20 000 T), with an antibody dilution range starting to 10 μg/mL with 1/4 dilution (n=8 concentrations). Antibodies, target cells and effector cells were mixed; spun 1 min at 300 g; incubated 4 h at 37° C.; spun 3 min at 500 g; washed twice with Staining Buffer (SB); added 50 μL of staining Ab mix; incubated 30 min at 300 g; washed twice with SB resuspended pellet with CellFix; stored overnight at 4° C.; and fluorescence revealed with Canto II (HTS).

Results

1. NK Cells Alone

Results are shown in FIG. 8A. In the absence of target-antigen expressing cells, none of the bispecific anti-NKp46× anti-CD19 antibody (including each of the NKp46-1, NKp46-2, NKp46-3, NKp46-4 and NKp46-9 variable regions) activated NK cells as assessed by CD69 or CD107 expression. Full-length anti-CD19 also did not activate NK cells. However, the full-length anti-NKp46 antibodies caused detectable activation of NK cells. Alemtuzumab also induced activation of NK cells, at a very high level. Isotype control antibody did not induce activation.

2. NK Cells Vs Daudi (CD19+)

Results are shown in FIG. 8B. In the presence of target-antigen expressing cells, each of the bispecific anti-NKp46× anti-CD19 antibodies (including each of the NKp46-1, NKp46-2, NKp46-3, NKp46-4 and NKp46-9 binding domains) activated NK cells. Full-length anti-CD19 showed at best only very low activation of NK cells. Neither full-length anti-NKp46 antibodies or alemtuzmab showed substantial increase in activation beyond what was observed in presence of NK cells alone. FIG. 8B shows full-length anti-NKp46 antibodies showed a similar level of baseline activation observed in presence of NK cells alone. Alemtuzumab also induced activation of NK cells a similar level of activation observed in presence of NK cells alone, and at higher antibody concentrations in this setting (ET 2.5:1) the activation was greater than with the bispecific anti-NKp46×anti-CD19 antibody. Isotype control antibody did not induce activation.

3. NK Cells Vs HUT78 (CD19−)

Results are shown in FIG. 8C. In the presence of target-antigen-negative HUT78 cells, none of the bispecific anti-NKp46×anti-CD19 antibody (including each of the NKp46-1, NKp46-2, NKp46-3, NKp46-4 and NKp46-9 variable regions) activated NK cells. However, the full-length anti-NKp46 antibodies and alemtuzumab caused detectable activation of NK cells at a similar level observed in presence of NK cells alone. Isotype control antibody did not induce activation.

In conclusion, the bispecific anti-NKp46 proteins are able to activate NK cells in a target-cell specific manner, unlike full-length monospecific anti-NKp46 antibodies and full-length antibodies of depleting IgG isotypes which also activate NK cells in the absence of target cells. The NK cell activation achieved with anti-NKp46 bispecific proteins was higher than that observed with full length anti-CD19 IgG1 antibodies.

Example 8

Comparative Efficacy with Depleting Anti-Tumor mAbs: NKp46×CD19 Bispecific Proteins at Low ET Ratio These studies aimed to investigate whether bispecific antibodies can mediate NKp46-mediated NK cell activation toward cancer target cells at lower effector:target ratios. The ET ratio used in this Example was 1:1 which is believed to be closer to the setting that would be encountered in vivo than the 2.5:1 ET ratio used in Example 7 or the 10:1 ET ratio of Example 6.

NKp46×CD19 bispecific proteins having an arrangement according to the F2 format described in Example 3 with anti-NKp46 variable domains from NKp46-1, NKp46-2, NKp46-3, NKp46-4 or NKp46-9 were compared to:
(a) full-length monospecific anti-NKp46 antibodies (NKp46-3 as human IgG1), and
(b) the anti-CD19 antibody as a full-length human IgG1 as ADCC inducing antibody control comparator.

The experiments further included as controls: rituximab (an anti-CD20 ADCC inducing antibody control for a target antigen with high expression levels); anti-CD52 antibody alemtuzumab (a human IgG1, binds CD52 target present on both targets and NK cells), and negative control isotype control therapeutic antibody (a human IgG1 that does not bind a target present on the target cells (HUG1-IC). The different proteins were tested for functional effect on NK cell activation as assessed by CD69 or CD107 expression in the presence of CD19-positive tumor target cells (Daudi cells), in the presence of CD19-negative, CD16-positive target cells (HUT78 T-lymphoma cells), and in the absence of target cells. The experiments were carried out as in Example 7 except that the ET ratio was 1:1.

Results

Results are shown in FIG. 9 (top panel: CD107 and bottom panel: CD69). In the presence of target-antigen expressing cells, each of the bispecific anti-NKp46×anti-CD19 antibody (including each of the NKp46-1, NKp46-2, NKp46-3, NKp46-4 and NKp46-9 variable regions) activated NK cells in the presence of Daudi cells.

The activation induced by bispecific anti-NKp46×anti-CD19 antibody in the presence of Daudi cells was far more potent than the full-length human IgG1 anti-CD19 antibody as ADCC inducing antibody which had low activity in this setting. Furthermore, in this low E:T ratio setting the activation induced by bispecific anti-NKp46×anti-CD19 antibody was as potent as anti-CD20 antibody rituximab, with a difference being observed only at the highest concentrations that were 10 fold higher than concentrations in which differences were observed at the 2.5:1 ET ratio.

In the absence of target cells or in the in the presence of target antigen-negative HUT78 cells, full-length anti-NKp46 antibodies and alemtuzumab showed a similar level of baseline activation observed in the presence of Daudi cells. anti-NKp46×anti-CD19 antibody did not activate NK cells in presence of HUT78 cells.

In conclusion, the bispecific proteins are able to activate NK cells in a target-cell specific manner and at lower effector:target ratio are more effective in mediating NK cell activation that traditional human IgG1 antibodies.

Example 9

Mechanism of Action Studies

NKp46×CD19 bispecific proteins having an arrangement according to the F2, F3 (a single chain format), F5 or F6 formats described in Examples 3 or 4 with anti-NKp46 variable domains from NKp46-3 were compared to rituximab (anti-CD20 ADCC inducing antibody), and a human IgG1 isotype control antibody for functional ability to direct CD16−/NKp46+NK cell lines to lyse CD19-positive tumor target cells.

Briefly, the cytolytic activity of the CD16−/NKp46+ human NK cell line KHYG-1 was assessed in a classical 4-h $^{51}$Cr-release assay in U-bottom 96 well plates. Daudi or B221 cells were labelled with $^{51}$Cr (50 μCi (1.85 MBq)/1× $10^6$ cells), then mixed with KHYG-1 at an effector/target ratio equal to 50:1, in the presence of test antibodies at dilution range starting from $10^{-7}$ mol/L with 1/5 dilution (n=8 concentrations)

After brief centrifugation and 4 hours of incubation at 37° C., 50 μL of supernatant were removed and transferred into a LumaPlate (Perkin Elmer Life Sciences, Boston, Mass.), and $^{51}$Cr release was measured with a TopCount NXT beta detector (Perkin Elmer Life Sciences, Boston, Mass.). All experimental conditions were analyzed in triplicate, and the percentage of specific lysis was determined as follows: 100×(mean cpm experimental release−mean cpm spontaneous release)/(mean cpm total release−mean cpm spontaneous release). Percentage of total release is obtained by lysis of target cells with 2% Triton X100 (Sigma) and spontaneous release corresponds to target cells in medium (without effectors or Abs).

Results

Figure 10A:
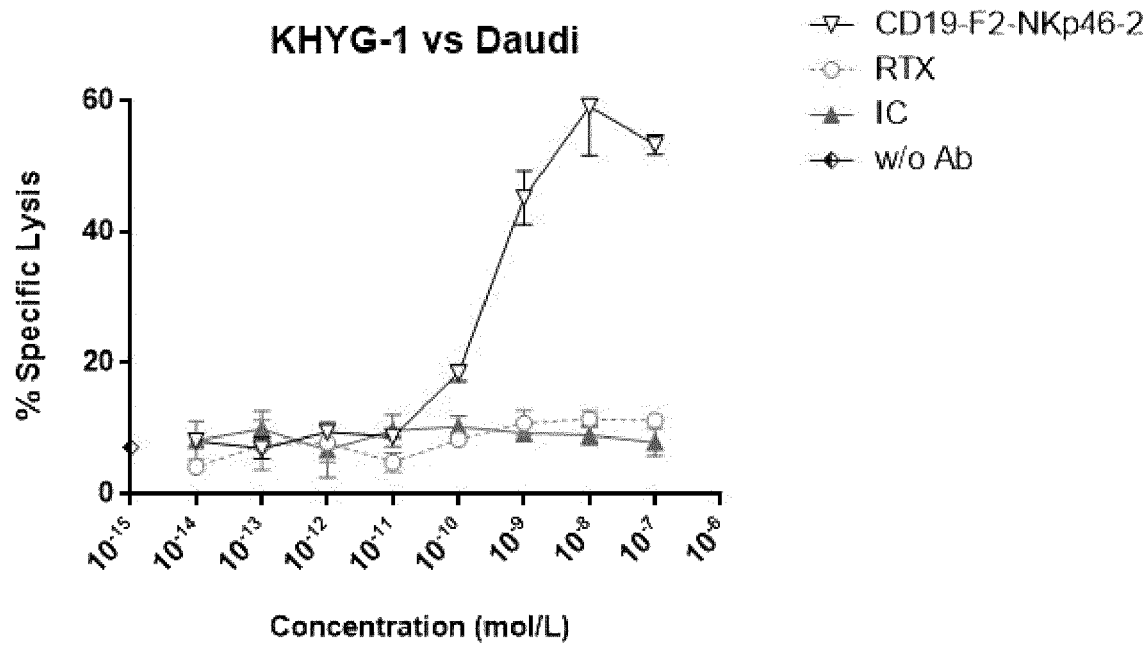
FIG. 10 shows that each NKp46×CD19 bispecific protein (single chain format F3, and multimeric formats F5 and F6) induced specific lysis of Daudi (FIG. 10A) or B221 (FIG. 10B) cells by human KHYG-1 CD16-negative hNKp46-positive NK cell line, while rituximab and human IgG1 isotype control (IC) antibodies did not.
Figure 10B:
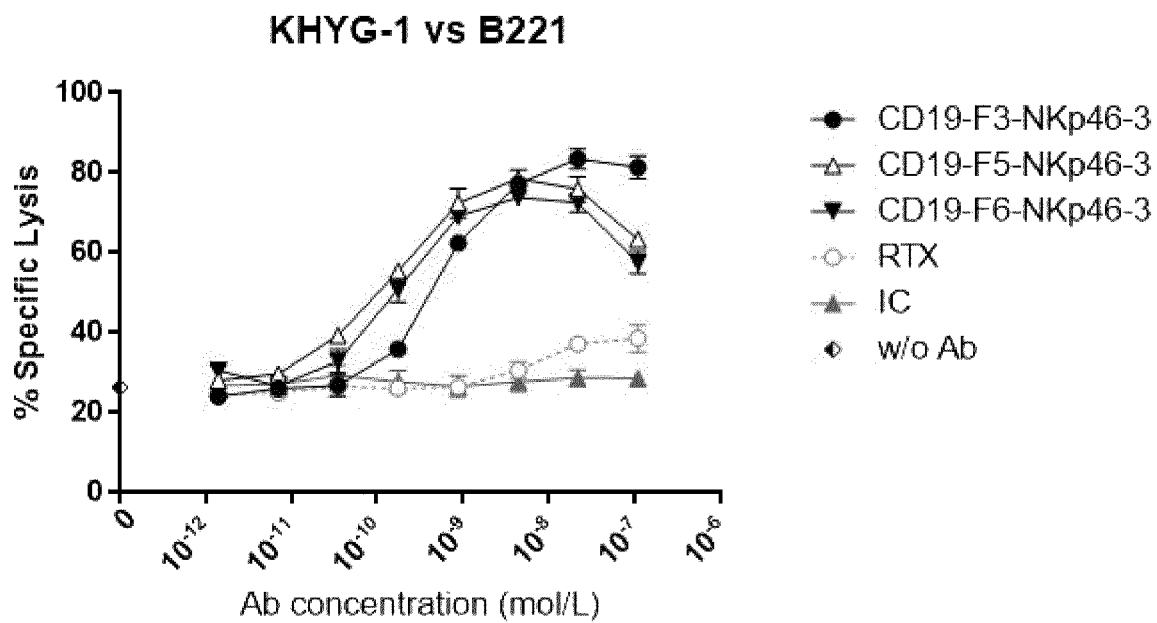

Results are shown in FIG. 10A (KHYG-1 vs Daudi) or 10B (KHYG-1 vs B221). In the KHYG-1 hNKp46 NK experimental model, each NKp46×CD19 bispecific protein (Format F2, F3, F5 and F6) induced specific lysis of Daudi or B221 cells by human KHYG-1 hNKp46 NK cell line, while rituximab and human IgG1 isotype control (IC) antibodies did not.

Example 10

Binding of Different Bispecific Formats to FcRn

Affinity of different antibody formats for human FcRn was studied by Surface Plasmon Resonance (SPR) by immobilizing recombinant FcRn proteins covalently to carboxyl groups in the dextran layer on a Sensor Chip CM5, as described in Example 2-5.

A chimeric full length anti-CD19 antibody having human IgG1 constant regions and NKp46×CD19 bispecific proteins having an arrangement according to the F5, F6, F9, F10, F11, F13 or F14 formats described in Examples 3 or 4 with anti-NKp46 variable domains from NKp46-3 (NKp46-2 for F2) were tested; for each analyte, the entire sensorgram was fitted using the steady state or 1:1 SCK binding model.

Results are shown in the table below. The bispecific proteins having dimeric Fc domains (formats F5, F6, F13, F14) bound to FcRn with affinity similar to that of the full-length IgG1 antibody. The bispecific proteins with monomeric Fc domains (F9, F10, F11) also displayed binding to FcRn, however with lower affinity that the bispecific proteins having dimeric Fc domains.

| Antibody/Bispecific | SPR method | KD nM |
| --- | --- | --- |
| Human IgG1/K Anti-CD19 | SCK/Two state reaction | 7.8 |
| CD19-F5-NKp46-3 | SCK/Two state reaction | 2.6 |
| CD19-F6-NKp46-3 | SCK/Two state reaction | 6.0 |
| CD19-F13-NKp46-3 | SCK/Two state reaction | 15.2 |
| CD19-F14-NKp46-3 | SCK/Two state reaction | 14.0 |
| CD19-F9A-NKp46-3 | Steady State | 858.5 |
| CD19-F10A-NKp46-3 | Steady State | 432.8 |
| CD19-F11-NKp46-3 | Steady State | 595.5 |

Example 11

Binding of Anti-CD19×Anti-NKp46 to FcγR

Anti-CD19-F1-Anti-NKp46 having its CH2-CH3 domains placed between two antigen binding domains, here two scFv, was evaluated to assess whether such bispecific monomeric Fc protein could retain binding to Fcγ receptors.

Figure 11:
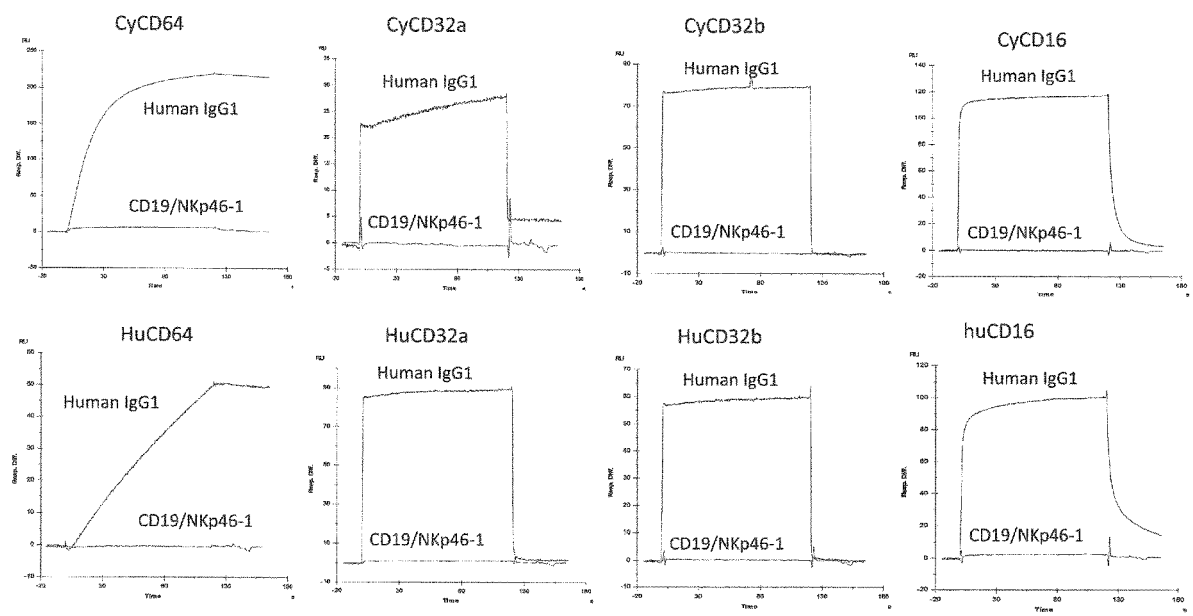
FIG. 11 shows superimposed sensorgrams showing the binding of *Macaca fascicularis* recombinant FcgRs (upper panels; CyCD64, CyCD32a, CYCD32b, CyCD16) and of human recombinant FcgRs (lower panels; HuCD64, HuCD32a, HuCD32b, HUCD16a) to the immobilized human IgG1 control (grey) and CD19/NKp46-1 bi-specific antibody with monomeric Fc domain (black). While full length wild type human IgG1 bound to all cynomolgus and human Fcγ receptors, the CD19/NKp46-1 monomeric-Fc bi-specific antibodies did not bind to any of the receptors.

Human IgG1 antibodies and CD19/NKp46-1 bi-specific antibodies were immobilized onto a CM5 chip. Recombinant FcγRs (cynomolgus monkey and human CD64, CD32a, CD32b, and CD16) were cloned, produced and purified at Innate Pharma. FIG. 11 shows superimposed sensorgrams showing the binding of *Macaca fascicularis* recombinant FcgRs (upper panels; CyCD64, CyCD32a, CYCD32b, CyCD16) and of Human recombinant FcgRs (lower panels; HuCD64, HuCD32a, HuCD32b, HuCD16a) to the immobilized human IgG1 control (grey) and CD19/NKp46-1 bi-specific antibody (black). Sensorgrams were aligned to zero in the y and x axis at the sample injection start.

FIG. 11 shows that while full length wild type human IgG1 bound to all cynomolgus and human Fcγ receptors, the CD19/NKp46-1 bi-specific antibodies did not bind to any of the receptors.

Example 12

Figure 12A:
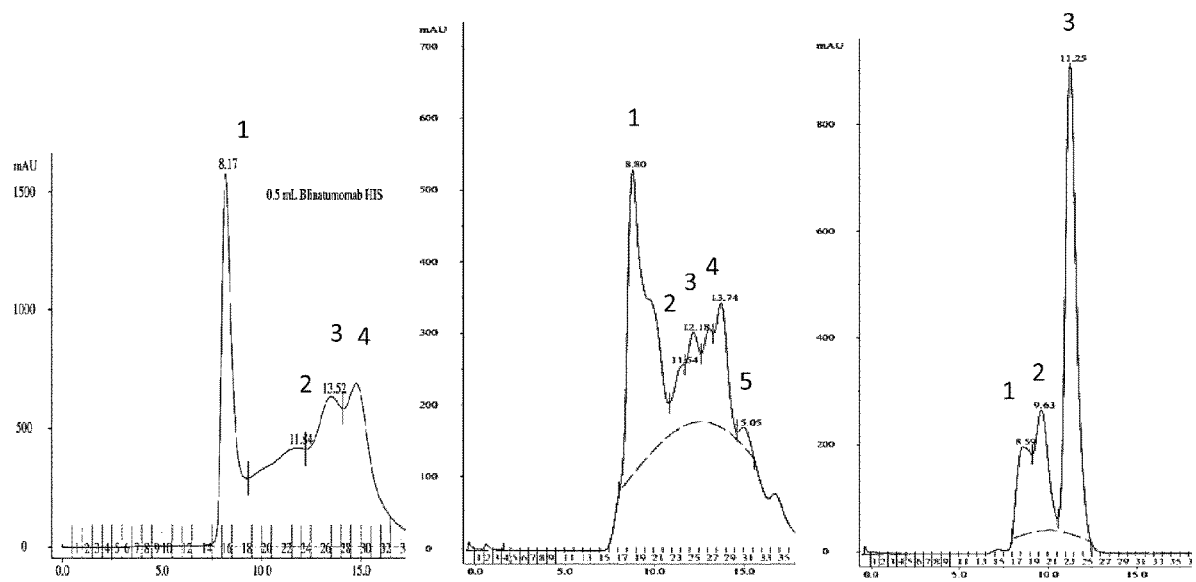
FIG. 12A shows results of purification by SEC of proteins format 6 (F6), compared with DART and BITE. BITE and DART showed a very low production yield compared to F6 and have a very complex SEC profile.
Figure 12B:
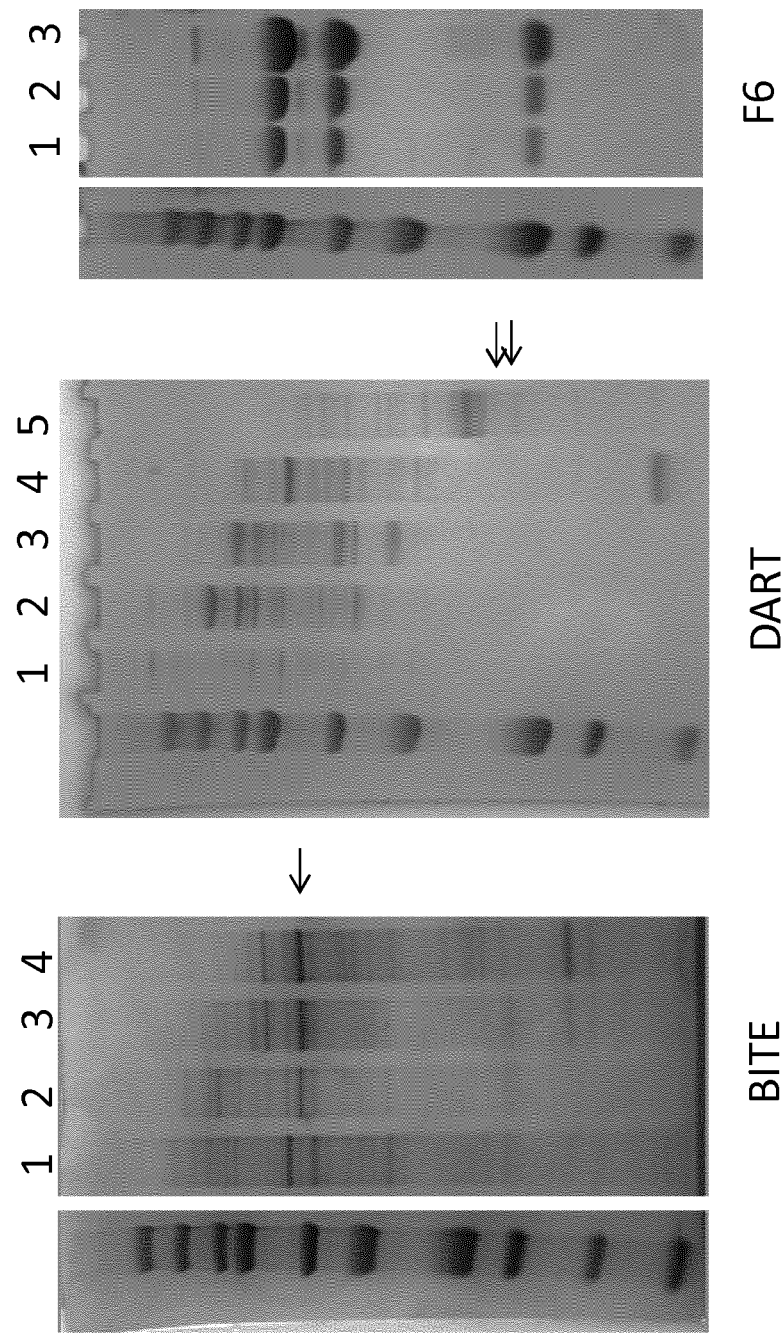
FIG. 12B shows SDS-PAGE after Coomassie staining in the expected SEC fractions (3 and 4 for BITE and 4 and 5 for DART), whereas F6 format showed clear and simple SEC and SDS-PAGE profiles with a major peak (fraction 3) containing the monomeric bispecific proteins.

Improved Product Profile and Yield of Different Bispecific Formats Compared to Existing Formats Blinatumomab and two bispecific antibodies having NKp46 and CD19 binding regions based on F1 to F17 formats and NKp46-3, and blinatumomab, respectively were cloned and produced under format 6 (F6), DART and BITE formats following the same protocol and using the same expression system. F6, DART and BITE bispecific proteins were purified from cell culture supernatant by affinity chromatography using prot-A beads for F6 or Ni-NTA beads for DART and BITE. Purified proteins were further analysed and purified by SEC (FIG. 12A). BITE and DART showed a very low production yield compared to F6 and have a very complex SEC profile. As shown in FIG. 12B (arrows), DART and BITE are barely detectable by SDS-PAGE after Coomassie staining in the expected SEC fractions (3 and 4 for BITE and 4 and 5 for DART), whereas F6 format showed clear and simple SEC and SDS-PAGE profiles with a major peak (fraction 3) containing the monomeric bispecific proteins. The major peak for the F6 format corresponded to about 30% of the total proteins. These observations are also true for F1 to F17 proteins (data not shown) indicating that the Fc domain (or Fc-derive domain) present in those formats facilitate the production and improve the quality and solubility of bispecific proteins.

Moreover, the Fc domains present in proteins F1 to F17 have the advantage of being adapted to affinity chromatography without the need for incorporation of peptide tags that will thereafter remain present as an unwanted part of a therapeutic product, such as in the case of BiTe and DART antibodies which cannot be purified by protein A. F1 to F17 antibodies are all bound by protein A. The table below shows productivity of different formats.

| Format | SEC | SDS PAGE Reduced | SDS PAGE Non Reduced | Final <<productivity>> yield |
|---|---|---|---|---|
| F5 | ✓ | ✓ | ✓ | 37 mg/L |
| F6 | ✓ | ✓ | ✓ | 12 mg/L |
| F7 | ✓ | ✓ | ✓ | 11 mg/L |
| F8C | ✓ | ✓ | ✓ | 3.7 mg/L |
| F9A | ✓ | ✓ | ✓ | 8.7 mg/L |
| F9B | ✓ | ✓ | ✓ | 3.0 mg/L |
| F10A | ✓ | ✓ | ✓ | 2.0 mg/L |
| F11 | ✓ | ✓ | ✓ | 2.0 mg/L |
| F12 | ✓ | ✓ | ✓ | 2.8 mg/L |
| F13 | ✓ | ✓ | ✓ | 6.4 mg/L |
| F14 | ✓ | ✓ | ✓ | 2.4 mg/L |
| F15 | ✓ | ✓ | ✓ | 0.9 mg/L |
| BiTe | — | — | — | — |
| DART | — | — | — | — |

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate). All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as reference to an element or elements is intended to provide support for a similar aspect or embodiment of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. An isolated hetero-multimeric protein, which does not bind to CD16, and which comprises a first antigen-binding domain (ABD) that monovalently binds to a first antigen of interest and further comprises a second ABD which monovalently binds to a second antigen of interest, comprising:
   (a) a first polypeptide chain comprising a first variable domain (V) specific to the first antigen fused to a CH1 or CK constant region, a second variable domain specific to the second antigen and comprised within the second ABD, and an Fc domain or portion thereof interposed between the first and second variable domains; and
   (b) a second polypeptide chain comprising a first variable domain (V) specific to the first antigen fused to a CH1 or CK constant region selected to be complementary to the CH1 or CK constant region of the first polypeptide chain such that the first and second polypeptides form a CH1-CK heterodimer in which the first variable domain of the first polypeptide chain and the first variable domain of the second polypeptide form a first ABD that binds the first antigen of interest, and
wherein one of the antigens of interest is NKp46 and the other antigen of interest is a cancer antigen; and further wherein the first polypeptide chain comprises a third variable domain fused to the second variable domain, wherein the first and second polypeptide form a CH1-CK heterodimer, the first variable domain of the first polypeptide chain and the first variable domain of the second polypeptide chain form an antigen binding domain specific for the first antigen of interest, and the second and third variable domains of the first polypeptide chain form an scFv specific for the second antigen of interest, and still further wherein the hetero-multimeric polypeptide is a dimer with a monomeric Fc domain, having the domain arrangement:

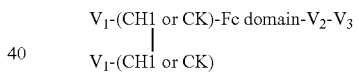

$V_1$-(CH1 or CK)-Fc domain-$V_2$-$V_3$
|
$V_1$-(CH1 or CK)

wherein each $V_1$, $V_2$ and $V_3$ is a heavy or light chain variable region; wherein the Fc domain comprises a CH3 domain with an amino acid mutation to prevent CH3-CH3 dimerization, which Fc domain does not bind to CD16; and further wherein one of the $V_1$ of the first polypeptide chain and the $V_1$ of the second polypeptide chain is a light chain variable domain and the other is a heavy chain variable domain.

2. An isolated hetero-multimeric protein, which does not bind to CD16, and which comprises a first antigen-binding domain (ABD) that monovalently binds to a first antigen of interest and further comprises a second ABD which monovalently binds to a second antigen of interest, comprising:
   (a) a first polypeptide chain comprising a first variable domain (V) specific to the first antigen fused to a CH1 or CK constant region, a second variable domain specific to the second antigen and comprised within the second ABD, and an Fc domain or portion thereof interposed between the first and second variable domains; and
   (b) a second polypeptide chain comprising a first variable domain (V) specific to the first antigen fused to a CH1 or CK constant region selected to be complementary to the CH1 or CK constant region of the first polypeptide chain such that the first and second polypeptides form a CH1-CK heterodimer in which the first variable domain of the first polypeptide chain and the first variable domain of the second polypeptide form a first ABD that binds the first antigen of interest, and wherein one of the antigens of interest is NKp46 and the other antigen of interest is a cancer antigen; and further wherein the first polypeptide chain comprises a third variable domain fused to the second variable domain, wherein the first and second polypeptide form a CH1-CK heterodimer, the first variable domain of the first polypeptide chain and the first variable domain of the second polypeptide chain form an antigen binding domain specific for the first antigen of interest, and the second and third variable domains of the first polypeptide chain form an scFv specific for the second antigen of interest, and still further wherein wherein the hetero-multimeric polypeptide is a dimer with a dimeric Fc domain, which dimeric Fc domain does not bind to CD16, and wherein said hetero-multimeric polypeptide has the domain arrangement:

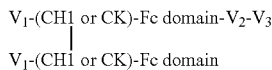

wherein each $V_1$, $V_2$ and $V_3$ is a heavy or light chain variable region; wherein the Fc domains comprise a CH2 and a CH3 domain capable of CH3-CH3 dimerization; and further wherein one of the $V_1$ of the first polypeptide chain and the $V_1$ of the second polypeptide chain is a light chain variable domain and the other is a heavy chain variable domain.

3. An isolated hetero-multimeric protein, which does not bind to CD16, and which comprises a first antigen-binding domain (ABD) that monovalently binds to a first antigen of interest and further comprises a second ABD which monovalently binds to a second antigen of interest, comprising:
(a) a first polypeptide chain comprising a first variable domain (V) specific to the first antigen fused to a CH1 or CK constant region, a second variable domain specific to the second antigen and comprised within the second ABD, and an Fc domain or portion thereof interposed between the first and second variable domains which does not bind to CD16; and
(b) a second polypeptide chain comprising a first variable domain (V) specific to the first antigen fused to a CH1 or CK constant region selected to be complementary to the CH1 or CK constant region of the first polypeptide chain such that the first and second polypeptides form a CH1-CK heterodimer in which the first variable domain of the first polypeptide chain and the first variable domain of the second polypeptide form a first ABD that binds the first antigen of interest, and wherein one of the antigens of interest is NKp46 and the other antigen of interest is a cancer antigen;
and further wherein the hetero-multimeric polypeptide is a trimeric polypeptide, comprising:
(a) a first polypeptide chain comprising a first variable domain (V) fused to a first CH1 or CK constant region, a second variable domain fused to a second CH1 or CK constant region, and an Fc domain or portion thereof interposed between the first and second variable domains;
(b) a second polypeptide chain comprising a variable domain fused at its C-terminus to a CH1 or CK constant region selected to be complementary to the first CH1 or CK constant region of the first polypeptide chain such that the first and second polypeptides form a CH1-CK heterodimer; and
(c) a third polypeptide chain comprising a variable domain fused at its C-terminus to a CH1 or CK constant region, wherein the variable domain and the constant region are selected to be complementary to the second variable domain and second CH1 or CK constant region of the first polypeptide chain such that the first polypeptide chain and the third polypeptide chain form a CH1-CK heterodimer bound by disulfide bond(s) formed between the CH1 or CK constant region of the third polypeptide and the second CH1 or CK constant region of the first polypeptide, but not between the CH1 or CK constant region of the third polypeptide and the first CH1 or CK constant region of the first polypeptide such that the first, second and third polypeptides form a CH1-CK heterotrimer, wherein the first variable domain of the first polypeptide chain and the variable domain of the second polypeptide chain form an antigen binding domain specific for the first antigen of interest, and the second variable domain of the first polypeptide chain and the variable domain of the third polypeptide chain form an antigen binding domain specific for the second antigen of interest and further-wherein the trimeric hetero-multimeric polypeptide has the domain arrangement:

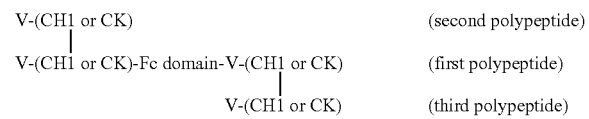

wherein the Fc domain comprises a CH3 domain with an amino acid mutation to prevent CH3-CH3 dimerization; wherein each V-V pairing occurs between a light chain variable domain and a heavy chain variable domain; and further wherein each constant region pairing occurs between a CH1 and a CK.

4. An isolated hetero-multimeric protein, which does not bind to CD16, which comprises a first antigen-binding domain (ABD) that monovalently binds to a first antigen of interest and further comprises a second ABD which monovalently binds to a second antigen of interest, said hetero-multimeric protein comprising:
(a) a first polypeptide chain comprising a first variable domain (V) specific to the first antigen fused to a CH1 or CK constant region, a second variable domain specific to the second antigen and comprised within the second ABD, and an Fc domain or portion thereof interposed between the first and second variable domains which does not bind to CD16; and
(b) a second polypeptide chain comprising a first variable domain (V) specific to the first antigen fused to a CH1 or CK constant region selected to be complementary to the CH1 or CK constant region of the first polypeptide chain such that the first and second polypeptides form a CH1-CK heterodimer in which the first variable domain of the first polypeptide chain and the first variable domain of the second polypeptide form a first ABD that binds the first antigen of interest, wherein one of the antigens of interest is NKp46 and the other antigen of interest is a cancer antigen;
and further wherein the hetero-multimeric polypeptide is a trimeric polypeptide, comprising:
(a) a first polypeptide chain comprising a first variable domain (V) fused to a first CH1 or CK constant region, a second variable domain fused to a second CH1 or CK constant region, and an Fc domain or portion thereof interposed between the first and second variable domains;

(b) a second polypeptide chain comprising a variable domain fused at its C-terminus to a CH1 or CK constant region selected to be complementary to the first CH1 or CK constant region of the first polypeptide chain such that the first and second polypeptides form a CH1-CK heterodimer; and (c) a third polypeptide chain comprising a variable domain fused at its C-terminus to a CH1 or CK constant region, wherein the variable domain and the constant region are selected to be complementary to the second variable domain and second CH1 or CK constant region of the first polypeptide chain such that the first polypeptide chain and the third polypeptide chain form a CH1-CK heterodimer bound by disulfide bond(s) formed between the CH1 or CK constant region of the third polypeptide and the second CH1 or CK constant region of the first polypeptide, but not between the CH1 or CK constant region of the third polypeptide and the first CH1 or CK constant region of the first polypeptide such that the first, second and third polypeptides form a CH1-CK heterotrimer, and wherein the first variable domain of the first polypeptide chain and the variable domain of the second polypeptide chain form an antigen binding domain specific for the first antigen of interest, and the second variable domain of the first polypeptide chain and the variable domain of the third polypeptide chain form an antigen binding domain specific for the second antigen of interest;

and further wherein the trimeric hetero-multimeric polypeptide comprises a dimeric Fc domain which does not bind CD16, which trimeric hetero-multimeric polypeptide has the domain arrangement:

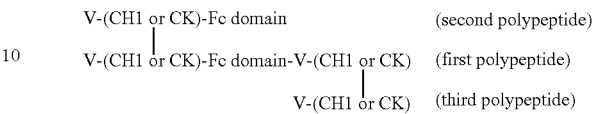

wherein each V-V pairing occurs between a light chain variable domain and a heavy chain variable domain, and wherein each constant region pairing occurs between a CH1 and a CK.

5. A pharmaceutical composition comprising an isolated protein according to claim 1, and a pharmaceutically acceptable carrier.

6. A pharmaceutical composition comprising an isolated protein according to claim 2, and a pharmaceutically acceptable carrier.

7. A pharmaceutical composition comprising an isolated protein according to claim 3, and a pharmaceutically acceptable carrier.

8. A pharmaceutical composition comprising an isolated protein according to claim 4, and a pharmaceutically acceptable carrier.

* * * * *